(12) United States Patent
Zaworotko et al.

(10) Patent No.: US 10,633,344 B2
(45) Date of Patent: Apr. 28, 2020

(54) MULTIPLE-COMPONENT SOLID PHASES CONTAINING AT LEAST ONE ACTIVE PHARMACEUTICAL INGREDIENT

(71) Applicants: University of South Florida, Tampa, FL (US); The Regents of the University of Michigan, Ann Arbor, MI (US)

(72) Inventors: Michael J. Zaworotko, Tampa, FL (US); Nair Rodriguez-Hornedo, Ann Arbor, MI (US); Brian Moulton, Temple Terrace, FL (US)

(73) Assignees: University of South Florida, Tampa, FL (US); The Regents of the University of Michigan, Ann Arbor, MI (US)

( * ) Notice: Subject to any disclaimer, the term of this patent is extended or adjusted under 35 U.S.C. 154(b) by 69 days.

(21) Appl. No.: 14/179,862

(22) Filed: Feb. 13, 2014

(65) Prior Publication Data
US 2014/0162989 A1 Jun. 12, 2014

Related U.S. Application Data

(63) Continuation of application No. 10/378,956, filed on Mar. 3, 2003.
(Continued)

(51) Int. Cl.
| | | |
|---|---|---|
| *C07D 223/26* | (2006.01) | |
| *A61K 9/16* | (2006.01) | |
| *A61K 31/167* | (2006.01) | |
| *A61K 31/192* | (2006.01) | |
| *A61K 31/4166* | (2006.01) | |
| *A61K 31/55* | (2006.01) | |
| *A61K 31/616* | (2006.01) | |
| *A61K 47/10* | (2017.01) | |
| *A61K 47/32* | (2006.01) | |
| *C07C 51/41* | (2006.01) | |
| *C07C 51/43* | (2006.01) | |
| *C07C 233/25* | (2006.01) | |
| *C07C 233/74* | (2006.01) | |
| *C07C 47/544* | (2006.01) | |
| *C07C 53/08* | (2006.01) | |
| *C07C 53/124* | (2006.01) | |
| *C07C 57/30* | (2006.01) | |
| *C07C 57/58* | (2006.01) | |
| *C07C 61/135* | (2006.01) | |
| *C07D 233/74* | (2006.01) | |

(Continued)

(52) U.S. Cl.
CPC .......... *C07D 223/26* (2013.01); *A61K 9/1652* (2013.01); *A61K 31/167* (2013.01); *A61K 31/192* (2013.01); *A61K 31/4166* (2013.01); *A61K 31/55* (2013.01); *A61K 31/616* (2013.01); *A61K 47/10* (2013.01); *A61K 47/32* (2013.01); *C07C 47/544* (2013.01); *C07C 51/412* (2013.01); *C07C 51/43* (2013.01); *C07C 53/02* (2013.01); *C07C 53/08* (2013.01); *C07C 53/124* (2013.01); *C07C 57/30* (2013.01); *C07C 57/58* (2013.01); *C07C 61/135* (2013.01); *C07C 63/307* (2013.01); *C07C 69/157* (2013.01); *C07C 205/57* (2013.01); *C07C 233/03* (2013.01); *C07C 233/25* (2013.01); *C07C 233/75* (2013.01); *C07C 317/04* (2013.01); *C07D 213/06* (2013.01); *C07D 213/22* (2013.01); *C07D 213/69* (2013.01); *C07D 213/79* (2013.01); *C07D 213/82* (2013.01); *C07D 233/74* (2013.01); *C07D 275/06* (2013.01)

(58) Field of Classification Search
CPC .. C07D 223/26; C07D 275/06; C07D 213/82; C07D 213/79; C07D 213/69; C07D 213/22; C07D 213/06; C07D 233/74; C06C 317/04; C06C 233/75; C06C 233/03; C06C 205/57; C06C 69/157; C06C 63/307; C06C 61/135; C06C 57/58; C06C 57/30; C06C 53/124; C06C 53/08; C06C 53/02; C06C 47/544; C06C 233/25; C06C 51/43; C06C 51/412; A61K 47/32; A61K 47/10; A61K 31/616; A61K 31/55; A61K 31/4166; A61K 31/192; A61K 31/167; A61K 9/1652
USPC ........................................................ 424/400
See application file for complete search history.

(56) References Cited

U.S. PATENT DOCUMENTS

| | | |
|---|---|---|
| 2,554,816 A | 5/1951 | Clapp et al. |
| 2,665,277 A | 1/1954 | Homeyer et al. |

(Continued)

FOREIGN PATENT DOCUMENTS

| | | |
|---|---|---|
| CA | 1 101 840 | 5/1981 |
| CA | 1 148 020 A1 | 6/1983 |

(Continued)

OTHER PUBLICATIONS

Notice of Reasons for Rejection dated Oct. 8, 2009 for Japanese Application No. 2003-572946. 11 pages.
(Continued)

*Primary Examiner* — Sahar Javanmard
(74) *Attorney, Agent, or Firm* — Wolf, Greenfield & Sacks, P.C.

(57) ABSTRACT

The subject invention concerns a method for identifying complementary chemical functionalities to form a desired supramolecular synthon. The subject invention also pertains to binary phase compositions comprising one or more pharmaceutical entities and methods for producing such compositions.

21 Claims, 25 Drawing Sheets
(23 of 25 Drawing Sheet(s) Filed in Color)

Related U.S. Application Data

(60) Provisional application No. 60/360,768, filed on Mar. 1, 2002.

(51) Int. Cl.
| | |
|---|---|
| *C07C 53/02* | (2006.01) |
| *C07C 63/307* | (2006.01) |
| *C07C 69/157* | (2006.01) |
| *C07C 205/57* | (2006.01) |
| *C07C 233/03* | (2006.01) |
| *C07C 233/75* | (2006.01) |
| *C07C 317/04* | (2006.01) |
| *C07D 213/06* | (2006.01) |
| *C07D 213/22* | (2006.01) |
| *C07D 213/69* | (2006.01) |
| *C07D 213/79* | (2006.01) |
| *C07D 213/82* | (2006.01) |
| *C07D 275/06* | (2006.01) |

(56) References Cited

U.S. PATENT DOCUMENTS

| | | | |
|---|---|---|---|
| 2,711,411 A | 6/1955 | Holbert et al. | |
| 2,980,679 A | 4/1961 | Gianfranco | |
| 3,028,420 A | 4/1962 | Petrow et al. | |
| 3,536,809 A | 10/1970 | Schaller et al. | |
| 3,598,123 A | 8/1971 | Zaffaroni | |
| 3,664,858 A * | 5/1972 | Huffman | 503/216 |
| 3,845,770 A | 11/1974 | Theeuwes et al. | |
| 3,916,899 A | 11/1975 | Theeuwes et al. | |
| 3,970,651 A | 7/1976 | Kaplan et al. | |
| 4,008,321 A | 2/1977 | Kamishita et al. | |
| 4,008,719 A | 2/1977 | Theeuwes et al. | |
| 4,198,507 A | 4/1980 | Barry et al. | |
| 4,267,179 A | 5/1981 | Heeres et al. | |
| 4,368,197 A | 1/1983 | Shefter et al. | |
| 4,513,006 A | 4/1985 | Maryanoff et al. | |
| 4,764,604 A | 8/1988 | Muller | |
| 4,792,569 A | 12/1988 | Maryanoff et al. | |
| 4,853,379 A | 8/1989 | Shroot et al. | |
| 4,916,134 A | 4/1990 | Heeres et al. | |
| 4,925,674 A | 5/1990 | Giannini et al. | |
| 4,927,855 A | 5/1990 | Lafon | |
| 4,994,604 A | 2/1991 | Tung et al. | |
| 5,006,513 A | 4/1991 | Hector et al. | |
| 5,023,092 A | 7/1991 | DuRoss | |
| 5,059,595 A | 10/1991 | Le Grazie | |
| 5,073,543 A | 12/1991 | Marshall et al. | |
| 5,120,548 A | 6/1992 | McClelland et al. | |
| 5,177,262 A | 1/1993 | Taylor et al. | |
| 5,242,942 A | 9/1993 | Costanzo et al. | |
| 5,258,402 A | 11/1993 | Maryanoff | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,332,834 A | 7/1994 | Bhattacharya et al. | |
| 5,338,644 A | 8/1994 | Taylor et al. | |
| 5,354,556 A | 10/1994 | Sparks et al. | |
| 5,356,467 A | 10/1994 | Oshlack et al. | |
| 5,366,738 A | 11/1994 | Rork et al. | |
| 5,380,867 A | 1/1995 | Bhattacharya et al. | |
| 5,384,327 A | 1/1995 | Costanzo et al. | |
| 5,387,700 A | 2/1995 | Maryanoff et al. | |
| 5,412,094 A | 5/1995 | Amos et al. | |
| 5,414,997 A | 5/1995 | Tailer | |
| 5,466,823 A | 11/1995 | Talley et al. | |
| 5,472,712 A | 12/1995 | Oshlack et al. | |
| 5,474,997 A | 12/1995 | Gray et al. | |
| 5,510,496 A | 4/1996 | Talley et al. | |
| 5,521,207 A | 5/1996 | Graneto | |
| 5,523,090 A | 6/1996 | Znaiden et al. | |
| 5,563,165 A | 10/1996 | Talley et al. | |
| 5,591,767 A | 1/1997 | Mohr et al. | |
| 5,614,342 A | 3/1997 | Molaire et al. | |
| 5,631,250 A | 5/1997 | Bunnell et al. | |
| 5,633,015 A | 5/1997 | Gilis et al. | |
| 5,633,272 A | 5/1997 | Talley et al. | |
| 5,635,535 A | 6/1997 | Wagstaff | |
| 5,639,476 A | 6/1997 | Oshlack et al. | |
| 5,641,512 A | 6/1997 | Cimiluca | |
| 5,661,151 A | 8/1997 | Saksena et al. | |
| 5,674,533 A | 10/1997 | Santus et al. | |
| 5,703,232 A | 12/1997 | Bunnell et al. | |
| 5,707,975 A | 1/1998 | Francois et al. | |
| 5,733,566 A | 3/1998 | Lewis | |
| 5,736,541 A | 4/1998 | Bunnell et al. | |
| 5,753,688 A | 5/1998 | Talley et al. | |
| 5,753,693 A | 5/1998 | Shank | |
| 5,760,007 A | 6/1998 | Shank et al. | |
| 5,760,068 A | 6/1998 | Talley et al. | |
| 5,932,598 A | 8/1999 | Talley et al. | |
| 5,935,933 A | 8/1999 | Shank et al. | |
| 5,952,187 A | 9/1999 | Stenglein et al. | |
| 5,972,986 A | 10/1999 | Seibert et al. | |
| 5,985,902 A | 11/1999 | Talley et al. | |
| 5,994,365 A | 11/1999 | Zaworotko et al. | |
| 5,998,380 A | 12/1999 | Ehrenberg et al. | |
| 5,998,413 A | 12/1999 | Heeres et al. | |
| 6,001,996 A | 12/1999 | Amos et al. | |
| 6,054,136 A | 4/2000 | Farah et al. | |
| 6,071,537 A | 6/2000 | Shank | |
| 6,132,420 A | 10/2000 | Dionne et al. | |
| 6,156,781 A | 12/2000 | Talley et al. | |
| 6,191,117 B1 | 2/2001 | Kozachuk | |
| 6,201,010 B1 | 3/2001 | Cottrell | |
| 6,245,357 B1 | 6/2001 | Edgren et al. | |
| 6,268,385 B1 | 7/2001 | Whittle et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,294,186 B1 | 9/2001 | Beerse et al. | |
| 6,294,192 B1 | 9/2001 | Patel et al. | |
| 6,319,903 B1 | 11/2001 | Carrazana et al. | |
| 6,323,266 B2 | 11/2001 | Phillips | |
| 6,333,050 B2 | 12/2001 | Wong et al. | |
| 6,342,249 B1 | 1/2002 | Wong et al. | |
| 6,348,458 B1 | 2/2002 | Hamied et al. | |
| 6,365,185 B1 | 4/2002 | Ritschel et al. | |
| 6,368,626 B1 | 4/2002 | Bhatt et al. | |
| 6,375,978 B1 | 4/2002 | Kleiner et al. | |
| 6,384,034 B2 | 5/2002 | Simitchieva et al. | |
| 6,403,640 B1 | 6/2002 | Stoner et al. | |
| 6,413,965 B1 | 7/2002 | Mylari | |
| 6,420,394 B1 | 7/2002 | Supersaxo | |
| 6,488,962 B1 | 12/2002 | Berner et al. | |
| 6,503,884 B1 | 1/2003 | Ehrenberg et al. | |
| 6,559,293 B1 | 5/2003 | Almarsson et al. | |
| 6,570,036 B1 | 5/2003 | Reuter | |
| 6,579,895 B2 | 6/2003 | Karim et al. | |
| 6,613,790 B2 | 9/2003 | Carter | |
| 6,699,840 B2 | 3/2004 | Almarsson et al. | |
| 7,078,526 B2 | 7/2006 | Remenar et al. | |
| 7,132,579 B2 | 11/2006 | Neckebrock et al. | |
| 7,205,413 B2 | 4/2007 | Morissette et al. | |
| 7,351,695 B2 | 4/2008 | Almarssoo et al. | |
| 7,446,107 B2 | 11/2008 | Remenar et al. | |
| 7,452,555 B2 | 11/2008 | Childs | |
| 7,459,449 B2 | 12/2008 | Keltjens | |
| 7,687,091 B2 | 3/2010 | Moen et al. | |
| 7,927,613 B2 | 4/2011 | Almarsson et al. | |
| 2002/0006951 A1 | 1/2002 | Hageman et al. | |
| 2002/0013357 A1 | 1/2002 | Nadkarni et al. | |
| 2002/0015735 A1 | 2/2002 | Hedden et al. | |
| 2002/0034542 A1 | 3/2002 | Thombre et al. | |
| 2002/0037925 A1 | 3/2002 | Dewey et al. | |
| 2002/0042446 A1 | 4/2002 | Dewey et al. | |
| 2002/0071857 A1 | 6/2002 | Kararli et al. | |
| 2002/0107250 A1 | 8/2002 | Hariharan et al. | |
| 2002/0119193 A1 | 8/2002 | Le et al. | |
| 2003/0069190 A1 | 4/2003 | Abdel-Magid et al. | |
| 2003/0096014 A1 | 5/2003 | Sherman | |
| 2003/0162226 A1 | 8/2003 | Cima et al. | |

(56) References Cited

U.S. PATENT DOCUMENTS

| | | |
|---|---|---|
| 2003/0166581 A1 | 9/2003 | Almarsson et al. |
| 2003/0224006 A1 | 12/2003 | Zaworotko et al. |
| 2004/0019211 A1 | 1/2004 | Remenar et al. |
| 2004/0053853 A1 | 3/2004 | Almarsson et al. |
| 2004/0106052 A1 | 6/2004 | Molaire |
| 2004/0106053 A1 | 6/2004 | Molaire et al. |
| 2004/0106055 A1 | 6/2004 | Molaire et al. |
| 2004/0171062 A1 | 9/2004 | Hirth et al. |
| 2004/0176335 A1 | 9/2004 | Childs |
| 2005/0070551 A1 | 3/2005 | Remenar et al. |
| 2005/0169982 A1 | 8/2005 | Almarsson et al. |
| 2005/0181041 A1 | 8/2005 | Goldman |
| 2005/0252649 A1 | 11/2005 | Chiu et al. |
| 2005/0256127 A1 | 11/2005 | Ku et al. |
| 2006/0134198 A1 | 6/2006 | Tawa et al. |
| 2006/0223794 A1 | 10/2006 | Bourghol et al. |
| 2007/0015841 A1 | 1/2007 | Tawa et al. |
| 2007/0021510 A1 | 1/2007 | Hickey et al. |
| 2007/0026078 A1 | 2/2007 | Almarsson et al. |
| 2007/0059356 A1 | 3/2007 | Almarsson et al. |
| 2007/0293674 A1 | 12/2007 | Scoppettuolo et al. |
| 2009/0088443 A1 | 4/2009 | Remenar et al. |
| 2010/0331285 A1 | 12/2010 | Almarsson et al. |

FOREIGN PATENT DOCUMENTS

| | | |
|---|---|---|
| EP | 0 310 122 A1 | 4/1989 |
| EP | 0 283 992 B1 | 9/1992 |
| EP | 0 413 528 B1 | 11/1995 |
| EP | 0 731 795 B1 | 12/1999 |
| EP | 1 167 355 A1 | 1/2002 |
| EP | 1 364 649 A1 | 11/2003 |
| FR | 769586 | 6/1934 |
| FR | 2 849 029 A1 | 6/2004 |
| GB | 1 297 261 A | 11/1972 |
| GB | 2 169 601 A | 7/1986 |
| IN | 182620 | 5/1999 |
| IT | 1303251 B1 | 11/2000 |
| JP | 46-33588 | 10/1971 |
| JP | B 46-33588 | 10/1971 |
| JP | 54-016494 | 2/1979 |
| JP | 54-095589 | 7/1979 |
| WO | WO 94/16733 A1 | 8/1994 |
| WO | WO 95/17407 A1 | 6/1995 |
| WO | WO 95/23596 A1 | 9/1995 |
| WO | WO 96/07331 A1 | 3/1996 |
| WO | WO 96/33193 A1 | 10/1996 |
| WO | WO 98/57967 A1 | 12/1998 |
| WO | WO 00/07583 A3 | 2/2000 |
| WO | WO 00/32189 A1 | 6/2000 |
| WO | WO 00/42021 A1 | 7/2000 |
| WO | WO 00/50020 A2 | 8/2000 |
| WO | WO 00/53283 A1 | 9/2000 |
| WO | WO 00/72841 A1 | 12/2000 |
| WO | WO 01/13904 A2 | 3/2001 |
| WO | WO 01/41536 A2 | 6/2001 |
| WO | WO 01/41760 A3 | 6/2001 |
| WO | WO 01/42221 A1 | 6/2001 |
| WO | WO 01/42222 A2 | 6/2001 |
| WO | WO 01/45706 A1 | 6/2001 |
| WO | WO 01/51919 A2 | 7/2001 |
| WO | WO 01/78724 A1 | 10/2001 |
| WO | WO 01/91750 A1 | 12/2001 |
| WO | WO 01/97853 A1 | 12/2001 |
| WO | WO 02/000627 A1 | 1/2002 |
| WO | WO 02/010125 A1 | 2/2002 |
| WO | WO 02/056878 A2 | 7/2002 |
| WO | WO 02/056915 A2 | 7/2002 |
| WO | WO 02/062318 A2 | 8/2002 |
| WO | WO 02/102376 A1 | 12/2002 |
| WO | WO 03/033462 A2 | 4/2003 |
| WO | WO 03/070738 A2 | 8/2003 |
| WO | WO 03/074474 A2 | 9/2003 |
| WO | WO 03/101392 A2 | 12/2003 |
| WO | WO 2004/054571 A1 | 7/2004 |
| WO | WO 2004/060347 A2 | 7/2004 |
| WO | WO 2004/078161 A1 | 9/2004 |
| WO | WO 2004/078163 A2 | 9/2004 |
| WO | WO 2004/089313 A2 | 10/2004 |
| WO | WO 2005/023198 A2 | 3/2005 |
| WO | WO 2005/037424 A1 | 4/2005 |
| WO | WO 2005/053612 A2 | 6/2005 |
| WO | WO 2005/055983 A2 | 6/2005 |
| WO | WO 2005/060968 A1 | 7/2005 |
| WO | WO 2005/077894 A1 | 8/2005 |
| WO | WO 2005/089375 A2 | 9/2005 |
| WO | WO 2005/094804 A1 | 10/2005 |
| WO | WO 2005/118577 A1 | 12/2005 |
| WO | WO 2006/024930 A1 | 3/2006 |

OTHER PUBLICATIONS

Definition of solvate, The Free Dictionary, http://www.thefreedictionary.com/solvate, accessed online on Jul. 21, 2009, pp. 1-3.
The Merck Index, 12$^{th}$ Ed. Merck & Co., Inc. Whitehouse Station, NJ. 1996. Entries 5683, 9094.
Physician's Desk Reference, 56th Ed., pp. 1800-1804, 2002.
Physician's Desk Reference, 56th Ed., pp. 2590-2595, 2002.
Press Release. "Clinical Development of Topiramate for Obesity Extended to Simplify Dosing, Improve Tolerability". http://www.orthomcneil.com/news/article020402.html (Feb. 4, 2002), New Jersey, 2 pages.
The United States Pharmacopoeia, 23rd Edition, U.S. Pharmacopoeia Convention, Inc. Rockville, MD, 1995, pp. 1843.
Aakeröy, C. et al. "A high-yielding supramolecular reaction" *J. Am. Chem. Soc.*, 2002, 14425-14432, vol. 124.
Aakeröy, C. et al. "A structural study of 2-amino-5-nitropyridine and 2-amino-3-nitropyridine: intermolecular forces and polymorphism" *J. Mater. Chem.*, 1998, pp. 1385-1389, vol. 8, No. 6.
Aakeröy, C. et al. "A versatile route to porous solids: organic-inorganic hybrid materials assembled through hydrogen bonds" *Angew. Chem. Int. Ed.*, 1999, pp. 1815-1819, vol. 38, No. 12.
Aakeröy, C. et al. "Aromatic dicarboxylic acids as building blocks of extended hydrogen-bonded architectures" *Supramolecular Chemistry*, 1998, pp. 127-135, vol. 9.
Aakeröy, C. et al. "Assembly of 2-D inorganic/organic lamellar structures through a combination of copper (I) coordination polymers and self-complimentary hydrogen bonds" *J. Chem. Soc., Dalton Trans.*, 2000, pp. 3869-3872.
Aakeröy, C. et al. "Building organic assemblies with 2-pyridone and dicarboxylic acids: relating molecular conformation and synthon stability to crystal structure" *Crystal Engineering*, 1998, pp. 225-241, vol. 1, No. 3-4.
Aakeröy, C. et al. "Charge-assisted hydrogen bonds and halogen-halogen interactions in organic and salts: benzylammonium benzoates and pentaflourobenzoates" *Structural Chemistry*, 1999, pp. 229-242, vol. 10, No. 3.
Aakeröy, C. et al. "Crystal engineering of hydrogen-bonded assemblies—a progress report" *Aust. J. Chem.*, 2001, pp. 409-421, vol. 54.
Aakeröy, C. et al. "Crystal engineering of ionic solids" *Modular Chemistry* (ed. by Michl, J.), 1997, pp. 153-162, Kluwer Academic Publishers, The Netherlands.
Aakeröy, C. et al. "Crystal engineering using intermolecular hydrogen-bonded connectors and classic coordination chemistry" *Transactions ACA*, 1998, pp. 97-103, vol. 33.
Aakeröy, C. et al. "Crystal engineering: strategies and architectures" *Acta Cryst.*, 1997, pp. 569-586, vol. B53.
Aakeröy, C. et al. "Deliberate combination of coordination polymers and hydrogen bonds in a supramolecular design strategy for inorganic/organic hybrid networks" *Chem. Commun.*, 2000, pp. 935-936.
Aakeröy, C. et al. "Di-hydroxy malonic acid as a building block of hydrogen-bonded 3-dimensional architectures" *Journal of Chemical Crystallography*, 1998, pp. 111-117, vol. 28, No. 2.
Aakeröy, C. et al. "Do polymorphic compounds make good cocrystallizing agents? A structural case study that demonstrates the importance of synthon flexibility" *Crystal Growth & Design*, 2003, 159-165, vol. 3, No. 2.

(56) References Cited

OTHER PUBLICATIONS

Aakeröy, C. et al. "Hydrogen-bonded layers of hydrogentartrate anions: two-dimensional building blocks for crystal engineering" *J. Mater. Chem.*, 1993, 1129-1135, vol. 3, No. 11.

Aakeröy, C. et al. "Hydrogen-bonding in solids" *Crystal Engineering* (ed. by Seddon, K. R. et al.), 1999, pp. 303-324, Kluwer Academic Publishers, The Netherlands.

Aakeröy, C. et al. "Low-dimensional architectures of silver coordination compounds assembled via amide-amide hydrogen bonds" *Crystal Engineering*, 1998, pp. 39-49, vol. 1, No. 1.

Aakeröy, C. et al. "Modular supramolecular synthesis based on a dominance hierarchy of intermolecular interactions (Abstract)" 223rd ACS National Meeting in Orlando, FL., Apr. 7-11, 2002, published by the American Chemical Society, Washington, D.C.

Aakeröy, C. et al. "Molecular mechanics and crystal engineering" *Crystal Engineering* (ed. by Seddon, K. R. et al.), 1999, pp. 69-82, Kluwer Academic Publishers, The Netherlands.

Aakeröy, C. et al. "New building blocks for crystal engineering. Syntheses and crystal structures of oxime-substituted pyridines" *Cryst Eng. Comm.*, 2000, pp. 1-6, vol. 27.

Aakeröy, C. et al. "Novel colorless composite materials for nonlinear optics" *Adv. Mater*, 1993, pp. 364-367, vol. 5, No. 5.

Aakeröy, C. et al. "Organic assemblies of 2-pyridones with dicarboxylic acids" *Tetrahedron*, 2000, pp. 6693-6699, vol. 56.

Aakeröy, C. et al. "Pitfalls in the supramolecular assembly of silver(I) coordination compounds" *Journal of Molecular Structure*, 1999, pp. 91-101, vol. 474.

Aakeröy, C. et al. "Solid state, crystal engineering and hydrogen bonds" *Comprehensive Coordination Chemistry II* (ed. by McCleverty, J. et al.), pp. 679-688, Elsevier Ltd., Oxford, UK.

Aakeröy, C. et al. "Supramolecular assembly of low-dimensional silver (I) architectures via amide-amide hydrogen bonds" *Chem. Commun.*, 1998, pp. 1067-1068.

Aakeröy, C. et al. "The C—H•••Cl hydrogen bond: does it exist?" *New J. Chem.*, 1999, pp. 145-152.

Aakeröy, C. et al. "The crystal structure of the molecular cocristal L-malic acid L-tartaric acid (1/1)" *Supramolecular Chemistry*, 1996, pp. 153-156, vol. 7.

Aakeröy, C. et al. "The hydrogen bond and crystal engineering" *Chemical Society Reviews*, 1993, pp. 397-407.

Aakeröy, C. et al. "Total synthesis' supramolecular style: design and hydrogen-bond-directed assembly of ternary supermolecules" *Angew. Chem. Int Ed.*, 2001, pp. 3240-3242, vol. 40, No. 17.

Aakeröy, C. et al. "Two-fold interpenetration of 3-D nets assembled via three-co-ordinate silver(I) ions and amide-amide hydrogen bonds" *J. Chem. Soc., Dalton Trans.*, 1998, pp. 1943-1945.

Aakeröy, C. et at "Heteromeric intermolecular interactions as synthetic tools for the formation of binary co-crystals" *Cryst. Eng. Comm.*, 2004, pp. 19-24, vol. 6, No. 5.

Aakeröy, C. et at "Hydrogen-bond assisted assembly of organic and organic-inorganic solids" *Crystal Enoineerino: From Molecules and Crystals to Materials*, 1999, pp. 89-106, Kluwer Academic Publishers, The Netherlands.

Aakeröy, C.B. et al. "Do Polymorphic Compounds Make Good Cocrystalizing Agents? A Structural Case Study that Demonstrates the Importance of Synthon Flexibility" *Crystal Growth & Design*, 2003, 3(2):159-165.

Ahn, S. et al. "Polymorphs of a 1:1 cocrystal with tunnel and layer structures: p,p'-biphenol/dimethyl sulfoxide" *Crystal Growth & Design*, 2001, pp. 107-111, vol. 1, No. 2.

Akazome, M. et al. "Enantioselective inclusion of methyl phenyl sulfoxides and benzyl methyl sulfoxides by (R)-phenylglycyl-(R)-phenylglycine and the crystal structures of the inclusion cavities" *J. Org. Chem.*, 2000, pp. 68-76, vol. 65.

Akhtaruzzaman, M.D. et al. "One-dimensional hydrogen-bonded molecular tapes in 1, 4-bis[(4-pyridinio) ethynyl]benzene chloranilate" *Acta. Cryst.*, 2001, pp. o353-o355, vol. E57.

Alberola, S. et al. "Crystalline and Molecular Structure of Sulfanilimide-Antipyrine" *Acta Cryst.*, 1977, pp. 3337-3341, vol. B33.

Allen, F. et al. "Systematic analysis of structural data as a research technique in organic chemistry" *Acc. Chem. Res.*, 1983, pp. 146-153, vol. 16.

Almarsson, Ö. et al. "Crystal engineering of the composition of pharmaceutical phases. Do pharmaceutical co-crystals represent a new path to improved medicines?" *Chem. Commun.*, 2004, pp. 1889-1896.

Amai, M. et al. "1:1 complex of octadecanoic acid and 3-pyridinecarboxamide" *Acta Cryst.*, 1998, pp. 1367-1369, vol. C54.

Ammar et al., Effects of Aromatic Hydtotropes on the Solubility of Carbamazepine. Part II: Effect of Nicotinamide, Sodium Salts of Benzoic, Naphthoic and Nicotinic Acids. Egypt J Pharmacol Sci. 1994;35(1-6):209-23.

Anderson, J. "Constitution of aurous compounds: Gold mirrors" *Nature*, Oct. 2, 1937, pp. 583-584, Letters to the Editor.

Anderson, N. et al. "Sulfonation with inversion by mitsunobu reaction: an improvement on the original conditions" *J. Org. Chem.*, 1996, pp. 7955-7958, vol. 61.

Aoki, K. et al. "A 1:1 complex of theophylline and p-nitrophenol" *Acta Cryst.*, 1978, pp. 2333-2336, vol. B34.

Aronhime, J. et al. "Crystalline forms of pharmaceuticals and characterization thereof", Oral Presentation, Mar. 8, 2005, USPTO, Alexandria, VA.

Ashton, P. et al. "Combining different hydrogen-bonding motifs to self-assemble interwoven superstructures" *Chem. Eur. J.*, 1998, pp. 577-589, vol. 4, No. 4.

Ball, P. "Materials Chemistry—Scandal of Crystal Design . . . ", *Nature*, Jun. 20, 1996, pp. 648-650, vol. 381.

Barker, P. A. et al. "Effect of crystallization temperature on the cocrystallization temperature on the cocrystallization of hydroxybutyrate/hydroxyvalerate copolymers" *Polymer*, pp. 913-919, vol. 38, No. 4.

Bastin, R.J. et al. "Salt Selection and Optimisation Procedures for Pharmaceutical New Chemical Entities" *Organic Process Research & Development*, 2000, 4:427-435.

Beerges, P. et al. "Phenothiazine tetracyanoethylene" *Private Communication*, 1994.

Berkovitch-Yellin, Z. et al. "Electron density distribution in cumulenes: an x-ray study of the complex allenedicarboxylic acid-acetamide (1:1) at −150° C." *Acta Cryst.*, 1977, pp. 3670-3677, vol. B33.

Berkovitch-Yellin, Z. et al. "The role played by C—H•••O and C—H•••N interactions in determining molecular packing and conformation" *Acta Cryst.*, 1984, pp. 159-165, vol. B40.

Berl, V. et al. "Induced fit selection of a barbiturate receptor from a dynamic structural and conformational/configurational library" *Eur. J. Org. Chem.*, 1999, pp. 3089-3094.

Bernstein, J. et al. "Concomitant Polymorphs", *Angew. Chem., Int. Ed.*, 1999, pp. 3440-3461, vol. 38.

Bertolasi, V. et al. "Competition between hydrogen bonding and donor-acceptor interactions in co-crystals of 1,3-dimethylbarbituric acid with aromatic amines" *New J. Chem.*, 2001, pp. 408-415, vol. 25.

Bertolasi, V. et al. "General rules for the packing of hydrogen-bonded crystals as derived from the analysis of squaric acid anions: aminoaromatic nitrogen base co-crystals" *Acta Cryst.*, 2001, pp. 591-598, vol. B57.

Bettinetti, G. et al. "Structure and solid-state chemistry of anhydrous and hydrated crystal forms of the trimethoprim-sulfamethoxypyridazine 1:1 molecular complex" *Journal of Pharmaceutical Sciences*, Apr. 2000, pp. 478-489, vol. 89, No. 4.

Bettinetti, G. et al. "Thermal analysis of binary systems of the pharmaceuticals trimethoprim and benzoic acid" *Journal of Thermal Analysis*, 1983, pp. 285-294, vol. 28.

Bettis, J. et al. "Biopharmaceutics and dosage form design" *Amer. J. Hosp. Pharm.*, Mar. 1973, pp. 240-243, vol. 30.

Bingham, A. et al. "Over one hundred solvates of sulfathiazole" *Chem. Commun.*, 2001, pp. 603-604.

Bolton, S. et al. "Complexes formed in solution by homologs of caffeine" *Journal of the American Pharmaceutical Association*, Jan. 1957, pp. 38-41, vol. XLVI, No. 1.

Bond, A. "In situ co-crystallisation as a tool for low-temperature crystal engineering" *Chern. Commun.*, 2003, pp. 250-251, vol. 2.

(56) References Cited

OTHER PUBLICATIONS

Bond, A.D. et al. "On the Polymorphism of Aspirin" *Angew. Chem. Int Ed.*, 2007, 46:615-617.
Bond, A.D. et al. "On the Polymorphism of Aspirin: Crystalline Aspirin as Intergrowths of Two "Polymorphic" Domains" *Angew. Chem. Int. Ed.*, 2007, 46:618-622.
Bonin, M. et al. "Urotropin azelate: a rather unwilling co-crystal" *Acta Cryst.*, 2003, pp. 72-86, vol. B59.
Bosshard, C. et al. "Microscopic nonlinearities of two-component organic crystals" *J. Opt. Soc. Am. B*, Nov. 2001, pp. 1620-1626, vol. 18, No. 11.
Boucher, E. et al. "Use of Hydrogen-Bonds to Control Molecular Aggregation. Behavior of Dipyridones and Pyridone-Pyrimidones Designed to Form Cyclic Triplexes", *J. Org. Chem.*, 1995, pp. 1408-1412, vol. 60.
Brader, M.L. et al. "Hybrid insulin cocrystals for controlled release delivery" *Nature Biotechnology*, Aug. 2002, 20:800-804.
Braga, D. et al. "Hydrogen bonding interactions between ions: a powerful tool in molecular crystal engineering" *Structure and Bonding*, 2004, pp. 1-32, vol. 111.
Brierley, C. et al. "Preparation and structure of the 1:2 π-molecular complex of phenothiazine with pyromellitic dianhydride" *J. Chem. Phys.*, Feb. 1, 1985, pp. 1522-1528, vol. 82, No. 1.
Brittain, H.G. et al. "Polymorphism in Pharmaceutical Solids" 1999, New York: Marcel Dekker, pp. 183, 202-208, 219.
Buczak, G. et al. "Crystal structure and vibrational spectra of the 1:1 and 1:2 complexes of pyridine betaine with pentachlorophenol" *Journal of Molecular Structure*, 1997, pp. 143-151, vol. 436-437.
Bunick, G. et al. "The crystal and molecular structure of the complex 2,6-diamino-9-ethylpurine 5,5-diethylbarbituric acid" *American Crystallographic Association, Abstract Papers* Winter 1976, p. 30.
Burgi, H. et al. "Crystallisation of supramolecular materials" *Current Opinion in Solid State & Materials Science*, 1998, pp. 425-430, vol. 3.
Byriel, K., et al. "Molecular cocrystals of carboxylic acids. IX Carboxylic acid interactions with organic heterocyclic bases. The crystal structures of the adducts of (2,4-dichlorophenoxy) acetic acid with 3-hydroxypyridine, 2,4,6,-trinitrobenzoic acid with 2-aminopyrimidine, and 4-nitrobenzoic acid with 3-amino-1,2,4-triazole" *Aust. J. Chem.*, 1992, pp. 969-981, vol. 45, No. 6.
Byrn, S. R. et al. "Solid-state pharmaceutical chemistry" *Chem. Mater.*, 1994, pp. 1148-1158, vol. 6.
Cacciapuoti, A. et al. "In vitro and in vivo activities of SCH 56592 (Posaconazole), a new triazole antifungal agent, against *Aspergillus* and *Candida*" *Antimicrobial Agents and Chemotherapy*, Aug. 2000, pp. 2017-2022, vol. 44, No. 8.
Caira, M. "Molecular complexes of sulfonamides. Part 3. Structure of 5-methoxysulfadiazine (Form II) and its 1:1 complex with acetylsalicylic acid" *Journal of Chemical Crystallography*, 1994, pp. 695-701, vol. 24, No. 10.
Caira, M. "Molecular complexes of sulfonamides. Part 1. 1:1 complexes between sulfadimidine [4-amino-N-(4,6-dimethyl-2-pyrimidinyl) benzenesulfonamide] and 2- and 4-aminobenzoic acids" *Journal of Crystallographic and Spectroscopic Research*, 1991, pp. 641-648, vol. 21, No. 5.
Caira, M. "Molecular complexes of sulfonamides. Part 2. 1:1 complexes between drug molecules: sulfadimidine—acetylsalicylic acid and sulfadimidine-4-aminosalicylic acid" *Journal of Crystallographic and Spectroscopic Research*, 1992, pp. 193-200, vol. 22, No. 2.
Caira, M. et al. "Order-disorder enantiotropy, monotropy, and isostructurality in a tetroxoprim-sulfametrole 1:1 molecular complex: crystallographic and thermal studies" *Journal of Pharmaceutical Sciences*, Nov. 2003, pp. 2164-2176, vol. 92, No. 11.
Caira, M. et al. "Selective formation of hydrogen bonded cocrystals between a sulfonamide and aromatic carboxylic acids in the solid state" *J. Chem. Soc. Perkin Trans. 2*, 1995, pp. 2213-2216.

Caira, M. et al. "Structure of a 1:1 complex between the anthelmintic drug mebendazole and propionic acid" *Journal of Chemical Crystallography*, 1998, vol. 28, No. 1.
Caira, M. et al. "X-ray structure and thermal analysis of a 1:1 complex between (S)-naproxen and heptakis (2,3,6-tri-O-methyl)-β-cyclodextrin" *Journal of Inclusion Phenomena and Molecular Recognition in Chemistry*, 1995, pp. 277-290, vol. 20.
Callahan, J.C. et al. "Equilibrium moisture content of pharmaceutical excipients" *Drug Development and Industrial Pharmacy*, 1982, pp. 355-369, vol. 8, No. 3.
Camerman, A. et al. "Hydrogen bonding interaction of diphenylbarbituric acid and 9-ethyladenine. Crystal structure of a 1:1 complex" *Can. J. Chem.*, 2000, pp. 1045-1051, vol. 78.
Camerman, A. et al. "Molecular structure of acetylacetone. A crystallographic determination" *J. Am. Chem. Soc.*, 1983, pp. 1584-1586, vol. 105, No. 6.
Cannon, A. et al. "Noncovalent derivatization: green chemistry applications of crystal engineering" *Crystal Growth & Design*, 2002, pp. 255-257, vol. 2. No. 4.
Caronna, T. et al. "Halogen bonding and π•••π stacking control reactivity in the solid state" *J. Am. Chem. Soc.*, 2004, pp. 4500-4501, vol. 126.
Chang, Y. L. et al. "An Approach to the Design of Molecular-Solids. Strategies for Controlling the Assembly of Molecules Into Two-Dimensional Layered Structures", *J. Am. Chem. Soc.*, 1993, pp. 5991-6000, vol. 115.
Childs, S. et al. "Crystal engineering approach to forming cocrystals of amine hydrochlorides with organic acids. Molecular complexes of fluoxetine hydrochloride with benzoic, succinic, and fumaric acids" *J. Am. Chem. Soc.*, 2004, pp. 13335-13342, vol. 126.
Chinnakali, K. et al. "2-aminopyrimidine and p-phenylene-diacetic acid (1:1) co-crystal" *Acta Cryst.*, 1999, pp. 399-401, vol. C55.
Choi, C. et al. "Cocrystallization of melaminium levulinate monohydrate" *Acta Cryst.*, 2004, pp. o295-o296, vol. C60.
Chow, Y. P. et al. "Complexation of acetaminophen with methyl xanthines" *Journal of Pharmaceutical Sciences*, 1972, pp. 1454-1458, vol. 61.
Christian, S. et al. "Activity coefficient effects in spectral and solubility studies of molecular complex equilibria" *Journal of the American Chemical Society*, Sep. 20, 1972, pp. 6861-6862, vol. 94, No. 19, Communications to the editor.
Coll, M. et al. "Molecular structure of the complex formed between the anticancer drug cisplatin and d(pGpG): C222$_1$ crystal form" *Journal of Biomolecular Structure & Dynamics*, 1990, pp. 315-330, vol. 8, No. 2.
Copp, S. et al. "Supramolecular chemistry of [Mn(CO)$_3$ (μ3-OH)]$_4$: Assembly of a cubic hydrogen-bonded diamondoid network with 1,2-diamineothane" *J. Am. Chem. Soc.*, 1992, pp. 8719-8720, vol. 114.
Cordi, A. et al. "(S)-Spiro [(1, 3-diazacyclopent-1-ene)-5, 2'-(7'-methyl-1,2',3',4'-tetrahydronaphthalene)]: resolution, stereospecific synthesis, and preliminary pharmacological characterization as a partial α-adrenergic agonist" *J. Med. Chem.*, 1997, pp. 2931-2935, vol. 40.
Cowan, J.A. et al. "Neutron diffraction studies of the 1:1 and 2:1 cocrystals of benzene-1,2,4,5-tetracarboxylic acid and 4,4'-bipyridine" *Acta Crystallographica Section C: Crystal Structure Communications*, 2006, C62:o157-0161.
Cox, J.R. et al., "Selective Crystal Growth of the Anhydrous and Monohydrate Forms of Theophylline on Self-Assembled Monolayers," *Angew, Chem. Int. Ed.*, 2007, pp. 1988-1991, Vo. 46.
Craven, M. et al. "The 2:1 crystal complex of 5, 5-diethylbarbituric acid (barbital) and caffeine" *Acta Cryst.*, 1974, pp. 1191-1195, vol. B30.
Craven, M. et al. "The crystal structures of two polymorphs of 5,5'-diethylbarbituric acid (barbital)" *Acta Cryst.*, 1969, pp. 1978-1993, vol. 825.
Crihfield, a. et al. "Crystal engineering through halogen bonding. 2. Complexes of diacetylene-linked heterocycles with organic iodides" *Crystal Growth & Design*, 2003, pp. 313-320, vol. 3, No. 3.
Cudney, B. et al. "Screening and optimization strategies for macromolecular crystal growth" *Acta Cryst.*, 1994, pp. 414-423, vol. D50.

(56) References Cited

OTHER PUBLICATIONS

Cutsem, J. V. et al. "Oral and parenteral therapy with saperconazole (R 66905) of invasive aspergillosis in normal and immunocompromised animals" *Antimicrobial Agents and Chemotheraphy*, Dec. 1989, pp. 2063-2068, vol. 33, No. 12.

Dannaoui, E. et al. "Acquired itraconazole resistance in *Aspergillus fumigatus*" *Journal of Antimicrobial Chemotherapy*, 2001, pp. 333-340, vol. 47.

Database WPI, Section Ch, Week 197936, Derwent Publishing Ltd., London, Great Britain, AN 1979-65538B, XP002282989 and JP 54 095589A (Sumitomo) 1979 Abstract.

Datta, S. et al. "Crystal structures of drugs: advances in determination, prediction and engineering" *Nature*, Jan. 2004, pp. 42-57, vol. 3.

Datta, S. et al. "Molecular complex formation between riboflavin and salicylate in an aqueous medium" *Bult Chem. Soc. Jpn.*, 2003, pp. 1729-1734, vol. 76.

Davey, R. J. et al. "Crystal engineering—nucleation, the key step" *Cryst Eng. Comm.*, 2002, pp. 257-264, vol. 4, No. 47.

Davey, R. J. et al. "Crystallisation in polymer films: control of morphology and kinetics of an organic dye in a polysilicone matrix" *J. Mater. Chem.*, 1997, pp. 237-241, vol. 7, No. 2.

Davidovich, M. et al. "Detection of Polymorphism by Powder X-Ray Diffraction Interference by Preferred Orientation" *American Pharmaceutical Review*, 2004, pp. 10, 12, 14, 16, 100, vol. 7, No. 1.

Davies, N.M. ef al. "Clinical Pharmacokinetics and Pharmacodynamics of Celecoxib: A Selective Cyclo-Oxygenase-2 Inhibitor" *Clin Pharmacokinet*, Mar. 2000, 38(3):225-242.

De Jong, E.M.G.J. et al. "Dystrophic Psoriatic Fingernails Treated with 1% 5-Fluorouracil in a Nail Penetration-Enhancing Vehicle: A Double-Blind Study" *Dermatology*, 1999, 199:313-318.

Dean, J.A. "Analytical Chemistry Handbook" 1995, New York: McGraw-Hill, Inc., pp. 10.24-10.26.

Debernardis, J. et al. "Conformationally defined adrenergic agents. 5. Resolution, absolute configuration, and pharmacological characterization of the enantiomers of 2-(5,6-dihydroxy-1,2,3,4-tetrahydro-1-naphthyl) imidazoline: a potent agonist at α-adrenoceptors" *J. Med. Chem.*, 1987, pp. 1011-1017, vol. 30.

Denning, D. W. et al. "In vitro activity of Saperconazole (R66 905) compared with Amphotericin B and Itraconazole against *Aspergillus* species" *Eur. J. Clin. Microbial Infect. Dis.*, 1990, pp. 693-697, vol. 9.

Desiraju, G. "Supramolecular synthons in crystal engineering—A new organic synthesis" *Angew. Chem. Int. Ed. Engl*, 1995, pp. 2311-2327, vol. 34.

Desiraju, G. et al. "Crystal and co-crystal" *Cryst. Eng. Comm.*, 2003, pp. 466-467, vol. 5, No. 82.

Desiraju, G. et al. "Crystal engineering: outlook and prospects" *Current Science*, Oct. 25, 2001, pp. 1038-1042, vol. 81, No. 8.

Desiraju, G. R. "Chemistry beyond the molecule" *Nature*, Jul. 26, 2001, pp. 397-400, vol. 412.

Desiraju, G. R. "Crystal Gazing: Structure Prediction and Polymorphism", *Science*, Oct. 17, 1997, pp. 404-405, vol. 278, No. 5337.

Desiraju, G. R. "The C—H•••O Hydrogen Bond in Crystals: What Is It?" *Acc. Chem. Res.*, 1991, pp. 24:290-296.

Desiraju, G. R., "Crystal engineering: A brief overview," *J. Chem. Sci.*, Sep. 2010, pp. 667-675, vol. 122, No. 5.

Doelker, E. "Crystalline Modifications and Polymorphism changes during drug manufacturing" *Annales Pharmaceutiques Francaises*, 2002, 60(3):161-176.

Doelker, E. "Physicochemical behavior of active substances. Consequences for the feasibility and stability of pharmaceutical forms" *S.T.P. Pharma Practiques*, 1999, 9(5):399-409.

Doi, M. et al. "Conformational study of a potent human renin inhibitor: x-ray crystal structure of isopropyl (2R, 3S)-4-cyclohexy1-2-hydroxy-3-{N-[(2R)-2-morpholinocarbonylmethyl-3-(1-naphthyl) propionyl]-L-histidylamino}butyrate (KRI-1314), a pentapeptide analogue with amino acid sequence corresponding to the cleavage site of angiotensinogen" *J. Chem. Soc. Perkin Trans. 1*, 1991, pp. 1153-1158.

Dressman, J. B. et al. "Dissolution testing as a prognostic tool for oral drug absorption: immediate release dosage forms" *Pharmaceutical Research*, 1998, pp. 11-22, vol. 15, No. 1.

Duax, W. et al. "The structure of the crystalline complex estradiol. Urea (1:1)" *Acta Cryst.*, 1972, pp. 1864-1871, vol. B28.

Dunitz, J. "Crystal and co-crystal: a second opinion" *Cryst. Eng. Comm.*, 2003, pp. 506, vol. 5, No. 91.

Dunitz, J. "New light on an old story: the solid-state transformation on ammonium cyanate into urea" *J. Am. Chem. Soc.*, 1998, pp. 13274-13275, vol. 120.

Dunitz, J. D. "Are crystal structures predictable" *Chem Commun.*, 2003, pp. 545-548.

Dvorkin et al. "Crystal and Molecular Structure of a Complex 18-crown-6 with 6-chloro-7-sulfamido-3,4-dihydro-1,2,4-benzothiadiazine-1, 1-dioxide (hypothiazide) of 1:1 Composition" *Kristallagrafiya*, 1990, 35(3):682-686.

Ebert, W. R. "Soft elastic gelatin capsules: a unique dosage form" *Pharmaceutical Technology*, Oct. 1977, pp. 44-50, vol. 1, No. 5.

El-Nahhas, S.A. "Physico-Chemical characteristics of Carbamazepine-beta-cyclodextrin inclusion compounds and carbamazepine-peg solid dispersions" *Pharmazie*, 1996, 51(12):960-963.

Enright, G. et al. "Thermally programmable gas storage and release in single crystals of an organic van der Waals host" *J. Am. Chem. Soc.*, 2003, pp. 9896-9897, vol. 125.

Epstein, R. et al. "The x-ray crystal structure of the molecular complex 8-bromo-9-ethyladenine-5-allyI-5-isobutylbarbituric acid" *Acta Cryst.*, 1976, pp. 2180-2188, vol. B32.

Ermer, O. et al. "Molecular recognition among alcohols and amines: super-tetrahedral crystal architectures of linear diphenol-diamine complexes and aminophenols" *J. Chem. Soc. Perkins Trans. 2*, 1994, pp. 925-944.

Etter, M. "Encoding and decoding hydrogen-bond patterns of organic compounds" *Acc. Chem. Res.*, 1990, pp. 120-126, vol. 23.

Etter, M. "Hydrogen bonds as design elements in organic chemistry" *J. Phys. Chem.*, 1991, pp. 4601-4610, vol. 95.

Etter, M. et al. "Graph-set analysis of hydrogen-bond patterns in organic crystals" *Acta Cryst.*, 1990, pp. 256-262, vol. B46.

Etter, M. et al. "Hydrogen bond directed cocrystallization and molecular recognition properties of acyclic imides" *J. Am. Chem. Soc.*, 1991, pp. 2586-2598, vol. 113.

Fabian, L. et al. "Volumetric measure of isostructurality" *Acta Cryst.*, 1999, pp. 1099-1108, vol. B55.

Fallon III, L. "The crystal and molecular structure of 5-fluorouracil" *Acta Cryst.*, pp. 2549-2556, vol. B29.

Faught, E. et al. "Topiramate Dose-Ranging Trial in Refractory Partial Epilepsy" *Amer. Epilepsy Soc. Proc.*, 1995,p. 33, vol. 36, Supp. 4.

Feibush, B. et al. "Chiral separation of heterocyclic drugs by HPLC: solute-stationary phase base-pair interactions" *J. Am. Chem. Soc.*, 1986, pp. 3310-3318, vol. 108.

Felthouse et al., Maleic Anhydride, Maleic Acid, and Fumaric Acid. 2001. http://www.huntsman.com/performance_products/media/komaleic.pdf.

Feynman, R. "There's Plenty of Room at the Bottom", *Engineering and Science*, Feb. 1960, pp. 22-36.

Fifer, E. et al. "Fentanyl analogues 3. 2-(1,2,3,4-tetrahydro)-naphthyl substituted 4-anilidopiperidines" *Eur. J. Med. Chem.—Chim. Ther.*, 1984, pp. 519-524, vol. 19, No. 6.

Fitzgerald, G.A. et aL "The Coxibs, Selective Inhibitors of Cyclooxygenase-2", *New England Journal of Medicine*, Aug. 9, 2001, 345(6):433-442.

Fleischman, S.G. et al. "Crystal Engineering of the Composition of Pharmaceutical Phases: Multiple-Component Crystalline Solids Involving Carbamazepine" *Crystal Growth & Design.*, 2003, 3(6):909-919.

Fleischman, Scott et al. , Crystal engineering of binary crystals that contain pharmaceutical molecules, Abstracts of Papers, 23rd ACS National Meeting, Orlando, FL, United States, Apr. 7-11, 2002, IEC-076.

(56) References Cited

OTHER PUBLICATIONS

Foxman, B. M. et al. "Environmentally benign synthesis using crystal engineering: steric accommodation in non-covalent derivatives of hydroquinones" *Crystal Engineering*, 1998, pp. 109-118, vol. 1, No. 1.

Foxman, B. M. et al. "Noncovalent derivatives of hydroquinone: BIS-(N,N-dialkyl) bicyclo[2.2.2]octane-1,4-dicarboxamide complexes" *Crystal Engineering*, 1999, pp. 55-64, vol. 2. No. 1.

Freemont, Cocrystal structure of an editing complex of Klenow fragment with DNA. PNAS. Dec. 1988;85(23):8924-8.

Fritchie, C. et al. "The configuration of phenothiazine in various molecular complexes" *Chem Commun.*, 1968, pp. 833-834.

Fujii, S. et al. "Crystal and molecular structure of a 1:1 molecular complex of adenine and riboflavin" *Archives of Biochemistry and Biophysics*, 1977, pp. 363-370, vol. 181.

Fung, H.L. et al. "Solvent Effects on Comparative Dissolution of Pharmaceutical Solvates" *Chemical and Pharmaceutical Bulletin*, 1974, 22(2):454-458.

Gao, X et al. "Supramolecular construction of molecular ladders in the solid state" *Angew. Chem. Int. Ed.*, 2004, pp. 232-236, vol. 43.

Gartland, G. L. et al. "Hydrogen bonding NH•••O=C of barbiturates: the (1:1) crystal complex of urea and 5,5-diethylbarbituric acid (barbital)" *Acta Cryst.*, 1974, pp. 980-987, vol. B30.

Gascon, M. -P. et al. "In vitro forecasting of drugs which may interfere with the biotransformation of midazolam" *Eur. J. Clin. Pharmacol.*, 1991, pp. 573-578, vol. 41.

Gavezzotti, A. "Are crystal structures predictable?" *Acc. Chem. Res.*, 1994, pp. 309-314, vol. 27.

Ghosh, M. "Structure and conformation of the 1:1 molecular complex sulfaproxyline-caffeine" *Acta Cryst.*, 1991, pp. 577-580, vol. C47.

Giuseppetti, G. P. et al. "The crystal structure of a sulfamethoxazole-trimethoprim 1:1 molecular compound" *Il Farmaco—Ed. Sc.*, pp. 138-151, vol. 35.

Gluzman, M. Kh. et al. "Investigation of Eutectic Melting in Systems Composed of Organic Salts and Acids" *Journal of Physical Chemistry*, 1960, pp. 2742-2747, vol. 34.

Goswami, S. et al. "1:1 Hetero-assembly of 2-amino-pyramidine and (+)-camphoric acid" *Acta Cryst.*, 2000, pp. 477-478, vol. C56.

Goswami, S. et al. "2-aminopyrimidine-fumaric acid cocrystal" *Acta Cryst.*, 1999, pp. 583-585, vol. C55.

Goswami, S. et al. "Molecular recognition induced supramolecular array of 2-aminopyrimidine with terephthalic acid, 1,4-phenylenediacetic acid and furmaric acid in solid state via H-bonding and π-stacking interactions" *Supramolecular Chemistry*, 1999, pp. 25-33, vol. 11.

Graja, A. et al. "Interplay of acceptor molecule shape, crystal structure and physical properties of a new molecular complex $C_{70} \cdot 2[(Ph_3P) AuCl]$" *Chemical Physics Letters*, Nov. 19, 1999, pp. 725-732. vol. 313.

Groth, P. "d-Glucose-sodium chloride-monohydrate (glucose-sodium chloride)=$2C_6H_{12}O_6 \cdot NaCl \cdot H_2O$" *Chemische Krystallographie*, 1910, pp. 438-439.

Guarrera, D. et al. "Molecular self-assembly in the solid state. The combined use of solid state NMR and differential scanning calorimetry for the determination of phase constitution" *Chem. Mater.*, 1994, pp. 1293-1296, vol. 6.

Haixin, L. et at "Structure of the 1:1 complex of 6,6'-diquinolyl ether with 5,5-diethylbarbituric acid" *Acta Cryst.*, 1992, pp. 2096-2098, vol. C48.

Harkema, S. et al. "The crystal structure of urea oxalic acid (2:1)" *Acta Cryst.*, 1972, pp. 1646-1648, vol. B28.

Haynes, D. "Supramolecular synthon competition in organic sulfonates: A CSD survey" *Cryst Eng. Comm.*, 2004, pp. 584-588, vol. 6, No. 95.

Heeres, J. et al. "Antimycotic azoles. 7. Synthesis and antifungal properties of a series of novel triazol-3-ones" *J. Med. Chem.*, 1984, pp. 894-900, vol. 27.

Helfrich, B. et al. "Polymorphism as an indication of structural versatility (Abstract)" 223rd ACS National Meeting in Orlando, FL., Apr. 7-11, 2002, published by the American Chemical Society, Washington, D.C.

Henck, J. et al. "Disappearing and reappearing polymorphs. The benzocaine:picric acid system" *J. Am. Chem. Soc.*, 2001, pp. 1834-1841, vol. 123.

Hepperle, M. et al. "Mono N-arylation of piperazine(III): metal-catalyzed N-arylation and its application to the novel preparations of the antifungal posaconazole and its advanced intermediate" *Tetrahedron Letters*, 2002, pp. 3359-3363, vol. 43.

Higuchi, T. et al. "Complexation of organic substances in aqueous solution by hydroxyaromatic acids and their salts" *J. Pharm. Sci.*, 1961, pp. 905-909, vol. 50.

Hino, T. et al. "Assessment of nicotinamide polymorphs by differential scanning calorimetry" *Thermochimica Acta*, 2001, pp. 85-92, vol. 374.

Högberg, T. et al. "Crystallographic, theoretical and molecular modelling studies on the conformations of the salicylamide, raclopride, a selective dopamine-$D_2$ antagonist" *J. Pharm. Pharmacol.*, 1987, pp. 787-796, vol. 39.

Honig, P. K. et al. "Itraconazole affects single-dose Terfenadine pharmacokinetics and cardiac repolarization pharmacodynamics" *J. Clin. Pharmacol.*, 1993, pp. 1201-1206, vol. 33.

Hsu, I. et al. "Hydrogen bonding NH . . . N of barbiturates: The 1:1 crystal complex of imidazole and 5,5-diethylbarbituric acid (barbital)" *Acta Cryst.*, 1974, pp. 988-993, vol. 830.

Hsu, I. et al. "The 1:1 crystal complex of N-methyl-2-pyridone and 5,5-diethylbarbituric acid (barbital)" *Acta Cryst.*, 1974, pp. 998-1001, vol. B30.

Hsu, I. et al. "The 2:1 crystal complex of 2-aminopyridine and 5,5-diethylbarbituric acid (barbital)" *Acta Cryst.*, 1974, pp. 994-997, vol. B30.

Hsu, I. et al. "The crystal structure of the 1:1 complex of acetamide with 5,5-diethylbarbituric acid (barbital)" *Acta Cryst.*, 1974, pp. 974-979, vol. B30.

Hsu, I. et al. "The crystal structure of the triclinic 1:2 complex of hexamethylphosphoramide with 5,5-diethylbarbituric acid (barbital)" *Acta Cryst.*, 1974, pp. 1299-1304, vol. B30.

Hsu, I. et al. "The crystalline complex (1:1) of salicylamide and 5-ethyl-5-isoamylbarbituric acid (amobarbital)" *Acta Cryst.*, 1974, pp. 843-846, vol. B30.

Hu, Z. et al. "Separation of 4-aminobenzoic acid by cocrystallization: Crystal structure of the complex of 4-aminobenzoic acid with (2R,3R)-tartaric acid" *Journal of Chemical Crystallography*, Dec. 2002, pp. 525-529, vol. 32, No. 12.

Huang, C.-M. et al. "Molecular packing modes. Part XI. Crystal structures of the 2:1 complexes of benzamide with succinic acid and furamide with oxalic acid" *J. Chem. Soc. Perkins Trans. 2: Physical Organic Chemistry*, 1973, pp. 503-508, vol. 5.

Ibragimov, B. "A simple correlation between the structures of different crystal modifications of a given host-guest complex and their crystallization temperatures" *Journal of Inclusion of Phenomena and Macrocyclic Chemistry*, 1999, pp. 345-353, vol. 34.

Imai, T. et al. "Successful treatment of cerebral Aspergillosis with a high oral dose of Itraconazole after excisional surgery" *Internal Medicine*, Oct. 1999, pp. 829-832, vol. 38, No. 10.

Ishida, T. et al. "Structural study of histamine $H_2$-receptor antagonists. Five 3-[2-(diaminomethyleneamino)-4-thiazolymethylthio] propionamidine and -amide derivatives" *Acta Cryst.*, 1989, pp. 505-512, vol. 645.

Ito et al., Compelled Orientational Control of the Solid-State Photodimerization of trans-Cinnamamides: Dicarboxylic Acid as a Non-covalent Linker. Tetrahedron. 2000;56:6833-44.

Iwamoto et al., Structure of Cinnamamide. Acta Cryst. 1989;C45:1110-2.

Jackisch, M. et al. Structures of three related biphenyl compounds: 4,4'-biphenyldiol, 3,3',5,5'-tetra-tert-butyl-4,4'-biphenyldiol, and 3,3',5,5'-tetra-tert-butyl-1,1'-bicyclohexa-2,5-dienylidene-4,4'-dione *Acta Cryst.*, 1990, pp. 919-922, vol. C46.

Jain, N.K. et al. "Polymorphism in Pharmacy" *Indian Drugs*, 1986, 23(6):315-329.

(56) References Cited

OTHER PUBLICATIONS

Jiang et al., Cinnamamide, an antitumor agent with low cytotoxicity acting on matrix metalloproteinase. Anti-Cancer Drugs. Jan. 2000;11(1):49-54.
Katakai, R. et al. "Stepwise synthesis of oligopeptides with N-carboxy-α-amino acid anhydrides. IV. Glycine NCA" *J. Org. Chem.*, 1972, pp. 327-329, vol. 37, No. 2.
Kawakami, Y. et al. "The rationale for E2020 as a potent acetylcholinesterase inhibitor" *Bioorganic & Medicinal Chemistry*, 1996, pp. 1429-1446, vol. 4, No. 9.
Kelders, H. et al. "Automated protein crystallization and a new crystal form of a subtilisin: eglin complex" *Protein Engineering*, 1987, pp. 301-303, vol. 1, No. 4.
Khalil, R. M. "Complexation of paracetamol with xanthine derivatives" *Egypt. J. Pharm. Sol.*, 1992, pp. 757-769, vol. 33, No. 5-6.
Kim, H. et al. "High-performance liquid chromatographic analysis of the anti-fungal agent SCH 56592 in dog serum" *Journal of Chromatography B*, 2000, pp. 93-98, vol. 738.
Kim, S. "Crystal structure of the 1:1 complex of 5-fluorouracil and 9-ethylhypoxanthine" *Science*, Nov. 24, 1967, pp. 1046-1048, vol. 158, No. 3804.
Kim, S. et al. "The structure of a crystalline complex containing one phenobarbital molecule and two adenine derivatives" *Proc. Natl. Acad. Sci. USA*, 1968, pp. 402-408, vol. 60.
Kirchner, M.T. et al. "Co-crystals with Acetylene: Small Is not Simple" *Chem. Eur J.*, 2010, 16:2131-2146.
Kiryu, S. et al. "Crystal structure of a 1:1 aminopyrine-barbital complex" *Journal of Pharmaceutical Sciences*, May 1971, pp. 699-703, vol. 60, No. 5.
Kiryu, S. et al. "Crystal structure of a 1.1 aminopyrine-cyclobarbital complex" *Chem. Pham. Bull.*, 1974, pp. 1588-1592, vol. 22.
Klein, C.L. et al. "Molecular Structure of Two Conformationally Restrained Fentanyl Analogues: cis- and trans-lsomers of N-{3-Methyl-1-[2-(1,2,3,4-tetrahydro)naphthyl]-4-piperidinyl}-N-phenylpropanamide" *Journal of Pharmaceutical Sciences*, Nov. 1985, 74(11):1147-1151.
Kobayashi, H. et al. "Sinusoidal structure of the 1:1 complex of phenothiazine and 7,7,8,8-tetracyanoquinodimethane, PTZ-TCNQ" *Acta Cryst.*, 1974, pp. 1010-1017, vol. B30.
Kofler, L. et al., *Thermal micromethods for the study of organic compounds and their mixtures*, pp. 1-145, 148-351, 354-386, Innsbruck, Austria, 1980.
Koshima, H. et al. "Photoreactivities of two kinds of bimolecular crystals formed from acridine and phenothiazine" *J. Chem. Soc., Perkins Trans. 2*, 1997, pp. 2033-2038.
Koshima, H. et al. "Polymorphs of a cocrystal with achiral and chiral structures prepared by pseudoseeding: tryptamine/hydrocinnamic acid" *Crystal Growth & Design*, 2001, pp. 355-357, vol. 1, No. 5.
Kovacs, J. et al. "New type of bridged monoamino-β-cyclodextrins" *Journal of Inclusion Phenomena and Molecular Recognition in Chemistry*, 1996, pp. 53-56, vol. 25.
Krantz, J. et al. "Sodium theophylline glycinate" *Journal of the American Pharmaceutical Association*, 1946, pp. 248-250.
Krishnamohan Sharma, C. V. et al. "X-ray crystal structure of $C_6H_3(CO_2H)_3$-1,3,5•1.5(4,4'-bipy): a 'super trimesic acid' chicken-wire grid" *Chem. Commun.*, 1996, pp. 2655-2656.
Kuroda, R. et al. "Generation of a co-crystal phase with coloristic properties via solid state grinding procedures" *Chem. Commun.*, 2002, pp. 2848-2849.
Lavrijsen, A. P. M. et al. "Hepatic injury associated with itraconazole" *The Lancet*, Jul. 25, 1992, pp. 251-252, vol. 340.
Le Jeunne, C. et al. "Comparative efficacy and safety of calcium carbasalate plus metoclopramide versus ergotamine tartrate plus caffeine in the treatment of acute migraine attacks" *Eur. Neurol.*, 1999, pp. 37-43, vol. 41.
Leger, J.M. et al. "Crystal Structure of the 1:1 Sulfacetamide-Caffeine Complex" *Acta Cryst.*, 1977, pp. 1455-1459, vol. 633.
Lehn, J.-M. et al. "Molecular recognition directed self-assembly of ordered supramolecular strands by cocrystallization of complementary molecular components" *Chem. Soc., Chem. Commun.*, 1990, pp. 479-481.
Leiserowitz, L. "Molecular packing modes. Carboxylic acids" *Acta Cryst.*, 1976, pp. 775-802, vol. B32.
Leiserowitz, L. et al. "The molecular packing modes and hydrogen-bonding properties of amide: dicarboxylic acid complexes" *Acta Cryst.*, 1977, pp. 2719-2733, vol. B33.
Levin, B. et al. "The not-so-trivial synthesis and characterization of heterocyclic boronic acids (Abstract)" 38th Midwest Regional Meeting of the American Chemical Society in Columbia, MO., Nov. 5-7, 2003, published by the American Chemical Society, Washington, D.C.
Lynch, D. et al. "1:1 Molecular complexes of 4-amino-N-(4,6-dimethylpyrimidin-2-yl) benzene-sulfonamide (sulfamethazine) with indole-2-carboxylic acid and 2,4-dinitrobenzoic acid" *Aust. J. Chem.*, 2000, pp. 383-387, vol. 53.
Lynch, D. et al. "Molecular cocrystals of carboxylic acids. XV Preparation and characterization of heterocyclic base adducts with a series of carboxylic acids, and the crystal structures of the adducts of 2-aminopyrimidine with 2,6-dihydroxybenzoic acid, 4-aminobenzoic acid, phenoxyacetic acid, (2,4-dichlorophenoxy) acetic acid, (3,4-dichlorophenoxy)-acetic acid and salicylic acid, and 2-aminopyridmine with 2,6-dihydroxybenzoic acid" *Aust. J. Chem.*, 1994, pp. 1097-1115, vol. 47.
Lynch, D. et al. "Molecular cocrystals of carboxylic acids. XXXI adducts of 2-aminopyrimidine and 3-amino-1,2,4-triazole with heterocyclic carboxylic acids" *Aust. J. Chem.*, 1998, pp. 403-408, vol. 51.
MacGillivray, L. et al. "Supramolecular control of reactivity in the solid state using linear molecular templates" *J. Am. Chem. Soc.*, 2000, pp. 7817-7818, vol. 122.
Madarasz, J. et al. "Thermal, ftir and xrd study on some 1:1 molecular compounds of theophylline" *Journal of Thermal Analysis and Calorimetry*, 2002, pp. 281-290, vol. 69.
Martin, R. et al. "Polyphenal-caffeine complexation" *J. Chem. Soc., Chem. Commun.*, 1986, pp. 105-106.
Martin, R. et al. The caffeine-potassium chlorogenate molecular complex *Phytochemistry*, 1987, pp. 273-279, vol. 26, No. 1.
Martins, F.T. et al., "Intermolecular Contacts Influencing the Conformational and Geometric Features of the Pharmaceutically Preferred Mebendazole Polymorph C," *Journal of Pharmaceutical Sciences*, Jul. 2009, pp. 2336-2344, vol. 98, No. 7.
Maryanoff, B. "Stereochemistry in a medium-sized ring. Highly diastereoselective N-oxidation of a substituted 3-benzazonine. X-ray crystal structure of an unusual complex between an amine N-oxide and saccharin" *J. Org. Chem.*, 1990, pp. 760-764, vol. 55.
Mastropaolo, D. et al. "Hydrogen bonding interaction of diphenylhydantoin and 9-ethyladenine" *Molecular Pharmacology*, 1983, pp. 273-277, vol. 23.
Mathias, J. et al. "Structural preferences of hydrogen-bonded networks in organic solution—the cyclic $CA_3•M_3$ 'rosette'" *J. Am. Chem. Soc.*, 1994, pp. 4316-4325, vol. 116.
McCrone, W. C. "Polymorphism", In: The Physics and Chemistry of the Organic Solid State, vol. II, Fox, D. et al. (eds.), 1965, pp. 725-767, Interscience, New York.
McIntosh, J. et al. "Chemotherapeutic drugs in anaerobic infections of wounds" *The Lancet*, Jun. 26, 1943, pp. 793-795.
McIntosh, J. et al. "Further observations on the chemotherapy of experimental gas gangrene: flavazole, marfanil, V187 and V335" *British Journal of Experimental Pathology*, 1946, pp. 46-54, vol. 27.
McIntosh, J. et al. "Zinc peroxide, proflavine and penicillin in experimental cl. welchii infections" *The Lancet*, Dec. 26, 1942, pp. 750-752.
McMahon, J. et al. "Crystal engineering of the composition of pharmaceutical phases. $3^1$. Primary amide supramolecular heterosynthons and their role in the design of pharmaceutical co-crystals" *Z Kristallogr.*, 2005, pp. 340-350, vol. 220.

(56) References Cited

OTHER PUBLICATIONS

Meejoo, S. et al. "The interplay of aryl-perfluoroaryl stacking interactions and interstack hydrogen bonding in controlling the structure of a molecular cocrystal" *Chemphyschem*, 2003, pp. 766-769, vol. 4.
Mirmehrabi, M. et al. "Improving the filterability and solid density of ranitidine hydrochloride form 1" *Journal of Pharmaceutical Sciences*, Jul. 2004, pp. 1692-1700, vol. 93, No. 7.
Morris, K. et al. "Theoretical approaches to physical transformations of active pharmaceutical ingredients during manufacturing processes" *Advanced Drug Delivery Reviews*, 2001, pp. 91-114, vol. 48.
Moulton, B. et al. "From Molecules to Crystal Engineering: Supramolecular Isomerism and Polymorphism in Network Solids", *Chem. Rev.*, 2001, pp. 1629-1658, vol. 101.
Munn, R. et al. "A Model for resonance-assisted hydrogen bonding in crystals and its graph set analysis" *J. Phys. Chem. A*, 2001, pp. 6938-6942, vol. 105.
Muzaffar, N.A. et al. "Polymorphism and Drug Availability" *Journal of Pharmacy (Lahore)*, 1997, 1(1):59-66.
Nakanishi, I. et aL "X-ray structural studies on two forms of β-cyclodextrin barbital complexes" *Journal of Inclusion Phenomena*, 1984, pp. 689-699, vol. 2.
Nakao, S. et al. "The crystal and molecular structure of the 2:1 molecular complex of theophylline with phenobarbital" *Acta Cryst.*, 1977, pp. 1373-1378, vol. B33.
Natarajan, S. et al. "Reinvestigation of the crystal structure of diglycine hydrochloride" *Zeitschrift für Kristallographic*, 1992, pp. 265-270, vol. 198.
Neuvonen, P. J. et al. "Itraconazole drastically increases plasma concentrations of lovastatin and lovastatin acid" *Clinical Pharmacology & Therapeutics*, 1996, pp. 54-61, vol. 60, No. 1.
Nomeir, A. A. et al. "Pharmacokinetics of SCH 56592, a new azole broad-spectrum antifungal agent, in mice, rats, rabbits, dogs, and cynomolgus monkeys" *Antimicrobial Agents and Chemotherapy*, Mar. 2000, pp. 727-731, vol. 44, No. 3.
Odds, F. C. "Antifungal activity of saperconazole (R 66 905) in vitro" *Journal of Antimicrobial Chemotherapy*, 1989, pp. 533-537, vol. 24.
Olenik, B. et al. "Cooperative and anticooperative effects in the cocrystals of mono- and diazanaphthalenes with meso-1, 2-diphenyl-1,2-ethanediol" *Crystal Growth & Design*, 2003, pp. 175-181, vol. 3, No. 2.
Olenik, B. et al. "Supramolecular synthesis by cocrystallization of oxalic and fumaric acid with diazanaphthalenes" *Crystal Growth & Design*, 2003, pp. 183-188, vol. 3, No. 2.
Osorio-Lozada, A. et al. "Synthesis and determination of the absolute stereochemistry of the enantiomers of adrafinil and modafinil" *Tetrahedron: Asymmetry*, 2004, 15:3811-3815.
Oswald, I. et al. "Rationalisation of co-crystal formation through knowledge-mining" *Crystallography Reviews*, 2004, pp. 57-66, vol. 10, No. 1.
Oswald, I.D.H. et al. "The formation of paracetamol (acetaminophen) adducts with hydrogen-bond acceptors" *Acta Crystallographica Section B*, 2002, B58:1057-1066.
Otsuka, M. et al. "Effect of Polymorphic Forms of Bulk Powders on Pharmaceutical Properties of Carbamazepine Granules" *Chem Pharm Bull*, 1999, 47(6):852-856.
Ouyang, X. et al. "Single-crystal-to-single-crystal topochemical polymerizations of a terminal diacetylene: two remarkable transformations give the same conjugated polymer" *J. Am. Chem. Soc.*, 2003, pp. 12400-12401, vol. 125.
Patel, U. et al. "Structure of the 1:1 complex between 4-amino-N-(4,6-dimethyl-2-pyrimidinyl)-benzenesulfonamide (sulfadimidine) and 2-hydroxybenzoic acid (salicylic acid)" *Acta Cryst.*, 1988, pp. 1264-1267, vol. C44.
Pedireddi, V.R. et al. "Layered Structures Formed by Dinitrobenzoic Acids" *Tetrahedron Letters*, 1998, 39:9831-9834.
Privitera, M. et al. "Dose-Ranging Trial with Higher Doses of Topiramate in Patients with Resistant Partial Seizures", *Amer. Epilepsy Soc. Proc.*, 1995, p. 33, vol. 36, Supp. 4.
Quehenberger, H. "Concerning organic molecular compounds and their polymorphism" *Monatshefte für Chemie*, 1949, pp. 595-606, vol. 80, No. 5.
Rasenack, N. et al. "Dissolution Rate Enhancement by in Situ Micronization of Poorly Water-Soluble Drugs" *Pharmaceutical Research*, Dec. 2002, 19(12):1894-1900.
Reck, G. et al. "Crystal structures of the carbamazepine/ammonium chloride and carbamazepine/ammonium bromide adducts and their transformation into carbamazepine dihydrate" *Pharmazie*, 1991, pp. 509-512, vol. 46, No. 7.
Reddy, L. et al. "Phenyl-perfluorophenyl synthon mediated cocrystallization of carboxylic acids and amides" *Crystal Growth & Design*, 2004, pp. 89-94, vol. 4., No. 1.
Remenar, J. F. et al. "Crystal engineering of novel cocrystals of a triazole drug with 1,4-dicarboxylic acids" *J. Am. Chem. Soc.*, 2003, pp. 8456-8457, vol. 125.
Remenar, J. F. et al. "Celecoxib sodium salt: engineering crystal forms for performance" *CrystEngComm*, 2011, 13:1081-1089.
Reynolds, J. E. F. (ed). Martindale, The Extra Pharmacopoeia, 1993, The Pharmaceutical Press, London, England, 13th Edition, pp. 1431 (e.g., Acetaminophen, Aspirin, and Caffeine Tablets), 1465 (e.g., Aspirin plus C), 1521 (Codafen Continus), 1610 (Gaboril Complex).
Robbins, A. H. et al. "The crystal structure of the 1:2 adduct of potassium triiodide and 5,5-diethylbarbituric acid (barbital)" *American Crystallographic Association—Series 2 Papers and Abstracts*, 1973, p. 87.
Rosenfeld, W. E. "Topiramate: A Review of Preclinical, Pharmacokinetic, and Clinical Data" *Clinical Therapeutics*, 1997, 1916):1294-1308.
Rubino, J.T. et al. "Influence of solvent composition on the solubilities and solid-state properties of the sodium salts of some drugs" *International Journal of Pharmaceutics*, 1990, 65:141-145.
Sachdeo, S.K. et al. "Topiramate: Double-Blind Trial as Monotherapy", *Amer. Epilepsy Soc. Proc.*, 1995, p. 33, vol. 36, Supp. 4.
Saksena, A. K. et al. "Advances in the chemistry of novel broad-spectrum orally active azole antifungals: recent studies leading to the discovery of SCH 56592" in *Advances in the Chemistry of Novel Broad-Spectrum Orally Active Azole Antifunoals* (Royal Soc. Chem., Cambridge), 1997, pp. 180-199.
Saksena, A. K. et al. "Concise asymmetric routes to 2,2,4-trisubstituted tetrahydrofurans via chiral titanium imide enolates: key intermediates towards synthesis of highly active azole antifungals SCH 51048 and SCH 56592" *Tetrahedron Letters*, 1996, pp. 5657-5660, vol. 37, No. 32.
Salem, M.S. et al. "Preparation, characterisation and transformation of terfenadine polymorphic forms" *International Journal of Pharmaceutics*, 1996, 141:257-259.
Salmon, J. et al. "Supramolecular chemistry of boronic acids (Abstract)" 38th Midwest Regional Meeting of the American Chemical Society in Columbia, MO., Nov. 5-7, 2003, published by the American Chemical Society, Washington, D.C.
Scarbrough, F. et al. "Crystal structure of a complex between lumiflavin and 2,6-diamino-9-ethylpurine: a flavin adenine dinucleotide model exhibiting charge-transfer interactions" *Proc. Natl. Acad. Sci. USA*, Nov. 1976, pp. 3807-3811, vol. 73, No. 11.
Schmidt, G. "Photodimerization in the solid state" *Pure Appl. Chem.*, 1971, pp. 647-678, vol. 27.
Shan, N. et al. "Co-crystal of 4,7-phenanthroline and carboxylic acids: synthon competition and prediction" *Tetrahedron Letters*, 2002, pp. 8721-8725, vol. 43.
Shan, N. et al. "Crystal engineering using 4,4'-bipyridyl with di- and tricarboxylic acids" *Crystal Engineering*, 2002, pp. 9-24, vol. 5.
Shan, N. et al. "Mechanochemistry and co-crystal formation: effect of solvent on reaction kinetics" *Chem. Commun.*, 2002, pp. 2372-2373.
Shan, N. et al. "Supramolecular synthons in the co-crystal structures of 2-aminopyrimidine with diols and carboxylic acids" *Tetrahedron Letters*, 2002, pp. 3101-3104, vol. 43.

(56) References Cited

OTHER PUBLICATIONS

Shattock, T. R. et al. "Hierarchy of Supramolecular Synthons: Persistent Carboxylic Acid••• Pyridine Hydrogen Bonds in Cocrystals that also contain a Hydroxyl Moiety" *Crystal Growth 7 Design*, 2008, pp. 4533-4545, vol. 8, No. 12.

Shaviv, R. et al. "Magnetochemistry of the tetrahaloferrate (III) ions 6. Crystal structure and magnetic ordering in [(pyH)$_3$Cl] [FeCl$_4$]$_2$" *Inorganica Chimica Acta*, 1992, pp. 613-621, vol. 198-200.

Shefter, E. "Structural studies on complexes IV: Crystal structure of a 1:1 5-chlorosalicylic acid and theophylline complex" *Journal of Pharmaceutical Sciences*, 1969, pp. 710-714, vol. 58.

Shefter, E. et al., ACS, Abstr. Papers (Summer), 1970, 35, compound name: sulfathiazole-theophylline complex.

Shimizu, N. et al. "Structure of 2,4-diamino-5-(3,4,5-trimethoxybenzyl) pyrimidine-5,5-diethylbarbituric acid (1:1)" *Acta Cryst.*, 1982, pp. 2309-2311, vol. B38.

Simonov, Y. et al. "Structure of the caffeine-copper(II) acetate additional compound", *Izvestiya Akademii Nauk Moldayskoi SSR, Seriya Fiziko-Tekhnicheskikh i Matematicheskikh Nauk*, 1972, vol. 3, pp. 83-84, abstract only.

Singh, N. B. et al. "Solid state reaction between 8-hydroxyquinoline and p-nitrobenzoic acid" *Indian Journal of Chemistry*, May 1988, pp. 429-432, vol. 37B.

Smith, D. et al. "Structure confirmation by single crystal X-ray diffraction of a series of new schiff bases and theoretical computations on 3-(N-2-α, α, α-triflourotoluylidene amino) tetrahydrothiophene-1, 1-dioxide (Abstract)" 216th ACS National Meeting in Boston, MA., Aug. 23-27, 1998, published by the American Chemical Society, Washington, D.C.

Smith, G. et al. "Interactions of aromatic carboxylic acids with quinolin-8-ol (oxine): Synthesis and the crystal structures of the proton-transfer compounds with the nitro-substituted benzoic acids" *Aust. J. Chem.*, 2001, pp. 171-175, vol. 54.

Smith, G. et al. "Molecular cocrystals of carboxylic acids. XXI The role of secondary group interactions in adduct formation between 2-aminopyramidine and substituted benzoic acids: the crystal structures of the adducts with o-phthalic acid, o-nitrobenzoic acid, o-aminobenzoic acid and m-aminobenzoic acid" *Aust. J. Chem.*, 1995, pp. 1151-1166, vol. 48.

Smith, G. et al. "The 1:1 adduct of 4-aminobenzoic acid with 4-aminobenzonitrile" *Acta Cryst.*, 2000, pp. 1155-1156, vol. C56.

Smith et al., The Determination of the Crystal Structure of Anhydrous Theophylline by X-ray Powder Diffraction with a Systematic Search Algorithm, Lattice Energy Calculations, and $^{13}$C and $^{15}$N Solid-State NMR: A Question of Polymorphism in a Given Unit Cell. J Phys Chem B. 2001;105(24):5818-26.

Stahl, P.H. *The Practice of Medicinal Chemistry*; "Chapter 35: Preparation of water-soluble compounds through salt formation" Jan. 1, 2003, Elsevier, NL, pp. 601-615, XP002566271.

Stahly, G. P. "A Survey of Cocrystals Reported prior to 2000" *Crystal Growth & Design*, 2009, 9:4212-4229.

Stalker, R. et al. "Asymmetric synthesis of two new conformationally constrained lysine derivatives" *Tetrahedron*, 2002, pp. 4837-4849, vol. 58.

Steiner, T. "Donor and acceptor strengths in C—H•••O hydrogen bonds quantified from crystallographic data of small solvent molecules" *New. J. Chem.*, 1998, pp. 1099-1103.

Stezowski, J. J. et al. "Characterization of a 1:1 complex of an unusual structure in the phenothiazine/phenazine binary phase diagram" Zeitschrift fur Kristallographie in *International Journal for Structural, Physical, Chemical Aspects of Crystalline Materials*, 1983, pp. 213-215, vol. 162, No. 1-4.

Storey, R. et al. "Automation of solid form screening procedures in the pharmaceutical industry-how to avoid the bottlenecks" *Crystallography Reviews*, 2004, pp. 45-56, vol. 10, No. 1.

Summers, M.P. et al. "The polymorphism of aspirin" *J. Pharm. Pharmac.*, 1970, 22:615-616.

Szafran, M. et al. "Molecular structures and hydrogen bonding in the 1:1 and 1:2 complexes of pyridine betaine with 2,6-dichloro-4-nitrophenol; an example of strongly coupled hydrogen bonds, 0-H•••O=C-0-H•••0-" *Journal of Molecular Structure*, 1997, pp. 145-160, vol. 416.

Takeuchi, M. et al. "Synchrotron radiation SAXS/WAXS study of polymorph-dependent phase behavior of binary mixtures of saturated monoacid triacylglycerols" *Crystal Growth & Design*, 2003, pp. 369-374, vol. 3, No. 3.

Tang, C. P. et al. "Reaction pathways in crystalline host-guest inclusion complexes: rotation by a net 180° of the acetyl group on photoaddition of guest-acetophenone and -*m*-Chloroacetophenone to the atom C5 of host deoxycholic acid" *J. Am. Chem. Soc.*, 1985, pp. 4058-4070, vol. 107.

Taylor, R. et aL "Rules governing the crystal packing of mono- and dialcohols" *Acta Crystallographica Section B, Structural Science*, 2001, pp. 815-827, vol. B57.

Thallapally, P. et al. "Polymorphism of 1,3,5-trinitrobenzene induced by a trisindane additive" *Angew. Chem. Mt. Ed.*, 2004, pp. 1149-1155, vol. 43.

Thayer, A.M. et al. "Form and Function" *Chemical & Engineering News*, Jun. 18, 2007, 85(25):17-30 (8 pages).

Timmerman, P. et al. "Noncovalent Assembly of functional groups on calix[4]arene molecular boxes" *Chem. Eur. J.*, 1997, pp. 1823-1832, vol. 3., No. 11.

Tomura, M. et al. "One-dimensional zigzag chain structures with intermolecular C—H•••πand C—H•••O interactions consisted of phthalic acid and pyridine derivatives" *Chemistry Letters*, 2001, pp. 532-533.

Trask, A. et al. "Crystal engineering of organic cocrystals by the solid-state grinding approach" *Top Curr. Chem.*, 2005, pp. 41-70, vol. 254.

Trask, A. et al. "Pharmaceutical cocrystallization: engineering a remedy for caffeine hydration" *Crystal Growth & Design*, 2005, pp. 1013-1021, vol. 5, No. 3.

Trask, A. et al. "Solvent-drop grinding: green polymorph control of cocrystallisation" *Chem. Commun.*, 2004, pp. 890-891 in addition to supplemental materials.

Trowbridge, L. et al. "Composites for nonlinear optics: Crystal growth and polymorphism" *University of Sussex, Falmer Brighton UK, School of Chemistry and Molecular Sciences*, pp. 272.

Uno, T. et al. "Structure of 5,5-diphenylhydantoin-1-(4-bromophenyl)-4-dimethylamino-2,3-dimethyl-3-pyrazolin-5-one (1:1)" *Acta Cryst.*, 1980, pp. 2794-2796, vol. B36.

Urbina, J. et al. "Supramolecular design of inorganic/organic networks using flexible ligands with self-complementary hydrogen bonds (Abstract)" 38th Midwest Regional Meeting of the American Chemical Society in Columbia, MO., Nov. 5-7, 2003, published by the American Chemical Society, Washington, D.C.

Van Roey, P. et al. "Structure of cis-1-{[4-(1-imidazolylmethyl) cyclohexyl] methyl} imidazole-succinic acid complex" *Acta Cryst.*, 1991, pp. 1015-1018, vol. C47.

Van Roey, P. et al. "Structure-activity studies and molecular structures of CGS 16949A and 1320B" *J. Enzyme Inhibition*, 1991, pp. 119-132, vol. 5.

Villa, L. A. et al. "Central nervous system paracoccidioidomycosis. Report of a case successfully treated with itraconazol" *Rev. Inst. Med. Trop. S. Paulo*, Jul.-Aug. 2000, pp. 231-234, vol. 42, No. 4.

Vippagunta, S. R. et al. "Crystalline solids" *Advanced Drug Delivery Reviews*, 2001, pp. 3-26, vol. 48.

Vishweshwar, P. et al. "Crystal engineering of pharmaceutical co-crystals from polymorphic active pharmaceutical ingredients" *Chem. Commun.*, 2005, pp. 4601-4603.

Vishweshwar, P. et al. "Molecular complexes of homologous alkanedicarboxylic acids with isonicotinamide: X-ray crystal structures, hydrogen bond synthons, and melting point alternation" *Dotal Growth & Design*, 2003, pp. 783-790, vol. 3, No. 5.

Vishweshwar, P. et al. "Recurrence of carboxylic acid-pyridine supramolecular synthon in the crystal structures of some pyrazinecarboxylic acids" *J. Org. Chem.*, 2002, pp. 556-565, vol. 67.

Vishweshwar, P. et al. "Supramolecular synthons based on N—H•••N and C—H•••0 hydrogen bonds. Crystal engineering of a helical structure with 5,5-diethylbarbituric acid" *Chem. Commun.*, 2002, pp. 1830-1831.

(56) References Cited

OTHER PUBLICATIONS

Vishweshwar, P. et al. "Supramolecular synthons in phenol-isonicotinamide adducts" *Cryst Eng. Comm.* 2003, pp. 164-168, vol. 5, No. 31.

Voet, D. et al. "Barbiturates and adenine derivatives. Molecular structure of a hydrogen-bonded complex" *Journal of the American Chemical Society*, Aug. 9, 1972, pp. 5888-5891, vol. 94, No. 16.

Voet, D. et al. "The crystal and molecular structure of the intermolecular complex 9-ethyladenine-5, 5-diethylbarbituric acid" *Journal of the American Chemical Society*, Nov. 15, 1972, pp. 8213-8222, vol. 94, No. 23.

Voet, D. et al. "The structure of an intermolecular complex between cytosine and 5-fluorouracil" *Journal of the American Chemical Society*, May 21, 1969, pp. 3069-3075, vol. 91, No. 11.

Walsh, R.D.B. et al. " Crystal Engineering of the composition of pharmaceutical phases". *Chem. Commun.*, 2003, pp. 186-187.

Wang, A. et al. "Crystal structure of 1:1 complex of barbital with 1-methylimidazole" *Journal of Pharmaceutical Sciences*, Mar. 1979, pp. 361-363, vol. 68, No. 3.

Weber, E. et al. "Synthesis of new Schiff bases: reaction of monofluorobenzaldehydes with 3-aminosulfolane hydrochloride (Abstract)" 216th ACS National Meeting in Boston, MA., Aug. 23-27, 1998, published by the American Chemical Society, Washington, D.C.

Weissbuch, I. et al. "Crystal morphology control with tailor-made additives; a stereochemical approach" *Advances in Crystal Growth Research*, 2001, pp. 381-400.

Weissbuch, I. et al. "Understanding and Control of Nucleation, Growth, Habit, Dissolution and Structure of Two- and Three-Dimensional Crystals Using 'Tailor-Made' Auxiliaries" *Acta Cryst.*, 1995, B51:115-148.

West, A. R., "Solid Solutions" In: *Solid State Chemistry and its Applications*, 1988, p. 358, p. 365, Wiley, NY.

Wheatley, P.J., "The Crystal and Molecular Structure of Aspirin," *J. Chem. Soc.*, 1964, pp. 6036-6048.

Wiedenfeld, H. et al. "Solubilization of aminophenazone" *Arch. Pharm.*, 1982, pp. 633-641, vol. 315.

Wiedenfeld, H. et al. "The crystal structure of the theophylline-urea complex" *Arch. Pharm.*, 1986, pp. 654-659, vol. 319.

Wood, R. A. et at "2,5-O-methylene-D-mannitol sodium-chloride, $C_7H_{14}O_6 \cdot NaCl$" *Cryst. Struct. Comm.*, 1976, 207-210, vol. 5.

Wunderlich, H.F. et al. "The Derivatives of carbamazepine with ammonium halogenides and formamide" *Pharmazie*, 1991,46(7):507-509.

Xu, J. et al. "Effect of composition distribution on miscibility and co-crystallization phenomena in the blends of low density polyethylene with conventional and metallocene-based ethylene-butene copolymers" *Polymer*, 2001, pp. 3867-3874, vol. 42.

Yadav, A.V. et al. "Co-crystals: A novel approach to modify physicochemical properties of active pharmaceutical ingredients" *Indian Journal of Pharmaceutical Sciences* 2009, 71(4):359-370.

Yoo, J. et at "Cocrystallization of a dinuclear platinum complex as a monomer and a one-dimensional polymer" *Polyhedron*, 2002, pp. 715-719, vol. 21.

Zaitu, S. et al. "1:1 Molecular complex of theophylline and p-nitroaniline" *Acta Cryst.*, 1995, pp. 2390-2392, vol. C51.

Zaitu, S. et al. "A 2:1 molecular complex of theophylline and 5-fluorouracil as the monohydrate" *Acta Cryst.*, 1995, pp. 1857-1859, vol. C51.

Zaman, M. B. et al. "Crystal Engineering Using Anilic Acids and Dipyridyl Compounds through a New Supramolecular Synthon" *J. Org. Chem.*, 2001, pp. 5987-5995, vol. 66.

Zaman, M. B. et at "Linear hydrogen-bonded molecular tapes in the cocrystals of squaric acid with 4,4'-dipyridylacetylene and 1,2-bis(4-pyridyl) ethylene" *Acta Cryst.*, 2001, pp. 621-624, vol. C57.

Zaman, M.B. et al. "Crystal Engineering Using Anilic Acids and Dipyridyl Compounds through a New Supramolecular Synthon" *J. Org. Chem.*, 2001, 66:5987-5995.

Zaworotko, M. J. "Crystal Engineering of Diamondoid Networks", *Chem. Soc. Rev.*, 1994, pp. 283-288, vol. 23.

Zaworotko, Michael J., "Binary Crystals by Design," Abstracts of Papers, 23rd ACS National Meeting, Orlando, FL, United States, Apr. 7-11, 2002, IEC-030.

Zerkowski, J. et al. "Design of organic structures in the solid state: hydrogen-bonded molecular "tapes"[1]" *J. Am. Chem. Soc.*, 1990, pp. 9025-9026, vol. 112.

Zerkowski, J. et al. "Design of organic structures in the solid state: molecular tapes based on the network of hydrogen bonds present in the cyanuric acid•melamine complex" *J. Am. Chem. Soc.*, 1994, pp. 2382-2391, vol. 116.

Zerkowski, J. et al. "Investigations into the robustness of secondary and tertiary architecture of hydrogen-bonded crystalline tapes" *Chem. Mater*, 1994, pp. 1250-1257, vol. 6.

Zerkowski, J. et al. "New varieties of crystalline architecture produced by small changes in molecular structure in tape complexes of melamines and barbiturates" *J. Am. Chem. Soc.*, 1994, pp. 4305-4315, vol. 116.

Zerkowski, J. et al. "Polymorphic packing arrangements in a class of engineered organic crystals" Chem. Mater., 1997, pp. 1933-1941, vol. 9.

Zerkowski, J. et al. "Solid-state structures of "Rosette" and "Crinkled Tape" motifs derived from the cyanuric acid-melamine lattice" *J. Am. Chem. Soc.*, 1992, pp. 5473-5475, vol. 114.

Zerkowski, J. et al. "Steric control of secondary, solid-state architecture in 1:1 complexes of melamines and barbiturates that crystallize as crinkled tapes" *J. Am. Chem. Soc.*, 1994, pp. 4298-4304, vol. 116.

Zhang, R. et al. "Atmospheric new particle formation enhanced by organic acids" *Science*, Jun. 4, 2004, pp. 1487-1490 with additional supporting online material, vol. 304.

Zhu, H. et al. "Influence of water activity in organic solvent + water mixtures on the nature of the crystallizing drug phase. 1. theophylline" *International Journal of Pharmaceutics*, 1996, pp. 151-160, vol. 135.

[No Author Listed], Specifications: Test Procedures and Acceptance Criteria for New Drug Substances and New Drug Products: Chemical Substances Q6A. ICH Harmonised Tripartite Guideline. Oct. 6, 1999; 4:46.

[No Author Listed], X-ray Diffraction. In: The United States Pharmacopeia—The National Formulary (USP #24 NF19). Jan. 2000 Chapter 941: 2005-7.

Abourahma et al., Network Hydrogen Bonding in Two New Cocrystals Sustained by [Mn(CO)3(OH)]4, a tetrahedral hydrogen bond donor. J Chem Crystallogr. Nov. 1995; 25:731-736.

Almarsson et al., The A to Z of pharmaceutical cocrystals: a decade of fast-moving new science and patents. Pharm Pat Anal. Jul. 2012;1(3):313-27. doi: 10.4155/ppa.12.29.

Bedu-Addo, Understanding Lyophilization Formulation Development. Pharmaceutical Technology. Mar. 10-18, 2004.

Berge et al., Pharmaceutical salts. J Pharm Sci. Jan. 1977;66(1):1-19.

Byrn et al., Pharmaceutical solids: a strategic approach to regulatory considerations. Pharm Res. Jul. 1995;12(7):945-54.

Duke, Handbook of Phytochemical Constituents of GRAS Herbs and Other Economic Plants, 2001, CRC Press LLC, p. 419.

Evgen'Ev et al., Selective determination of 4-aminobenzoic and 4-aminosalicylic acid derivatives in mixtures by flow-injection analysis. J Anal Chem. Jul. 2000;55(7):696-702.

Smith et al., The utility of 4-aminobenzoic acid in promotion of hydrogen bonding in crystallization processes: the structures of the cocrystals with halo and nitro substituted aromatic compounds, and the crystal structures of the adducts with 4-nitroaniline (1:1), 4-(4-nitrobenzyl)pyridine (1:2), and (4-nitrophenyl)acetic acid (1:1). J Chem Crystallogr. May 1997;27(5):307-317.

U.S. Appl. No. 10/378,956, filed Mar. 3, 2003, Michael J. Zaworotko et al.

European Search Report for Application No. EP 03711407.1 dated Nov. 22, 2006.

International Search Report for Application No. PCT/US2003/06662 dated Oct. 24, 2003.

Office Action dated Apr. 13, 2011 in U.S. Appl. No. 12/861,203.

(56) References Cited

OTHER PUBLICATIONS

Notice of Reasons for Rejection dated Oct. 8, 2009 for Japanese Application No. 2003-572946.

* cited by examiner

FIG. 7A
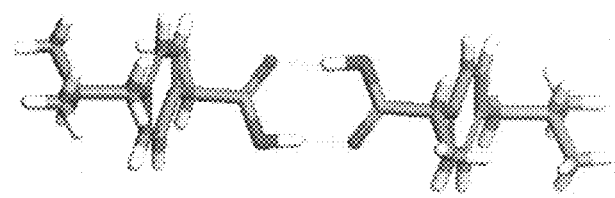
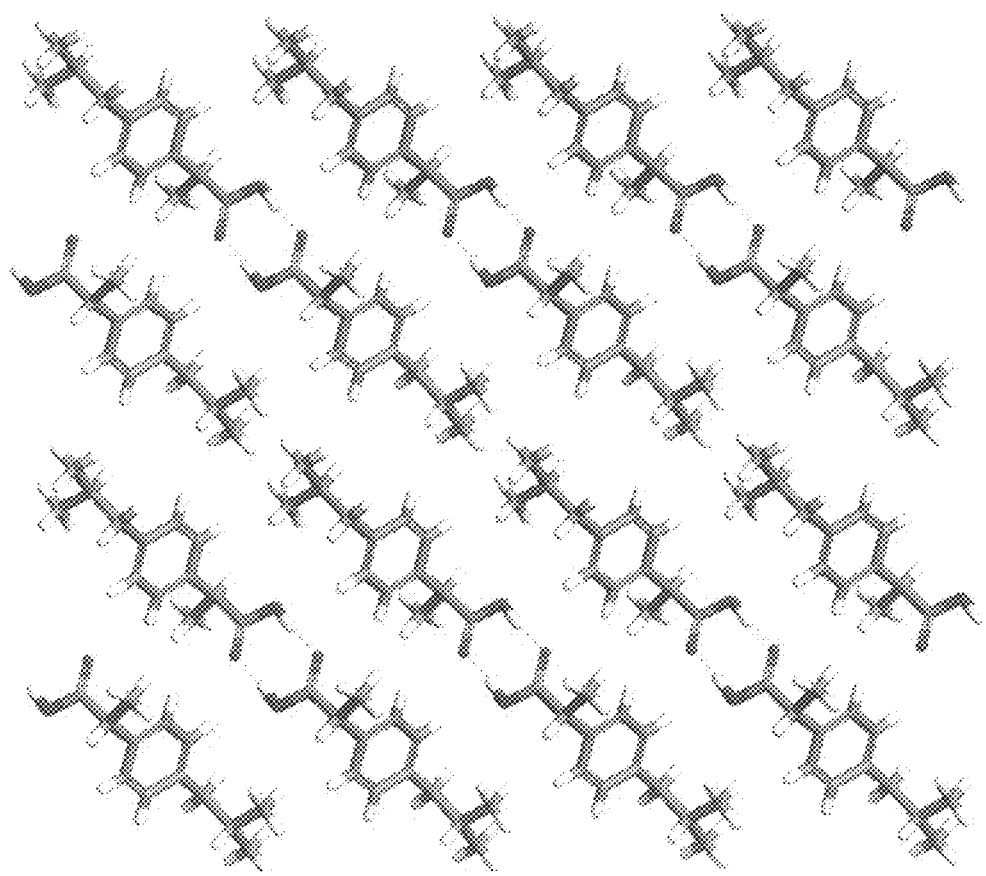
FIG. 7B

MULTIPLE-COMPONENT SOLID PHASES CONTAINING AT LEAST ONE ACTIVE PHARMACEUTICAL INGREDIENT

CROSS-REFERENCE TO RELATED APPLICATION

The present application is a continuation of U.S. application Ser. No. 10/378,956, filed Mar. 3, 2003, which is hereby incorporated by reference herein in its entirety, including any figures, tables, or drawings. U.S. application Ser. No. 10/378,956 claims the benefit of priority of U.S. Provisional Application Ser. No. 60/360,768, filed Mar. 1, 2002, which is hereby incorporated by reference herein in its entirety, including any figures, tables, or drawings.

BACKGROUND OF THE INVENTION

The last decade has witnessed tremendous advances in the understanding of, and the ability to manipulate, molecular and supramolecular assemblies (Moulton, B. et al., *Chem. Rev.*, 2001, 101:1629-1658). There are new paradigms concerning the design and synthesis of a new generation of functional materials and molecules. Such advances are a consequence of the fundamental importance of intermolecular interactions, structure and cooperativity in many aspects of molecular science, from environmental science to molecular biology, to pharmacology, to materials science. Thus, the prospects for control and manipulation of materials at the molecular level, particularly in areas related to non-covalent bonding and nanotechnology, are now truly exceptional. However, whereas crystal structure determination has been a tool used by scientists since the 1920's, crystal structure prediction remains a largely unmet goal (Ball, P. *Nature,* 1996, 381:648-650; Gavezzotti, A. *Acc. Chem. Res.,* 1994, 27:309-314). Furthermore, the existence of more than one crystalline form of a given molecular compound, typically in the form of polymorphs or solvates, represents both a problem and an opportunity (Desiraju, G. R. *Science,* 1997, 278:404-405; Bernstein, J. et al., *Angew. Chem., Int. Ed. Engl.,* 1999, 38:3441-3461). This is particularly true for the pharmaceutical industry.

Crystal engineering (Schmidt, G. M. J. *Pure Appl. Chem.,* 1971, 27:647-678; Desiraju, G. R. *Crystal Engineering: the Design of Organic Solids,* 1989, Elsevier: Amsterdam) is predicated on the assumption that crystals are de facto examples of self-assembly, i.e. crystals are comprised from a series of molecular recognition events or supramolecular synthons (Desiraju, G. R. *Angew. Chem., Int. Ed. Engl.,* 1995, 34:2311-2327). It also offers a more realizable goal than crystal structure prediction since it relies on design and allows for careful selection of substrates, i.e. substrates that are predisposed to form predictable self-assembled superstructures can be targeted for study. Furthermore, the prototypal molecules used in crystal engineering contain exo-functional molecular recognition sites and they can be complementary with themselves (self-assembly) (Boucher, E. et al., *J. Org. Chem.,* 1995, 60:1408-1412) or with other molecules (modular self-assembly) (Zaworotko, M. J. *Chem. Soc. Rev.,* 1994, 23:283-288; Sharma, C. V. K. and M. J. Zaworotko *Chem. Commun.,* 1996, 2655-2656). Coincidentally, most pharmaceutical molecules also contain exterior molecular recognition sites and, although this makes them susceptible to polymorphism and solvate formation, it also makes them attractive candidates for crystal engineering studies.

The ability of crystalline self-assemblies to be built from a bottom-up approach (Feynman, R. *Engineering and Science,* 1960, 22-36) could provide an exceptional control of the design of new phases at a molecular level. This contrasts with the current state-of-the-art: "The number of forms known for a given compound is proportional to the time and money spent in research on that compound" (McCrone, W. C. *Polymorphism in Physics and Chemistry of the Organic Solid-State,* pp. 726, Fox et al. Eds., Interscience: New York, 1965). This statement summarizes the predicaments and opportunities that one faces when dealing with a need to assert control over the composition and structure of pharmaceutical compounds in the solid state. Specifically, physical properties of crystalline solids are critically dependent on the internal arrangement of molecules or ions, making prediction of composition, crystal structure and morphology from knowledge of molecular structure a scientific challenge of the highest order. However, crystal structure prediction and even prediction of composition remains a largely unmet goal. Nonetheless, crystal engineering offers the intriguing possibility of using molecular components for their ability to impart functional characteristics (such as solubility, dissolution rate and stability) for the development of new delivery systems.

Undesirable physicochemical properties, physiological barriers, or issues of toxicity often limit the therapeutic benefit of drugs. This has motivated research in drug delivery systems for poorly soluble, poorly absorbed and labile substances. Crystalline self-assemblies represent a promising delivery modality for improving drug solubility, dissolution rate, stability and bioavailability. In addition, enhancement of drug activity can be achieved by means of inclusion complexation or molecular encapsulation. These systems offer various advantages over amorphous polymeric delivery systems both from design and stability perspectives. In this context, the existence of more than one crystalline form of a given compound, typically in the form of polymorphs or solvates, represents both a problem and an opportunity. Several factors further complicate the situation. For example, the Food and Drug Administration's (FDA's) strict purity requirements effectively mean that a particular crystalline phase of a drug must be selected and that its composition must be established. This has typically meant that a consistent X-ray powder diffraction (XPD) pattern is required (Federal Drug Administration *Fed. Regist.,* 1997, 62:62893-62894). The need to ensure that processing produces both purity and ease of processing is problematic because many drug molecules are prone to form multiple phases, and crystal size and morphology can vary for a given phase. The commercial and public image costs of not ensuring that processing is reliable and reproducible is at best very high, as demonstrated by the recent pull back and reformulation of NORVIR by ABBOTT LABORATORIES).

That XPD patterns have been relied on for quality control is convenient but is in many ways unfortunate since XPD is not as foolproof as single crystal X-ray crystallography (e.g. similar patterns can be obtained for different phases, composition is not unambiguously determined), and XPD does not determine crystal packing. Knowledge of crystal packing is important because it helps explain the solubility and composition of a particular phase and provides other valuable information. However, the materials properties of pharmaceuticals and the existence of polymorphs are generally investigated at the tail end of the drug development process.

Accordingly, it would be advantageous to provide novel crystalline phases having properties, such as melting point, solubility, dissolution rate, chemical stability, thermodynamic stability, and/or bioavailability, which are different from existing solid forms of the pharmaceutical compound upon which they are based.

BRIEF SUMMARY OF THE INVENTION

The subject invention relates to the application of the concepts of crystal engineering towards the design of new pharmaceutical phases that contain more than one molecular component.

The subject invention concerns multiple-component solids having at least one active pharmaceutical ingredient. Examples of pharmaceutical molecules that may be utilized as active pharmaceutical ingredients in the multiple-component solids of the subject invention include, but are not limited to, aspirin, one or more members of the profen series (e.g., ibuprofen and flurbiprofen), carbamazepine, phenyloin, and acetaminophen. Multiple-component solids, such as multiple-component crystals, containing these pharmaceutical ingredients and complementary molecules (hereafter referred to as "co-crystal formers") have been characterized by various techniques and can exhibit physical and/or chemical properties that are the same or different from the parent pharmaceutical ingredient as a direct result of alternative molecular recognition patterns. These novel crystalline assemblies can afford improved drug solubility, dissolution rate, stability and bioavailability.

The subject invention relates to the application of the concepts of crystal engineering towards the design of new pharmaceutical solid phases, such as multiple-component phases, using cocrystal formers that are complementary in the sense of supramolecular chemistry, i.e. they form supramolecular synthons with pharmaceutical molecules or ions. The cocrystal formers can be, but are not limited to, solvent molecules, other drug molecules, GRAS compounds, or approved food additives. Pharmaceutical molecules or ions are inherently predisposed for such crystal engineering studies since they already contain molecular recognition sites that bind selectively to biomolecules, and they are prone to supramolecular self-assembly. Examples of the groups commonly found in active pharmaceutical ingredients, and which are capable of forming supramolecular synthons include, but are not limited to, acids, amides, aliphatic nitrogen bases, unsaturated aromatic nitrogen bases (e.g. pyridines, imidazoles), amines, alcohols, halogens, sulfones, nitro groups, S-heterocyles, N-heterocycles (saturated or unsaturated), and O-heterocycles. Other examples include ethers, thioethers, thiols, esters, thioesters, thioketones, epoxides, acetonates, nitrils, oximes, and organohalides. Some of these groups can form supramolecular synthons with identical groups in similar or different molecules and are termed homosynthons, e.g. acids and amides. Other groups can form supramolecular synthons with different groups and are termed heterosynthons, e.g. acide/amide, pyridine/amide; alcohol/amine. Heterosynthons are particularly suitable for formation of multiple-component crystals whereas homosynthons can sometimes form multiple-component crystals.

In one aspect, the subject invention concerns methods for identifying complementary chemical functionalities to form a desired supramolecular synthon, wherein the method comprises the steps of evaluating the structure of an active pharmaceutical ingredient (API), which can include determining its crystal structure; determining whether the API contains chemical functionalities capable of forming supramolecular synthons with itself; identifying from a plurality of chemical functionalities that are known to form a supramolecular synthon at least one chemical functionality that will form a further supramolecular synthon to the supramolecular synthon formed by the API, wherein the identified chemical functionality is not capable of disrupting non-covalent bonding within the supramolecular synthon formed by the supramolecular synthon formed by the API, and wherein the selected chemical functionality is capable of forming a noncovalent bond to the supramolecular synthon formed by the API; and identifying co-crystal formers having chemical functionalities that are complementary with the API.

In another aspect, the subject invention concerns methods for identifying complementary chemical functionalities to form a desired supramolecular synthon, wherein the method comprises the steps of evaluating the structure of an API, which can include determining its crystal structure; determining whether the API contains chemical functionalities capable of forming supramolecular synthons with itself; identifying from a plurality of chemical functionalities that are known to form supramolecular synthons at least one functionality that will from a supramolecular synthon with the API, wherein the identified chemical functionality is capable of disrupting non-covalent bonding within the supramolecular synthon formed by the API, and wherein the selected chemical functionality is capable of forming a noncovalent bond to a complementary chemical functionality on the API; and identifying co-crystal formers having chemical functionalities that are complementary with the API. Thus, according to this method, the formation of homosynthons for the purpose of disrupting the intermolecular interactions between pharmaceutical moieties can be carried out.

In still another aspect, the subject invention concerns methods for identifying complementary chemical functionalities to form a desired supramolecular synthon, wherein the method comprises the steps of evaluating the structure of an API, which can include determining its crystal structure; determining whether the API contains chemical functionalities capable of forming supramolecular synthons with different molecules; identifying from a plurality of chemical functionalities that are known to form supramolecular synthons at least one functionality that will form a supramolecular synthons with the API; and wherein the selected chemical functionality is capable of forming a noncovalent bond to a complementary chemical functionality on the API, and identifying co-crystal formers having chemical functionalities that are complementary with the active pharmaceutical ingredient.

As indicated above, certain aspects of the subject invention can involve selecting a chemical functionality that is capable of disrupting the non-covalent bonding between identical functionalities (homosynthon) and form a non-covalent bond between different, yet complementary, functionalities (heterosynthon); selecting a plurality of molecular entities that comprise the complementary functionality (preferably GRAS compounds or approved food additives); identifying additional chemical features on the molecular entities that will not interfere with the formation of the desired supramolecular synthon and that will impart the desired physical properties to the target phase; and, optionally, preparing a new solid phase that is composed of the pharmaceutical moiety and the complementary molecular entity (such as a multiple-component phase or two component phase) by crystallization techniques comprising reactions in solvent, and/or solventless reactions, that afford crystalline materials. Optionally, the methods can further include at least one of the subsequent steps of determining the structure of the new solid phase formed; and analyzing the physical properties of the new solid phase.

The subject invention further concerns new solid phases identified or produced using the methods identified herein. The subject invention further pertains to a multiple-component phase composition comprising a solid material (phase) that is sustained by intermolecular interactions between two or more independent molecular entities, in any stoichiometric ratio, wherein at least one of the independent molecular entities is a pharmaceutical entity. The multiple-component phase composition can be, for example, a discrete supramolecular entity or a polymeric structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B show the supramolecular entity containing the synthon of pure aspirin and corresponding crystal structure, respectively. FIGS. 6C and 6D show the supramolecular entity containing the synthon and corresponding co-crystal of aspirin/4,4'-bipyridine, respectively. The pure phase (Chiari, G. et al., Acta Crystallogr., Sect B, 1981, 37:1623) of acetylsalicylic acid, has centrosymmetric carboxylic acid homodimers and crystallizes in the space group P2$_1$/c, packing in 2D polymeric sheets with hydrophobic planes.

FIGS. 7A-7D show supramolecular entities containing synthons and corresponding crystal structures of pure ibuprofen [2-(4-isobutylphenyl) propionic acid] and ibuprofen/4,4'-bipyridine. FIGS. 7A and 7B show the supramolecular entity containing the synthon of pure ibuprofen and corresponding crystal structure, respectively. FIGS. 7C and 7D show the supramolecular entity containing the synthon of ibuprofen/4,4'-bipyridine and corresponding co-crystal, respectively. The reported crystal structures of ibuprofen are racemic (McConnell, J. F. Cryst. Strucut. Commun., 1974, 3:73) and S (+) forms (Freer, A. A. et al., Acta Crystallogr., Sect C (Cr. Str. Comm), 1993, 49:1378). Both contain hydrogen bonded carboxylic acid homodimers. Racemic dimers have centers of inversion across the dimer, which crystallize in the space group P2$_1$/c. The S (+) form contains asymmetric dimers, which crystallize in the space group P2$_1$. Both crystals pack in 2-D polymeric sheets sustained by π-π stacking and hydrophobic in-layer interactions.

FIGS. 8A and 8B show the supramolecular entity containing the synthon of pure flurbiprofen and corresponding crystal structure, respectively. FIGS. 5C and 5D show the supramolecular synthon of flurbiprofen/4,4'-bipyridine and corresponding co-crystal, respectively. Flurbiprofen has one reported pure form (Flippen, J. L. et al., Acta Crystallogr., Sect. B, 1975, 31:926) and contain hydrogen bonded carboxylic acid homodimers with a center of inversion and crystallizes in the P-l space group. 2-D polymeric sheets are formed through π-π and hydrophobic interactions from the phenyl rings.

DETAILED DISCLOSURE OF THE INVENTION

Figure 1:
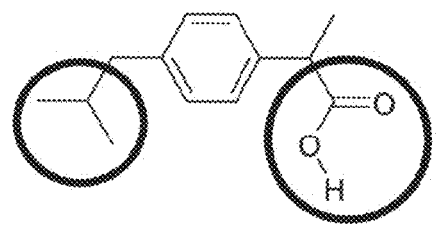
FIG. 1 shows the chemical structure of ibuprofen. The external functionalities are an isopropyl group (encircled on the left, in cyan) and a carboxylic acid (encircled on the right, in magenta).

The subject invention relates to the application of the concepts of crystal engineering towards the design of new multiple-component solid phases, such as multiple-component crystals, having at least one active pharmaceutical component. Examples of multiple-component crystals of the subject invention include, but are not limited to, acetominophen/4,4'-bipyridine/water, phenyloin/pyridone, aspirin/4,4'-bipyridine, ibuprofen/4,4'-dipyridyl, flurbiprofen/4,4'-dipyridine, flurbiprofen/trans-1,2-bis(4-pyridyl)ethylene, carbamazepine/p-phthalaldehyde, carbamazepine/nicotinamide (GRAs), carbamazepine/saccharin (GRAs), carbamazepine/2,6-pyridinedicarboxylic acid, carbamazepine/5-nitroisophthalic acid, carbamazepine/acetic acid, carbamazepine/1,3,5,7-adamantanetetracarboxylic acid, carbamazepine/benzoquinone, carbamazepine/butyric acid, carbamazepine/dimethyl sulfoxide (DMSO), carbamazepine/formamide, carbamazepine/formic acid, and carbamazepine/tremesic acid, which have been characterized by various techniques and exhibit physical properties different from the parent pharmaceutical ingredient as a direct result of hydrogen bonding interaction. These crystalline assemblies can afford improved drug solubility, dissolution rate, stability and bioavailability, for example.

In one aspect, the subject invention concerns a method for identifying complementary chemical functionalities to form a desired supramolecular synthon, wherein the method comprises the steps of evaluating the structure of an active pharmaceutical ingredient (API), which can include determining its crystal structure; determining whether the API contains chemical functionalities capable of forming supramolecular synthons with itself; identifying from a plurality of chemical functionalities that are known to form a supramolecular synthon at least one chemical functionality that will form a further supramolecular synthon to the supramolecular synthon formed by the API, wherein the identified chemical functionality is not capable of disrupting non-covalent bonding within the supramolecular synthon formed by the supramolecular synthon formed by the API, and wherein the selected chemical functionality is capable of forming a noncovalent bond to the supramolecular synthon formed by the API; and identifying co-crystal formers having chemical functionalities that are complementary with the API.

In another aspect, the subject invention concerns methods for identifying complementary chemical functionalities to form a desired supramolecular synthon, wherein the method comprise the steps of evaluating the structure of an API, which can include determining its crystal structure; determining whether the API contains chemical functionalities capable of forming supramolecular synthons with itself; identifying from a plurality of chemical functionalities that are known to form supramolecular synthons at least one functionality that will form a supramolecular synthon with the API, wherein the identified chemical functionality is capable of disrupting non-covalent bonding within the supramolecular synthon formed by the API, and wherein the selected chemical functionality is capable of forming a noncovalent bond to a complementary chemical functionality on the API; and identifying co-crystal formers having chemical functionalities that are complementary with the API. Thus, according to this method, the formation of homosynthons for the purpose of disrupting the intermolecular interactions between pharmaceutical moieties can be carried out.

In still another aspect, the subject invention concerns methods for identifying complementary chemical functionalities to form a desired supramolecular synthon, wherein the method comprises the steps of evaluating the structure of an API, which can include determining its crystal structure; determining whether the API contains chemical functionalities capable of forming supramolecular synthons with different molecules; identifying from a plurality of chemical functionalities that are known to form supramolecular synthons at least one functionality that will form a supramolecular synthons with the API, and wherein the selected chemical functionality is capable of forming a noncovalent bond to a complementary chemical functionality on the API; and identifying co-crystal formers having chemical functionalities that are complementary with the active pharmaceutical ingredient.

In each of the three aspects of the methods described above, the methods can further comprise preparing a multiple-component solid phase composition composed of the API and at least one of the identified co-crystal formers. The identified co-crystal formers can be, for example, a different API, a GRAS compound, a food additive, a low toxicity organic, or a metal-organic complex. Various methods can be utilized for preparing the multiple-component solid phase composition, such as crystallization from solution, cooling the melt, sublimation and grinding. In addition, the methods of the subject invention can further comprise either or both of the following steps: determining the structure of the new multiple-component solid phase composition, and analyzing the physical and/or chemical properties of the new multiple-component solid phase composition.

The subject invention further concerns new solid phase identified or produced using the methods identified herein. The subject invention further pertains to a multiple-component phase composition comprising a solid material (phase) that is sustained by intermolecular interactions between two or more independent molecular entities, in any stoichiometric ratio, wherein at least one of the independent molecular entities is a pharmaceutical entity. The multiple-component phase composition of the subject invention can be, for example, a discrete supramolecular entity or a polymeric structure. The multiple-component phase compositions of the subject invention can have properties, such as melting point, solubility, dissolution rate, stability, and/or bioavailability, which are different from the pharmaceutical compound, or compounds, upon which they are based.

By way of example, the external functionalities of ibuprofen are an isopropyl group and a carboxylic acid, as shown in FIG. 1.

Figure 2:
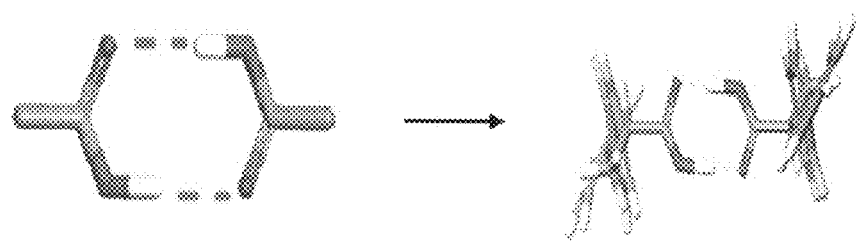
FIG. 2 shows a scheme with the synthon of pure ibuprofen on the left and the supramolecular entity containing the synthon on the right, demonstrating that pure phases of ibuprofen are sustained by carboxylic acid-carboxylic acid interactions. The standard chemical color correlation appears in all the figures where color is utilized (e.g. red=oxygen; white=oxygen; dark blue=nitrogen; light blue=fluorene; yellow=sulfur).

Using the methods of the subject invention, it has been determined that this interaction can be disrupted by co-crystallization with an aromatic amine, as shown in FIG. 2.

Figure 3:
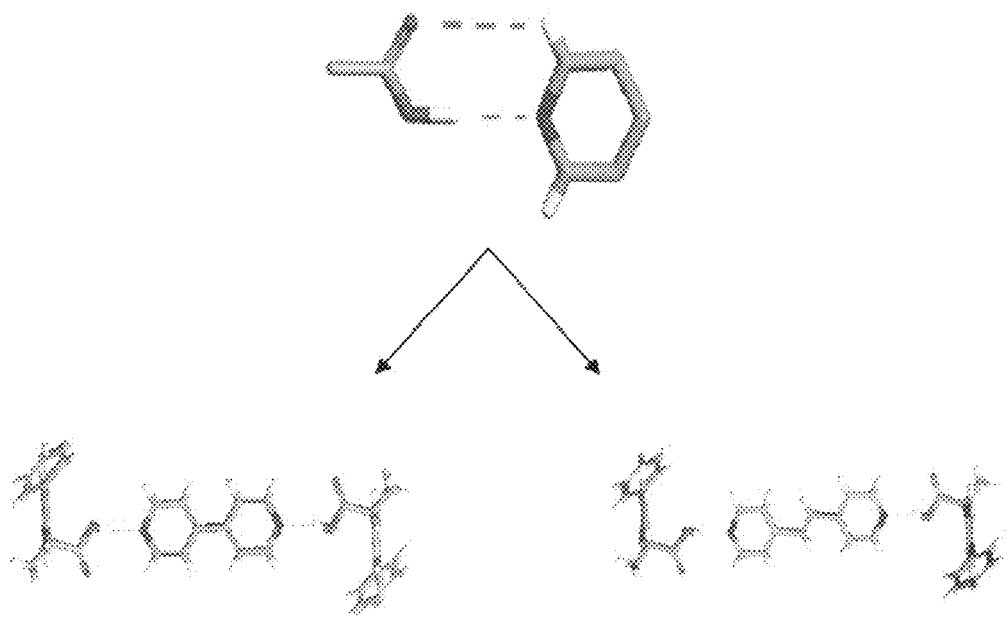
FIG. 3 shows a scheme wherein the carboxylic acid-carboxylic acid interactions of ibuprofen are disrupted by co-crystallization with an aromatic amine. Specifically, by using diamines, 2:1 multiple-component phases are produced.
Figure 13A:
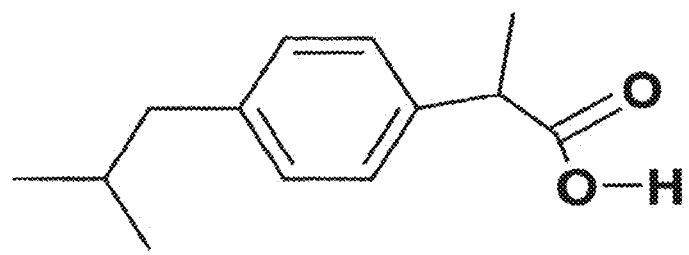
FIGS. 13A-13C show the chemical structures of ibuprofen, flurbiprofen, and aspirin, respectively.
Figure 13B:
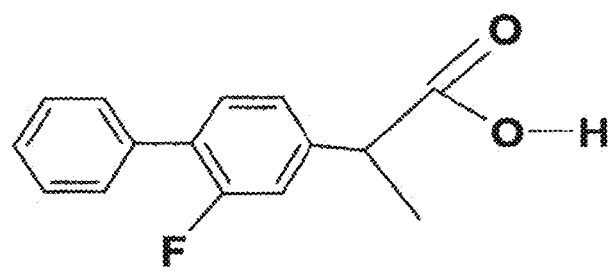
Figure 13C:
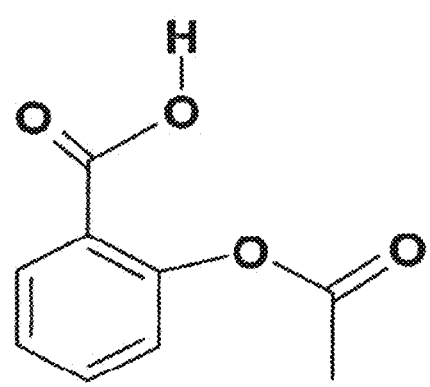

Specifically, by using diamines, 2:1 binary phases of ibuprofen have been prepared, as shown in FIG. 3, as well as other phases exemplified herein. Therefore, the methods of the subject invention can be used to identify complementary chemical functionalities and produce multiple-component phase compositions for a variety of pharmaceuticals, including those pharmaceutical compounds with structures very different those of ibuprofen, flurbiprofen, and aspirin, which are shown in FIGS. 13A-13C, respectively.

As used herein, the term "multiple-component phase" refers to any solid material (phase) that is sustained by intermolecular interactions between at least two independent molecular entities, in any stoichiometric ratio, wherein at least one of the independent molecular entities is a pharmaceutical entity. Examples of intermolecular interactions include, but are not limited to one or more of the following: hydrogen bonding (weak and/or strong), dipole interactions (induced and/or non-induced), stacking interactions, hydrophobic interactions, and other inter-static interactions. Each independent molecular entity can be a discrete supramolecular entity or polymeric structure, for example. Preferably, one or more of the independent molecular entities comprises a molecule of a "GRAS" compound, that is, a compound "Generally Regarded as Safe by the Food and Drug Administration (FDA)". More preferably, the GRAS compound is a non-pharmaceutical entity.

The terms "pharmaceutical entity," pharmaceutical moiety", "pharmaceutical component", "pharmaceutical molecule", and "active pharmaceutical ingredient (API)", and grammatical variations thereof, are used interchangeably herein to refer to any biologically active moiety having a therapeutic effect on a human or animal suffering from a given pathological condition, when administered in a given concentration. Therefore, pharmaceutical entities useful as the active pharmaceutical ingredients in the multiple phase solids of the subject invention can be administered to a human or animal, which may or may not be suffering from a pathological condition, and the pharmaceutical entity can have a prophylactive effect, a palliative effect, and/or be a curative intervention. As used herein, these pharmaceutical entities are intended to include pharmaceutically acceptable salts of a given pharmaceutical entity that retain all or a portion of their pharmaceutical activity. Pharmaceutical molecules or ions are inherently predisposed for such crystal engineering studies since they already contain molecular recognition sites that bind selectively to biomolecules, and they are prone to supramolecular self-assembly. Examples of the groups commonly found in active pharmaceutical ingredients, and which are capable of forming supramolecular synthons include, but are not limited to, acids, amides, aliphatic nitrogen bases, unsaturated aromatic nitrogen bases (e.g. pyridines, imidazoles), amines, alcohols, halogens, sulfones, nitro groups, S-heterocyles, N-heterocycles (saturated or unsaturated), and O-heterocycles. Other examples include ethers, thioethers, thiols, esters, thioesters, thioketones, epoxides, acetonates, nitrils, oximes, and organohalides. Some of these groups can form supramolecular synthons with identical groups in similar or different molecules and are termed homosynthons, e.g. acids and amides. Other groups can form supramolecular synthons with different groups and are termed heterosynthons, e.g., acid/amide; pyridine/amide; alcohol/amine. Heterosynthons are particularly suitable for formation of multiple-component crystals whereas homosynthons can sometimes form multiple-component crystals.

As used herein, the term "supramolecular synthon" refers to the sum of the components of a multi-component non-covalent interaction, wherein the non-covalent interaction contributes to the formation of a discrete supramolecular entity or polymeric structure, wherein each component is a chemical functionality. A supramolecular synthon can be a dimer, trimer, or n-mer, for example.

The multiple-component phase compositions can be formulated according to known methods for preparing pharmaceutically useful compositions. Such pharmaceutical compositions can be adapted for various forms of administration, such as oral, parenteral, nasal, topical, transdermal, etc. The multiple-component phase solids of the subject invention can be made into solutions or amorphous compounds, as injections, pills, or inhalants, for example. Optionally, the pharmaceutical compositions can include a pharmaceutically acceptable carrier or diluent. Formulations are described in a number of sources which are well known and readily available to those skilled in the art. For example, *Remington's Pharmaceutical Science* (Martin E W [1995] Eastone Pa., Mack Publishing Company, 19th ed.) a) describes formulations that can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, or tablets of the multiple-component phase compositions of the subject invention, for example. It should be understood that in addition to the ingredients particularly mentioned above, the formulations of the subject invention can include other agents conventional in the art having regard to the type of formulation in question.

In terms of superstructure, three general types of compounds generated by interaction of a drug molecule with another molecule include: (1) multiple-component compounds, in which superstructure is generated by two or more molecules, both of which are integral components of the network and complementary; (2) clathrate inclusion compounds, in which the compounds' superstructure is generated by self-assembly of one or more molecules and a guest molecules is enclosed within the superstructure; and (3) porous inclusion compounds, in which the superstructure is open framework in nature.

The subject invention concerns multiple-component compositions, and it is demonstrated herein that the concepts of crystal engineering and supramolecular synthons can be applied to prepare a wide range of novel pharmaceutical materials that are based on rational design. Therefore, the binary compounds of the subject invention can be generated in such a fashion that they have desirable composition, structure and properties. More specifically, an issue that is particularly relevant to pharmaceutical compositions of matter and processing is addressed by the subject invention: the diversity of compositions, superstructures and solubilities that can be generated when drug molecules form binary phases with complementary molecules. Binary phases involving the following drugs are exemplified herein: aspirin, acetaminophen, ibuprofen (and related compounds), phenyloin and carbamazepine and appropriate molecular additives. These novel phases include both "multiple-component phases" that illustrate the concept of crystal engineering and multiple-component phases that incorporate pharmaceuticals with "GRAS" compounds, that is, compounds "Generally Regarded as Safe by the FDA", and/or food additives.

In the context of organic and pharmaceutical solids, the subject invention addresses these issues by demonstrating that crystal engineering offers a paradigm for the supramolecular synthesis (Chang, Y. L. et al., *J. Am. Chem. Soc.*, 1993, 115:5991-6000) of a wide range of new multiple component phases that have predetermined compositions and, in some instances, predetermined topology. Such an ability to build hierarchical structures from molecular or supramolecular modules facilitates precise control of structure and function of solid phases. These multiple-component phases have the following advantages over single component phases and traditional multiple-component phases (solid dispersions): high thermodynamic stability (thereby reducing problems associated with solid phase transformations), modified bioavailability (finely tunable solubility and delivery), and enhanced processability (crystal morphology, mechanical properties, hygroscopicity).

The subject invention has the following implications from a scientific perspective: (a) protocols are now available for the rational design of a new generation of pharmaceutical phases that contain at least two components that are sustained by supramolecular synthons; (b) correlation of structure and function of the new pharmaceutical phases via characterization of structure, crystal energy, solubility, dissolution rate, and stability is now possible; and (c) a new range of novel phases for the treatment of pathological conditions in humans and animals are available.

The subject invention extends the state-of-the-art in at least three ways: (1) by generating a rational, supramolecular strategy for the design of novel, multiple component crystalline phases; (2) by extending this strategy to pharmaceutical phases; and (3) by using this strategy to control the delivery properties and stability of pharmaceutical compounds.

The following pages describe examples of multiple component crystalline phases that have been characterized using single crystal X-ray crystallography and structure-sensitive analytical techniques: FT-IR, XRPD, DSC, TGA. They represent prototypal examples of the invention as they are all based upon pharmaceutical molecules that are inherently predisposed to form supramolecular synthons with other complementary functional groups. They were chosen for study because of well-known limitations in their solubility/bioavailibility. In each example, the nature of the pure phase is discussed and it is sustained by a supramolecular homosynthon (self-complementary functionalities). The multiple-component phases prepared confirm the ability to persistently and rationally disrupt the homosynthon by judicious choice of a second molecular component that is predisposed to form a supramolecular heterosynthon. That these new solid phases will have different solubility profiles than their pure phases is to be expected. Examples designated as GRAS are those in which second a component that is "Generally Regarded as Safe by the FDA" was used.

EXAMPLE 1

Multi-Component Crystal of Acetaminophen:
Acetominophen/4,4'-Bipyridine/Water (1:1:1
Stoichiometry)

Figure 4A:
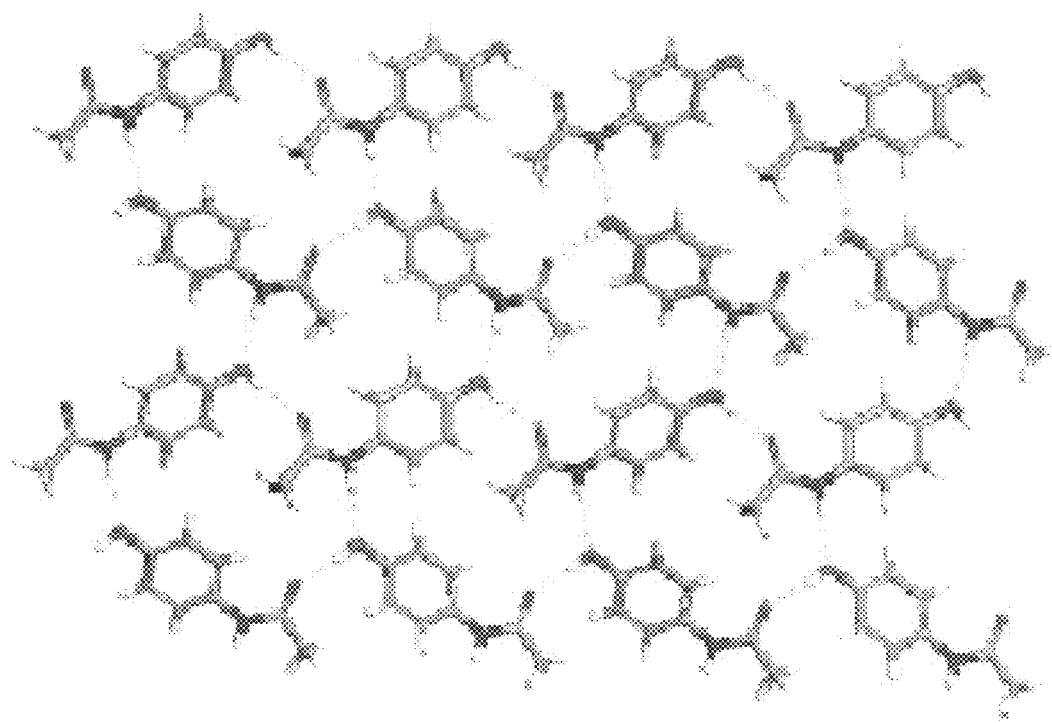
FIGS. 4A-4B show an acetaminophen 1-D polymeric chain and an acetaminophen/4,4'-bipyridine/water crystal, respectively. Reported forms are monoclinic (P2$_1$/n) (Haisa, M. et al., Acta Crystallogr., Sect B, 1974, 30:2510) and orthorhombic (Pbca) (Haisa, M. et al., Acta Crystallogr., Sect B, 1976, 32:1283) polymorphs. The monoclinic polymorph forms pleated sheets with all hydrogen bonding donors and acceptors interacting. The orthorhombic polymorph forms form 1-D polymeric chains with all donors and acceptors interacting.
Figure 4B:
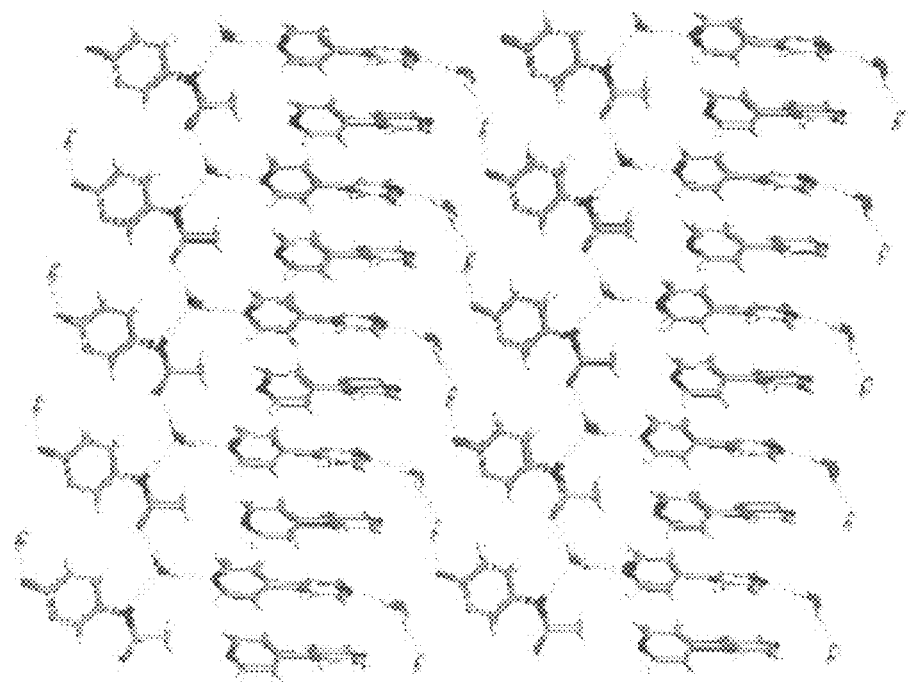

50 mg (0.3307 mmol) acetaminophen and 52 mg (0.3329 mmol) 4,4'-bipyridine were dissolved in hot water and allowed to stand. Slow evaporation yielded colorless needles of a 1:1:1 acetaminophen/4,4'-bipyridine/water co-crystal, as shown in FIG. 4B.

Crystal data: (Bruker SMART-APEX CCD Diffractometer). $C_{36}H_{44}N_2O_4$, M=339.84, triclinic, space group P$\bar{1}$; a=7.0534(8), b=9.5955(12), c=19.3649(2) Å, α=86.326(2), β=80.291(2), γ=88.880(2)°, U=1308.1(3) Å$^3$, T=200(2) K, Z=2, μ(Mo-Kα)=0.090 mm$^{-1}$, $D_c$=1.294 Mg/m$^3$, λ=0.71073 Å$^3$, F(000)=537, 2θ$_{max}$=25.02°; 6289 reflections measured, 4481 unique ($R_{int}$=0.0261). Final residuals for 344 parameters were $R_1$=0.0751, $wR_2$=0.2082 for I>2σ(I), and $R_1$=0.1119, $wR_2$=0.2377 for all 4481 data.

Crystal packing: The co-crystals contain bilayered sheets in which water molecules act as a hydrogen bonded bridge between the network bipyridine moieties and the acetaminophen. Bipyridine guests are sustained by π-π stacking interactions between two network bipyridines. The layers stack via π-π interactions between the phenyl groups of the acetaminophen moieties.

Differential Scanning calorimetry: (TA Instruments 2920 DSC), 57.77° C. (endotherm); m.p.=58-60° C. (MEL-TEMP); (acetaminophen m.p.=169° C., 4,4'-bipyridine m.p.=111-114° C.).

EXAMPLE 2

Multi-Component Crystal of Phenyloin:
Phenyloin/Pyridine (1:1 Stoichiometry)

Figure 5A:
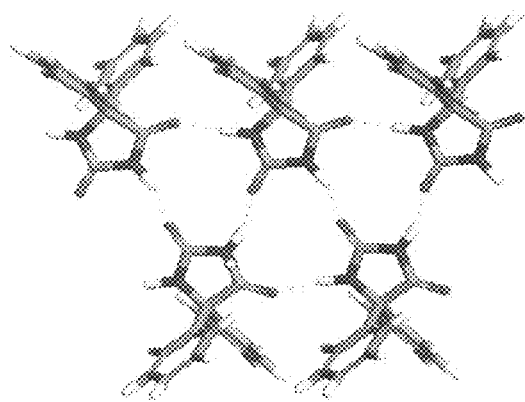
FIGS. 5A-5B show pure phenyloin and a phenyloin/pyridone co-crystal, respectively. Phenyloin has one known pure form (Carmerman, A. et al., Acta Crystallogr., Sect B, 1971, 27:2207). The crystal structure reveals a two dimensional network formed by hydrogen bonds between both the carbonyl and 2° amine.
Figure 5B:
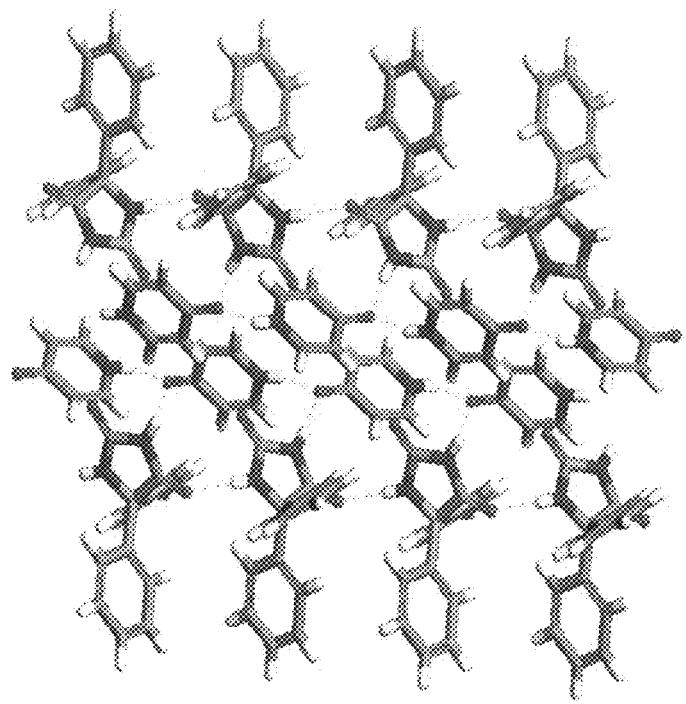

28 mg (0.1109 mmol) phenyloin and 11 mg (0.1156 mmol) 4-hydroxypyridone were dissolved in 2 mL acetone and 1 mL ethanol with heating and stirring. Slow evaporation yielded colorless needles of a 1:1 phenyloin/pyridone co-crystal, as shown in FIG. 5B.

Crystal data: (Bruker SMART-APEX CCD Diffractometer), $C_{20}H_{17}N_3O_3$, M=347.37, monoclinic P2$_1$/c; a=16.6583 (19), b=8.8478(10), c=11.9546(14) Å, β=96.618(2)°, U=1750.2(3) Å$^3$, T=200(2) K, Z=4, μ(Mo-Kα)=0.091 mm$^{-1}$, $D_c$=1.318 Mg/m$^3$, λ=0.71073 Å$^3$, F(000)=728, 2θ$_{max}$=56.60°; 10605 reflections measured, 4154 unique ($R_{int}$=0.0313). Final residuals for 247 parameters were $R_1$=0.0560, $wR_2$=0.1356 for I>2σ(I), and $R_1$=0.0816, $wR_2$=0.1559 for all 4154 data.

Crystal packing: The co-crystal is sustained by hydrogen bonding of adjacent phentoin molecules between the carbonyl and the amine closest to the tetrahedral carbon, and by hydrogen bonding between pyridone carbonyl functionalities and the amine not involved in phenyloin-phenyloin interactions. The pyridone carbonyl also hydrogen bonds with adjacent pyridone molecules forming a one-dimensional network.

Infrared Spectroscopy: (Nicolet Avatar 320 FTIR), characteristic peaks for the co-crystal were identified as: 2° amine found at 3311 cm$^{-1}$, carbonyl (ketone) found at 1711 cm$^{-1}$, olephin peak found at 1390 cm$^{-1}$.

Differential Scanning calorimetry: (TA Instruments 2920 DSC), 233.39° C. (endotherm) and 271.33° C. (endotherm); m.p.=231-233° C. (MEL-TEMP); (phenyloin m.p.=295° C., pyridone m.p.=148° C.).

Thermogravimetric Analysis: (TA Instruments 2950 Hi-Resolution TGA), a 29.09% weight loss starting at 192.80° C., 48.72% weight loss starting at 238.27° C., and 18.38% loss starting at 260.17° C. followed by complete decomposition.

X-ray powder diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. XRPD: Showed analogous peaks to the simulated XRPD derived from the single crystal data. In all cases of recrystallization and solid state reaction, experimental (calculated): 5.2 (5.3); 11.1 (11.3); 15.1 (15.2); 16.2 (16.4); 16.7 (17.0); 17.8 (17.9); 19.4 (19.4); 19.8 (19.7); 20.3 (20.1); 21.2 (21.4); 23.3 (23.7); 26.1 (26.4); 26.4 (26.6); 27.3 (27.6); 29.5 (29.9).

EXAMPLE 3

Multi-Component Crystal of Aspirin
(Acetylsalicylic Acid): Aspirin/4,4'-Bipyridine (2:1 Stoichiometry)

Figure 6A:
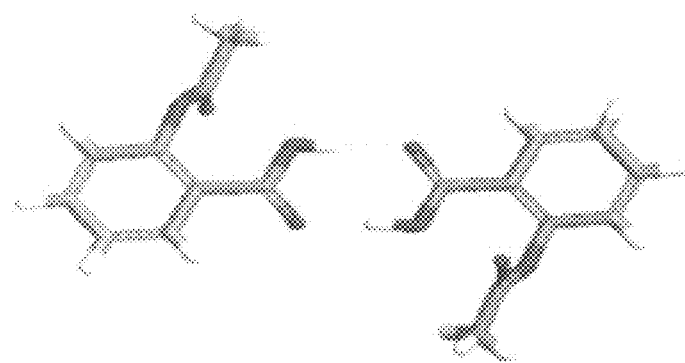
FIGS. 6A-6D show supramolecular entities containing synthons and corresponding crystal structures of pure aspirin and aspirin/4,4'-bipyridine.
Figure 6B:
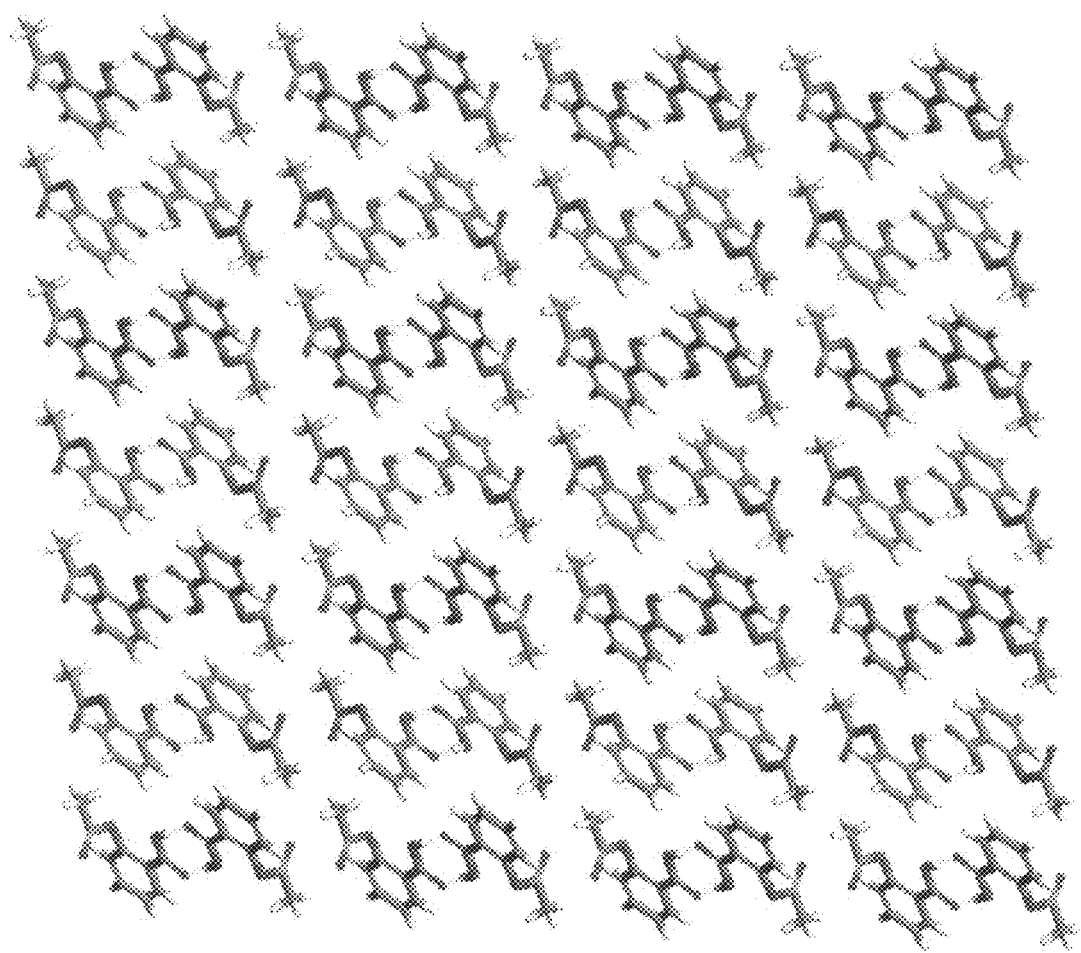
Figure 6C:
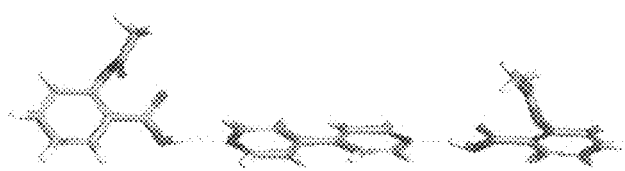
Figure 6D:
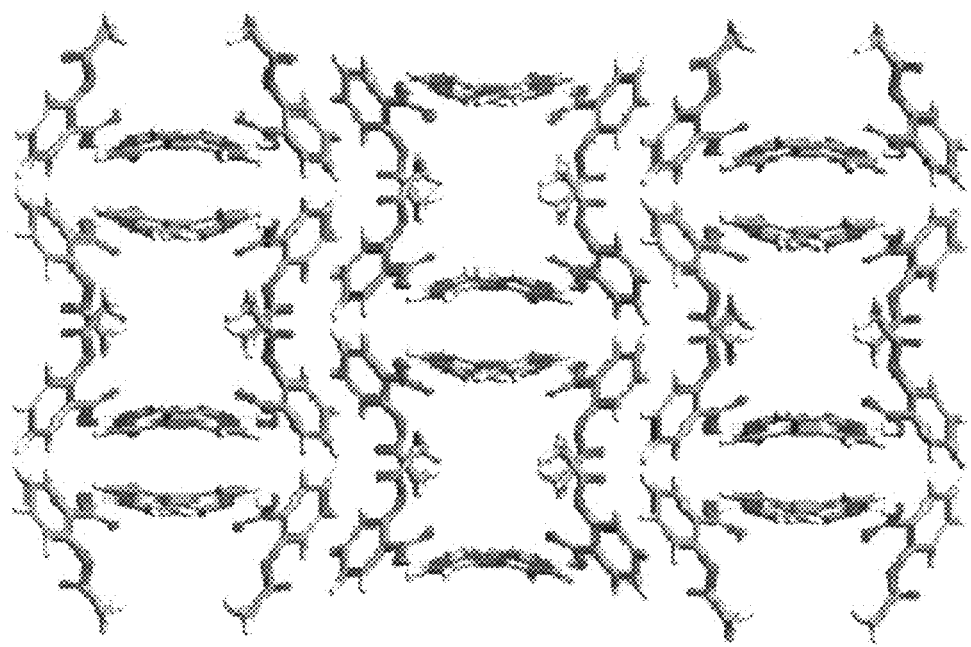

50 mg (0.2775 mmol) aspirin and 22 mg (0.1388 mmol) 4,4'-bipyridine were dissolved in 4 mL hexane. 8 mL ether was added to the solution and allowed to stand for one hour, yielding colorless needles of a 2:1 aspirin/4,4'-bipyridine co-crystal, as shown in FIG. 6D. Alternatively, aspirin/4,4'-bipyridine (2:1 stoichiometry) can be made by grinding the solid ingredients in a pestle and mortar.

Crystal data: (Bruker SMART-APEX CCD Diffractometer), $C_{28}H_{24}N_2O_8$, M=516.49, orthorhombic Pbcn; a=28.831 (3), b=11.3861(12), c=8.4144(9) Å, U=2762.2(5) Å$^3$, T=173 (2) K, Z=4, μ(Mo-Kα)=0.092 mm$^{-1}$, $D_c$=1.242 Mg/m$^3$, λ=0.71073 Å$^3$, F(000)=1080, $2θ_{max}$=25.02°; 12431 reflections measured, 2433 unique ($R_{int}$=0.0419). Final residuals for 202 parameters were $R_1$=0.0419, $wR_2$=0.1358 for I>2σ (I), and $R_1$=0.0541, $wR_2$=0.1482 for all 2433 data.

Crystal packing: The co-crystal contains the carboxylic acid-pyridine heterodimer that crystallizes in the Pbcn space group. The structure is an inclusion compound containing disordered solvent in the channels. In addition to the dominant hydrogen bonding interaction of the heterodimer, π-π stacking of the bipyridine and phenyl groups of the aspirin and hydrophobic interactions contribute to the overall packing interactions.

Infrared Spectroscopy: (Nicolet Avatar 320 FTIR), characteristic (—COOH) peak at 1679 cm$^{-1}$ was shifted up and less intense at 1694 cm$^{-1}$, where as the lactone peak is shifted down slightly from 1750 cm$^{-1}$ to 1744 cm$^{-1}$.

Differential Scanning calorimetry: (TA Instruments 2920 DSC), 95.14° C. (endotherm); m.p.=91-96° C. (MEL-TEMP); (aspirin m.p.=1345° C., 4,4'-bipyridine m.p.=111-114° C.).

Thermogravimetric Analysis: (TA Instruments 2950 Hi-Resolution TGA), weight loss of 9% starting at 22.62° C., 49.06% weight loss starting at 102.97° C. followed by complete decomposition starting at 209.37° C.

EXAMPLE 4

Multi-Component Crystal of Ibuprofen:
Ibuprofen/4,4'-Bipyridine (2:1 Stoichiometry)

Figure 7C:
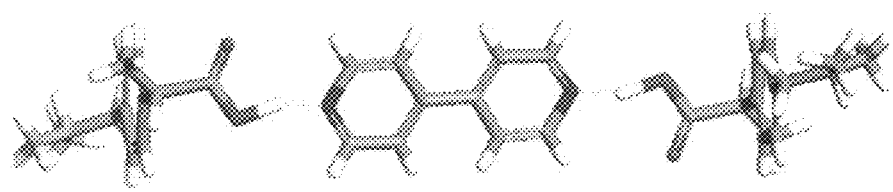
Figure 7D:
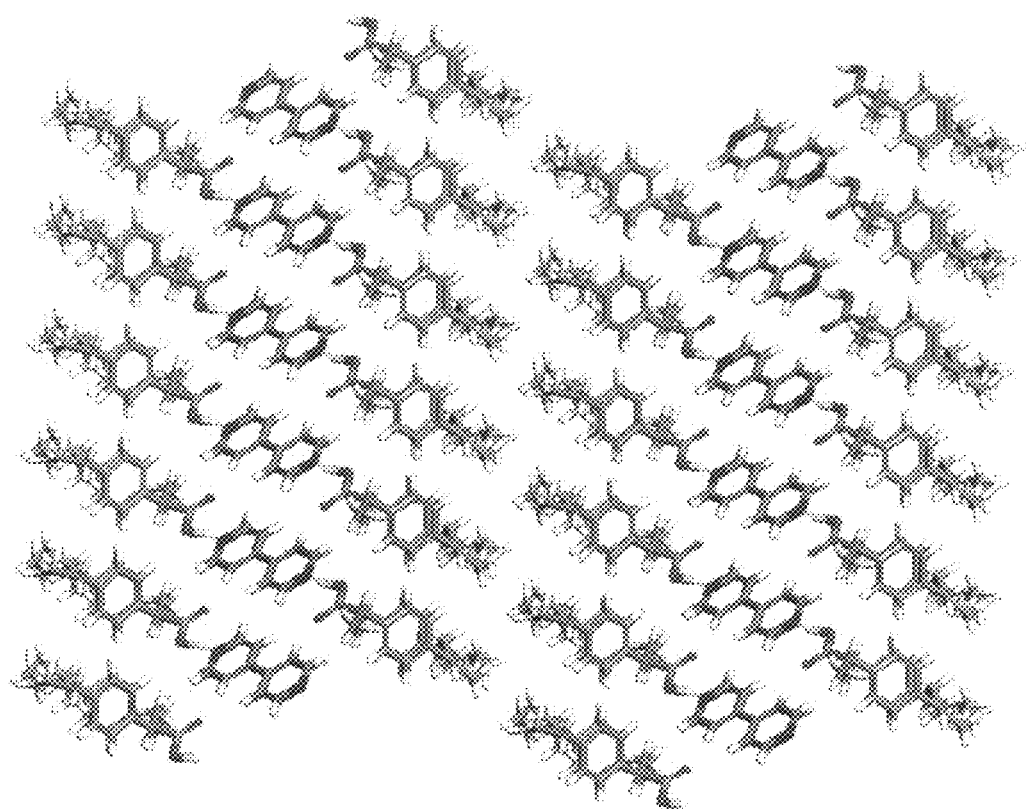

50 mg (0.242 mmol) racemic ibuprofen and 18 mg (0.0960 mmol) 4,4'-bipyridine were dissolved in 5 mL acetone. Slow evaporation of the solvent yielded colorless needles of a 2:1 ibuprofen/4,4'-bipyridine co-crystal, as shown in FIG. 7D.

Crystal data: (Bruker SMART-APEX CCD Diffractometer), $C_{36}H_{44}N_2O_4$, M=568.73, triclinic, space group P-1; a=5.759(3), b=11.683(6), c=24.705(11) Å, α=93.674(11), β=90.880(10), γ=104.045(7)°, U=1608.3(13) Å$^3$, T=200(2) K, Z=2, μ(Mo-Kα)=0.076 mm$^{-1}$, $D_c$=1.174 Mg/m$^3$, λ=0.71073 Å$^3$, F(000)=612, $2θ_{max}$=23.29°; 5208 reflections measured, 3362 unique ($R_{int}$=0.0826). Final residuals for 399 parameters were $R_1$=0.0964, $wR_2$=0.2510 for I>2σ(I), and $R_1$=0.1775, $wR_2$=0.2987 for all 3362 data.

Crystal packing: The co-crystal contains ibuprofen/bipyridine heterodimers, sustained by two hydrogen bonded carboxylic acidpyridine supramolecular synthons, arranged in a herringbone motif that packs in the space group P-l. The heterodimer is an extended version of the homodimer and packs to form a two-dimensional network sustained by π-π stacking of the bipyridine and phenyl groups of the ibuprofen and hydrophobic interactions from the ibuprofen tails.

Infrared Spectroscopy: (Nicolet Avatar 320 FTIR). Analysis observed stretching of aromatic C—H at 2899 cm$^{-1}$; N—H bending and scissoring at 1886 cm$_{-1}$; C=O stretching at 1679 cm$^{-1}$; C—H out-of-plane bending for both 4,4'-bipyridine and ibuprofen at 808 cm$^{-1}$ and 628 cm$^{-1}$.

Differential Scanning calorimetry: (TA Instruments 2920 DSC), 64.85° C. (endotherm) and 118.79° C. (endotherm); m.p.=113-120° C. (MEL-TEMP); (ibuprofen m.p.=75-77° C., 4,4'-bipyridine m.p.=111-114° C.).

Thermogravimetric Analysis: (TA Instruments 2950 Hi-Resolution TGA), 13.28% weight loss between room temperature and 100.02° C. immediately followed by complete decomposition.

X-ray powder diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. XRPD derived from the single crystal data, experimental (calculated): 3.4 (3.6); 6.9 (7.2); 10.4 (10.8); 17.3 (17.5); 19.1 (19.7).

EXAMPLE 5

Multi-Component Crystal of Flurbiprofen:
Flurbiprofen/4,4'-Bipyridine (2:1 Stoichiometry)

Figure 8A:
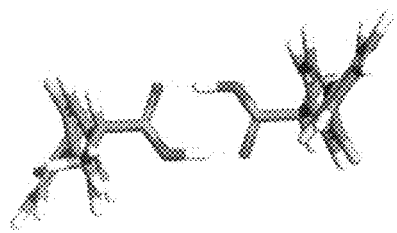
FIGS. 8A-8D show supramolecular entities containing synthons and corresponding crystal structures of pure flurbiprofen [2-(2-fluoror-4-biphenyl) propionic acid] and flurbiprofen/4,4'-bipyridine.
Figure 8B:
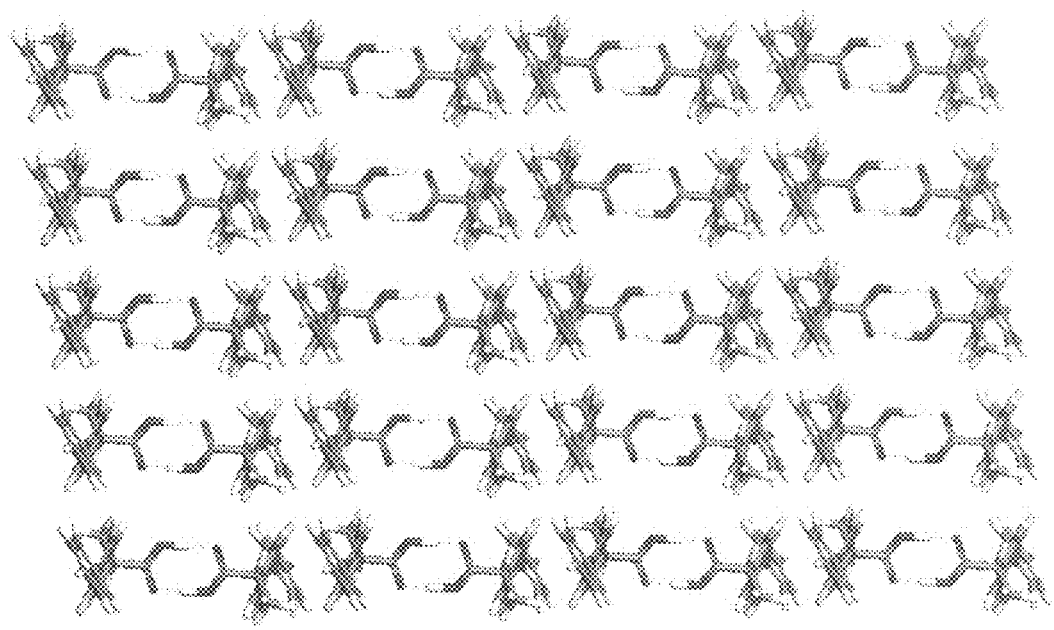
Figure 8C:
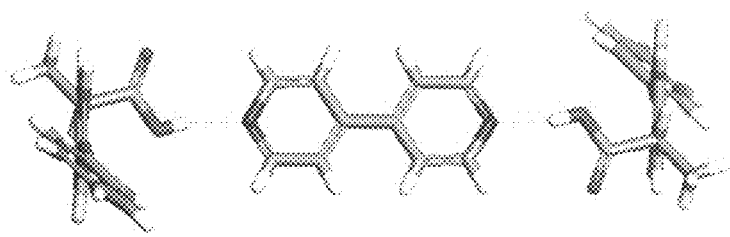
Figure 8D:
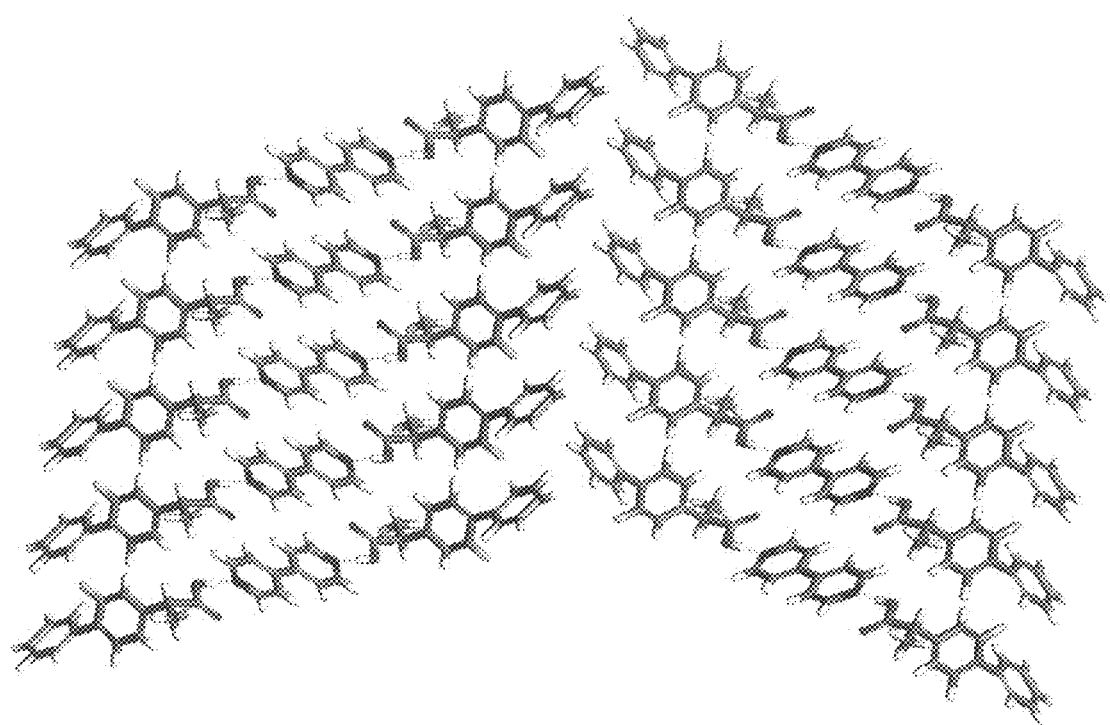

50 mg (0.2046 mmol) flurbiprofen and 15 mg (0.0960 mmol) 4,4'-bipyridine were dissolved in 3 mL acetone. Slow evaporation of the solvent yielded colorless needles of a 2:1 flurbiprofen/4,4'-bipyridine co-crystal, as shown in FIG. 8D.

Crystal data: (Bruker SMART-APEX CCD Diffractometer), $C_{40}H_{34}F_2N_2O_4$, M=644.69, monoclinic P2$_1$/n; a=5.860 (4), b=47.49(3), c=5.928(4) Å, β=107.382 (8)°, U=1574.3 (19) Å$^3$, T=200(2) K, Z=2, μ(Mo-Kα)=0.096 mm$^{-1}$, $D_c$=1.360 Mg/m$^3$, λ=0.71073 Å$^3$, F(000)=676, $2θ_{max}$=21.69°; 4246 reflections measured, 1634 unique ($R_{int}$=0.0677). Final residuals for 226 parameters were $R_1$=0.0908, $wR_2$=0.2065 for I>2σ(I), and $R_1$=0.1084, $wR_2$=0.2209 for all 1634 data.

Crystal packing: The co-crystal contains flurbiprofen/bipyridine heterodimers, sustained by two hydrogen bonded carboxylic acidpyridine supramolecular synthon, arranged in a herringbone motif that packs in the space group P2$_1$/n. The heterodimer is an extended version of the homodimer and packs to form a two-dimensional network sustained by π-π stacking and hydrophobic interactions of the bipyridine and phenyl groups of the flurbiprofen.

Infrared Spectroscopy: (Nicolet Avatar 320 FTIR), aromatic C—H stretching at 3057 cm$^{-1}$ and 2981 cm$^{-1}$; N—H bending and scissoring at 1886 cm$^{-1}$; C=O stretching at 1690 cm$^{-1}$; C=C and C=N ring stretching at 1418 cm$^{-1}$.

Differential Scanning calorimetry: (TA Instruments 2920 DSC), 162.47° C. (endotherm); m.p.=155-160° C. (MEL-TEMP); (flurbiprofen m.p.=110-111° C., 4,4'-bipyridine m.p.=111-114° C.).

Thermogravimetric Analysis: (TA Instruments 2950 Hi-Resolution TGA), 30.93% weight loss starting at 31.13° C. and a 46.26% weight loss starting at 168.74° C. followed by complete decomposition.

X-ray powder diffraction: (Rigaku Miniflex Diffractometer using Cu Kα (λ=1.540562), 30 kV, 15 mA), the powder data were collected over an angular range of 3° to 40° 2θ in continuous scan mode using a step size of 0.02° 2θ and a scan speed of 2.0°/minute. XRPD derived from the single crystal data: experimental (calculated): 16.8 (16.8); 17.1 (17.5); 18.1 (18.4); 19.0 (19.0); 20.0 (20.4); 21.3 (21.7); 22.7 (23.0); 25.0 (25.6); 26.0 (26.1); 26.0 (26.6); 26.1 (27.5); 28.2 (28.7); 29.1 (29.7).

EXAMPLE 6

Multi-Component Crystal of Flurbiprofen: Flurbiprofen/Trans-1,2-Bis(4-Pyridyl) Ethylene (2:1 Stoichiometry)

Figure 9A:
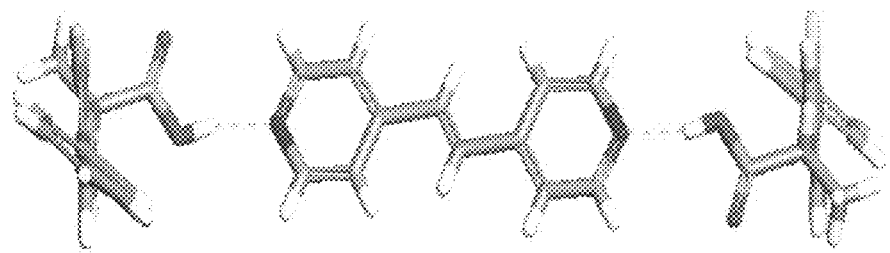
FIGS. 9A and 9B show the supramolecular entity containing the synthon of flurbiprofen/trans-1,2-bis(4-pyridyl) ethylene and the corresponding crystal structure, respectively.
Figure 9B:
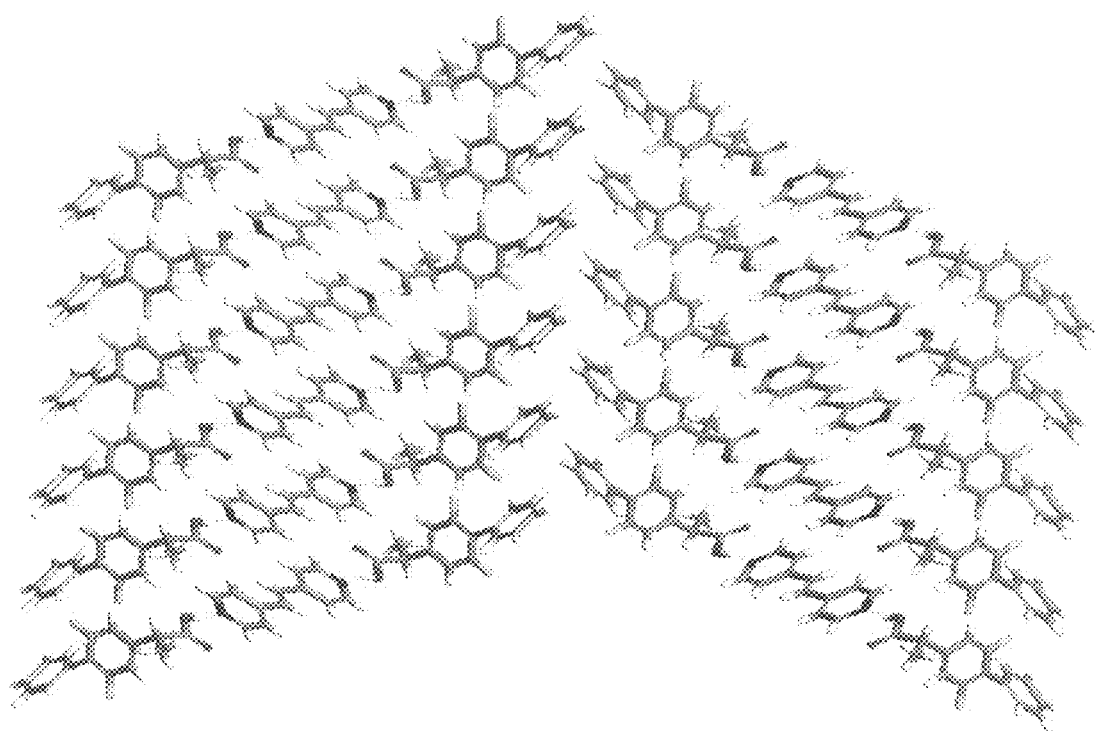

25 mg (0.1023 mmol) flurbiprofen and 10 mg (0.0548 mmol) trans-1,2-bis(4-pyridyl)ethylene were dissolved in 3 mL acetone. Slow evaporation of the solvent yielded colorless needles of a 2:1 flurbiprofen/1,2-bis(4-pyridyl)ethylene co-crystal, as shown in FIG. 9B.

Crystal data: (Bruker SMART-APEX CCD Diffractometer), $C_{42}H_{36}F_2N_2O_4$, M=670.73, monoclinic $P2_1/n$; a=5.8697(9), b=47.357(7), c=6.3587(10) Å, β=109.492(3)°, U=1666.2(4) Å$^3$, T=200(2) K, Z=2, μ(Mo-Kα)=0.093 mm$^{-1}$, $D_c$=1.337 Mg/m$^3$, λ=0.71073 Å$^3$, F(000)=704, $2θ_{max}$=21.69°, 6977 reflections measured, 2383 unique ($R_{int}$=0.0383). Final residuals for 238 parameters were $R_1$=0.0686, $wR_2$=0.1395 for I>2σ(I), and $R_1$=0.1403, $wR_2$=0.1709 for all 2383 data.

Crystal packing: The co-crystal contains flurbiprofen/1,2-bis(4-pyridyl)ethylene heterodimers, sustained by two hydrogen bonded carboxylic acid-pyridine supramolecular synthons, arranged in a herringbone motif that packs in the space group $P2_1/n$. The heterodimer from 1,2-bis(4-pyridyl)ethylene further extends the homodimer relative to example 5 and packs to form a two-dimensional network sustained by π-π stacking and hydrophobic interactions of the bipyridine and phenyl groups of the flurbiprofen.

Infrared Spectroscopy: (Nicolet Avatar 320 FTIR), aromatic C—H stretching at 2927 cm$^{-1}$ and 2850 cm$^{-1}$; N—H bending and scissoring at 1875 cm$^{-1}$; C=O stretching at 1707 cm$^{-1}$; C=C and C=N ring stretching at 1483 cm$^{-1}$.

Differential Scanning calorimetry: (TA Instruments 2920 DSC), 100.01° C., 125.59° C. and 163.54° C. (endotherms); m.p.=153-158° C. (MEL-TEMP); (flurbiprofen m.p.=110-111° C., trans-1,2-bis(4-pyridyl)ethylene m.p.=150-153° C.).

Thermogravimetric Analysis: (TA Instruments 2950 Hi-Resolution TGA), 91.79% weight loss starting at 133.18° C. followed by complete decomposition.

X-ray powder diffraction: (Rigaku Miniflex Diffractometer using Cu Kα (λ=1.540562), 30 kV, 15 mA), the powder data were collected over an angular range of 3° to 40° 2θ in continuous scan mode using a step size of 0.02° 2θ and a scan speed of 2.0°/minute. XRPD derived from the single crystal data, experimental (calculated): 3.6 (3.7); 17.3 (17.7); 18.1 (18.6); 18.4 (18.6); 19.1 (19.3); 22.3 (22.5); 23.8 (23.9); 25.9 (26.4); 28.1 (28.5).

EXAMPLE 7

Multi-Component Crystal of Carbamazepine: Carbamazepine/p-Phthalaldehyde (1:1 Stoichiometry)

Figure 10A:
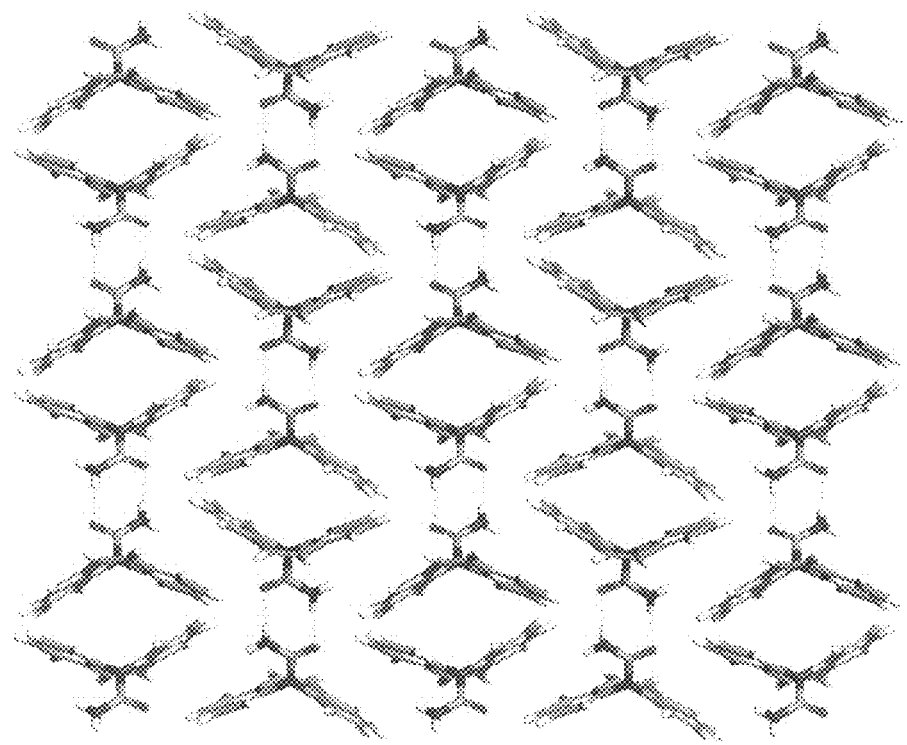
FIGS. 10A and 10B show the crystal structures of pure carbamazepine and carbamazepine/p-phthalaldehyde, respectively. Carbamazepine [5H-Dibenz(b, f) azepine-5-carboxamide] (CBZ) has been shown to exist in at least three anhydrous forms and two solvated forms (a dihydrate and an acetonate) (Himes, V. L. et al., Acta Crystallogr., 1981, 37:2242-2245; Lowes, M. M. J. et al., J. Pharm. Sci., 1987, 76:744-752; Reck, G. et al., Cryst. Res. Technol., 1986, 21:1463-1468). The primary intermolecular interaction in these crystal forms is the dimer formed between the carboxamide moieties of each CBZ molecule forming centrosymmetric dimers. The anhydrous polymorphs are monoclinic, trigonal, and triclinic. The polymorphs are enantiotropically related with the monoclinic form being the most thermodynamically stable at room temperature.
Figure 10B:
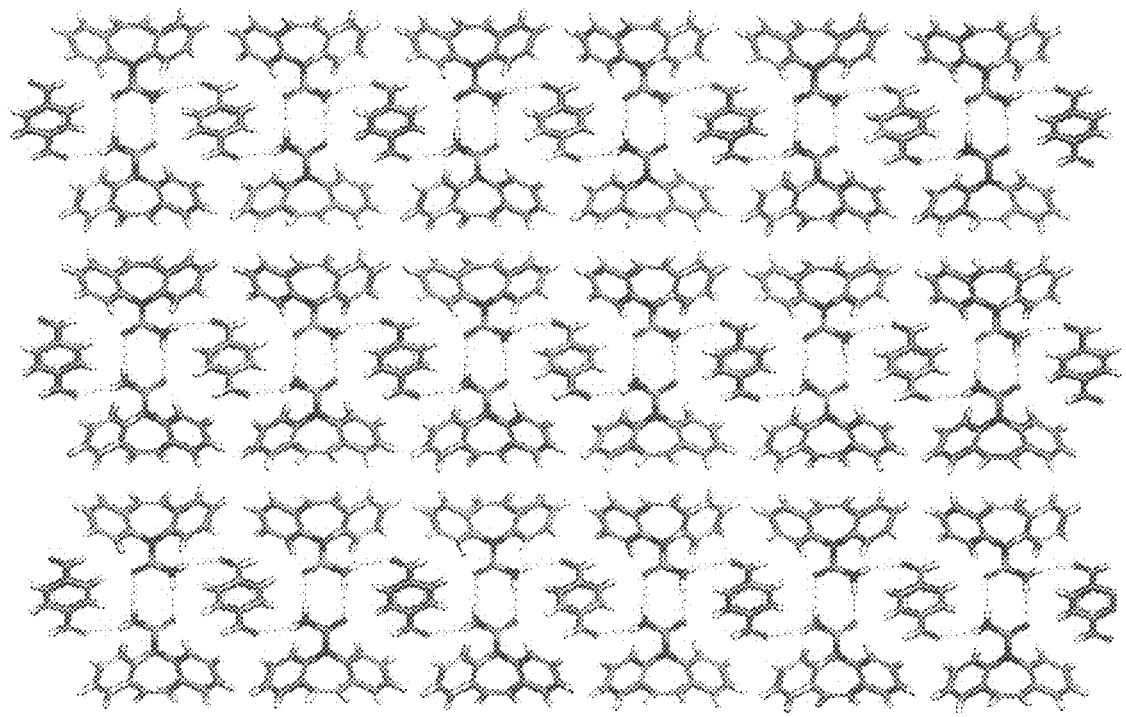

25 mg (0.1058 mmol) carbamazepine and 7 mg (0.0521 mmol) p-phthalaldehyde were dissolved in approximately 3 mL methanol. Slow evaporation of the solvent yielded colorless needles of a 1:1 carbamazepine/p-phthalaldehyde co-crystal, as shown in FIG. 10B.

Crystal data: (Bruker SMART-APEX CCD Diffractometer), $C_{38}H_{30}N_4O_4$, M=606.66, monoclinic C2/c; a=29.191(16), b=4.962(3), c=20.316(11) Å, β=92.105(8)°, U=2941(3) Å$^3$, T=200(2) K, Z=4, μ(Mo-Kα)=0.090 mm$^{-1}$, $D_c$=1.370 Mg/m$^3$, λ=0.71073 Å$^3$, F(000)=1272, $2θ_{max}$=43.66°, 3831 reflections measured, 1559 unique ($R_{int}$=0.0510). Final residuals for 268 parameters were $R_1$=0.0332, $wR_2$=0.0801 for I>2σ(I), and $R_1$=0.0403, $wR_2$=0.0831 for all 1559 data.

Crystal packing: The co-crystals contain hydrogen bonded carboxamide homodimers that crystallize in the space group C2/c. The 1° amines of the homodimer are bifurcated to the carbonyl of the p-phthalaldehyde forming a chain with an adjacent homodimer. The chains pack in a crinkled tape motif sustained by π-π interactions between phenyl rings of the CBZ.

Infrared Spectroscopy: (Nicolet Avatar 320 FTIR). The 1° amine unsymmetrical and symmetrical stretching was shifted down to 3418 cm$^{-1}$; aliphatic aldehyde and 1° amide C=O stretching was shifted up to 1690 cm$^{-1}$; N—H in-plane bending at 1669 cm$^{-1}$; C—H aldehyde stretching at 2861 cm$^{-1}$ and H—C=O bending at 1391 cm$^{-1}$.

Differential Scanning calorimetry: (TA Instruments 2920 DSC), 128.46° C. (endotherm), m.p.=121-124° C. (MEL-TEMP), (carbamazepine m.p.=190.2° C., p-phthalaldehyde m.p.=116° C.).

Thermogravimetric Analysis: (TA Instruments 2950 Hi-Resolution TGA), 17.66% weight loss starting at 30.33° C. then a 17.57% weight loss starting at 100.14° C. followed by complete decomposition.

X-ray powder diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. XRPD derived from the single crystal data, experimental (calculated): 8.5 (8.7); 10.6 (10.8); 11.9 (12.1); 14.4 (14.7) 15.1 (15.2); 18.0 (18.1); 18.5 (18.2); 19.8 (18.7); 23.7 (24.0); 24.2 (24.2); 26.4 (26.7); 27.6 (27.9); 27.8 (28.2); 28.7 (29.1); 29.3 (29.6); 29.4 (29.8).

EXAMPLE 8

Multi-Component Crystal of Carbamazepine: Carbamazepine/Nicotinamide (GRAs) (1:1 Stoichiometry)

Figure 11:
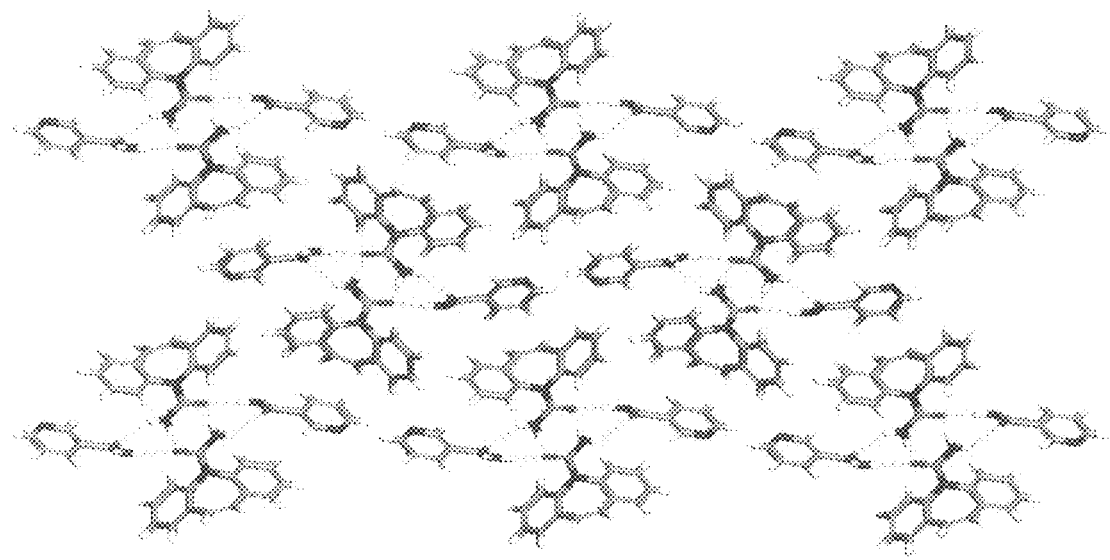
FIG. 11 shows the crystal structure of carbamazepine/nicotinamide (vitamin B3).

25 mg (0.1058 mmol) carbamazepine and 12 mg (0.0982 mmol) nicotinamide were dissolved in 4 mL of DMSO, methanol or ethanol. Slow evaporation of the solvent yielded colorless needles of a 1:1 carbamazepine/nicotinamide co-crystal, as shown in FIG. 11.

Using a separate method, 25 mg (0.1058 mmol) carbamazepine and 12 mg (0.0982 mmol) nicotinamide were ground together with mortar and pestle. The solid was determined to be 1:1 carbamazepine/nicotinamide microcrystals (XPD).

Crystal data: (Bruker SMART-APEX CCD Diffractometer), $C_{21}H_{18}N_4O_2$, M=358.39, monoclinic $P2_1/n$; a=5.0961 (8), b=17.595(3), c=19.647(3) Å, β=90.917(3)°, U=1761.5 (5) Å$^3$, T=200(2) K, Z=4, μ(Mo-Kα)=0.090 mm$^{-1}$, $D_c$=1.351 Mg/m$^3$, λ=0.71073 Å$^3$, F(000)=752, $2θ_{max}$=56.60°, 10919 reflections measured, 4041 unique ($R_{int}$=0.0514). Final residuals for 248 parameters were $R_1$=0.0732, $wR_2$=0.1268 for I>2σ(I), and $R_1$=0.1161, $wR_2$=0.1430 for all 4041 data.

Crystal packing: The co-crystals contain hydrogen bonded carboxamide homodimers. The 1° amines are bifurcated to the carbonyl of the nicotinamide on each side of the dimer. The 1° amines of each nicotinamide are hydrogen bonded to the carbonyl of the adjoining dimer. The dimers form chains with π-π interactions from the phenyl groups of the CBZ.

Infrared Spectroscopy: (Nicolet Avatar 320 FTIR), unsymmetrical and symmetrical stretching shifts down to 3443 cm$^{-1}$ and 3388 cm$^{-1}$ accounting for 1° amines; 1° amide C=O stretching at 1690 cm$^{-1}$; N—H in-plane bending at 1614 cm$^{-1}$; C=C stretching shifted down to 1579 cm$^{-1}$; aromatic H's from 800 cm$^{-1}$ to 500 cm$^{-1}$ are present.

Differential Scanning calorimetry: (TA Instruments 2920 DSC), 74.49° C. (endotherm) and 59.05° C. (endotherm), m.p.=153-158° C. (MEL-TEMP), (carbamazepine m.p.=190.2° C., nicotinamide m.p.=150-160° C.).

Thermogravimetric Analysis: (TA Instruments 2950 Hi-Resolution TGA), 57.94% weight loss starting at 205.43° C. followed by complete decomposition.

X-ray powder diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. XRPD: Showed analogous peaks to the simulated XRPD derived from the single crystal data. XRPD analysis experimental (calculated): 6.5 (6.7); 8.8 (9.0); 10.1 (10.3); 13.2 (13.5); 15.6 (15.8); 17.7 (17.9); 17.8 (18.1); 18.3 (18.6); 19.8 (20.1); 20.4 (20.7); 21.6 (22); 22.6 (22.8); 22.9 (23.2); 26.4 (26.7); 26.7 (27.0); 28.0 (28.4).

EXAMPLE 9

Multi-Component Crystal of Carbamazepine: Carbamazepine/Saccharin (GRAs) (1:1 Stoichiometry)

Figure 12:
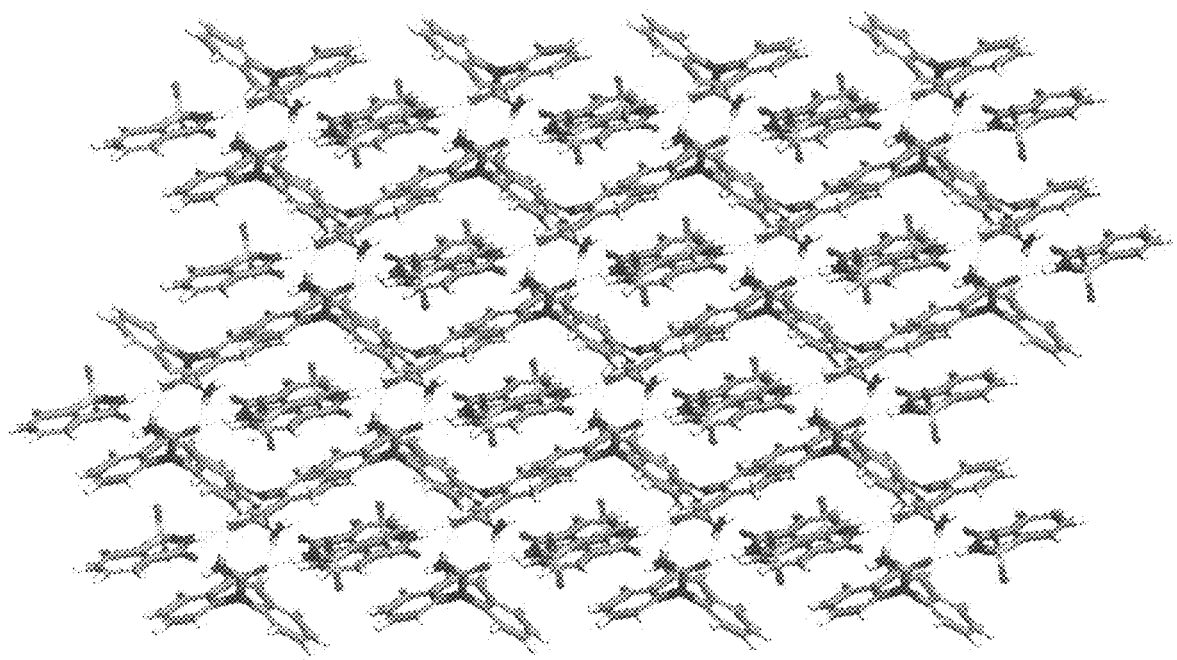
FIG. 12 shows the crystal structure of carbamazepine/saccharin, engineered using the carbamazepine/nicotinamide co-crystal as a model.

25 mg (0.1058 mmol) carbamazepine and 19 mg (0.1037 mmol) saccharin were dissolved in approximately 4 mL ethanol. Slow evaporation of the solvent yielded colorless needles of a 1:1 carbamazepine/saccharin cocrystal, as shown in FIG. 12. Solubility measurements indicate that this multiple-component crystal of carbamazepine has improved solubility over previously known forms of carbamezepine (e.g., increased molar solubility and longer solubility in aqueous solutions).

Crystal data: (Bruker SMART-APEX CCD Diffractometer), $C_{22}H_{17}N_3O_4S_1$, M=419.45, triclinic P-1; a=7.5140(11), b=10.4538(15), c=12.6826(18) Å, α=83.642(2)°, β=85.697 (2)°, γ=75.411(2)°, U=957.0(2) Å$^3$, T=200(2) K, Z=2, μ(Mo-Kα)=0.206 mm$^{-1}$, $D_c$=1.456 Mg/m$^3$, λ=0.71073 Å$^3$, F(000)=436, $2θ_{max}$=56.20°; 8426 reflections measured, 4372 unique ($R_{int}$=0.0305). Final residuals for 283 parameters were $R_1$=0.0458, $wR_2$=0.1142 for I>2σ(I), and $R_1$=0.0562, $wR_2$=0.1204 for all 4372 data.

Crystal packing: The co-crystals contain hydrogen bonded carboxamide homodimers. The 2° amines of the saccharin are hydrogen bonded to the carbonyl of the CBZ on each side forming a tetramer. The crystal has a space group of P-1 with π-π interactions between the phenyl groups of the CBZ and the saccharin phenyl groups.

Infrared Spectroscopy: (Nicolet Avatar 320 FTIR), unsymmetrical and symmetrical stretching shifts up to 3495 cm$^{-1}$ accounting for 1° amines; C=O aliphatic stretching was shifted up to 1726 cm$^{-1}$; N—H in-plane bending at 1649 cm$^{-1}$; C=C stretching shifted down to 1561 cm$^{-1}$; (O=S=O) sulfonyl peak at 1330 cm$^{-1}$ C—N aliphatic stretching 1175 cm$^{-1}$.

Differential Scanning calorimetry: (TA Instruments 2920 DSC), 75.31° C. (endotherm) and 177.32° C. (endotherm), m.p.=148-155° C. (MEL-TEMP); (carbamazepine m.p.=190.2° C., saccharin m.p.=228.8° C.).

Thermogravimetric Analysis: (TA Instruments 2950 Hi-Resolution TGA), 3.342% weight loss starting at 67.03° C. and a 55.09% weight loss starting at 118.71° C. followed by complete decomposition.

X-ray powder diffraction: (Rigaku Miniflex Diffractometer using Cu Kα (λ=1.540562), 30 kV, 15 mA). The powder data were collected over an angular range of 3° to 40° 2θ in continuous scan mode using a step size of 0.02° 2θ and a scan speed of 2.0°/minute. XRPD derived from the single crystal data, experimental (calculated): 6.9 (7.0); 12.2 (12.2); 13.6 (13.8); 14.0 (14.1); 14.1 (14.4); 15.3 (15.6); 15.9 (15.9); 18.1 (18.2); 18.7 (18.8); 20.2 (20.3); 21.3 (21.5); 23.7 (23.9); 26.3 (26.4); 28.3 (28.3).

EXAMPLE 10

Multi-Component Crystal of Carbamazepine: Carbamazepine/2,6-Pyridinedicarboxylic Acid (2:3 Stoichiometry)

Figure 14A:
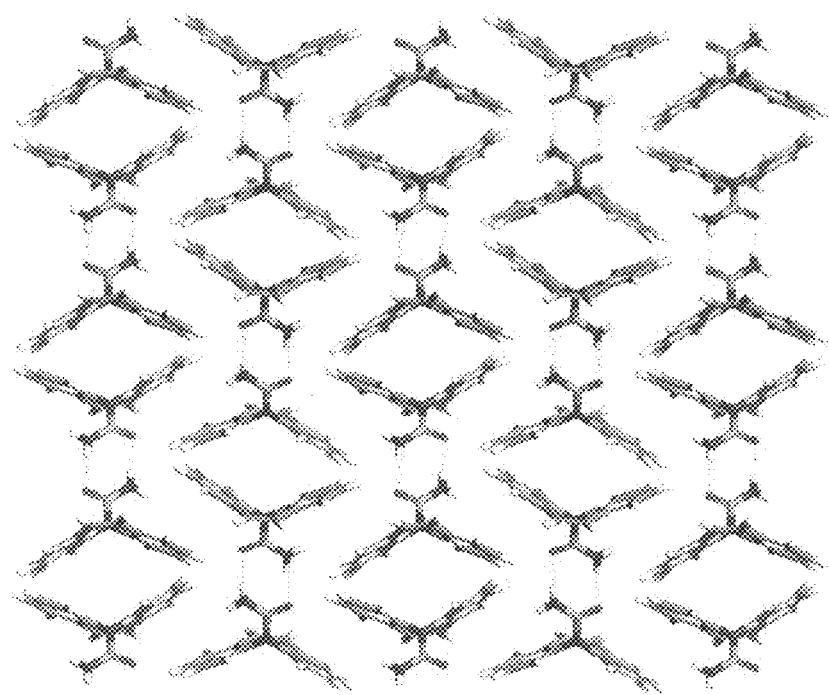
FIGS. 14A and 14B show the crystal structures of carbamazepine and carbamazepine/2,6-pyridinedicarboxylic acid, respectively.
Figure 14B:
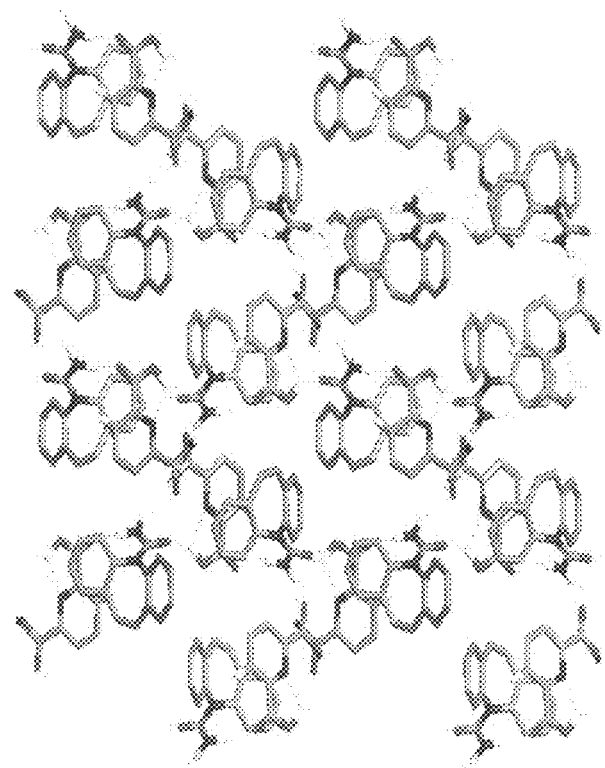

36 mg (0.1524 mmol) carbamazepine and 26 mg (0.1556 mmol) 2,6-pyridinedicarboxylic acid were dissolved in approximately 2 mL ethanol. Slow evaporation of the solvent yielded clear needles of a 1:1 carbamazepine/2,6-pyridinedicarboxylic acid co-crystal, as shown in FIG. 14B.

Crystal data: (Bruker SMART-APEX CCD Diffractometer). $C_{22}H_{17}N_3O_5$, M=403.39, orthorhombic P2(1)2(1)2(1); a=7.2122, b=14.6491, c=17.5864 Å, α=90°, β=90°, γ=90°, V=1858.0(2) Å$^3$, T=100 K, Z=4, μ(MO-Kα)=0.104 mm$^{-1}$, $D_c$=1.442 Mg/m$^3$, λ=0.71073 Å$^3$, F(000)840, $2θ_{max}$=28.3. 16641 reflections measured, 4466 unique ($R_{int}$=0.093). Final residuals for 271 parameters were $R_1$=0.0425 and $wR_2$=0.0944 for I>2σ(I).

Crystal packing: Each hydrogen on the CBZ 1° amine is hydrogen bonded to a carbonyl group of a different 2,6-pyridinedicarboxylic acid moiety. The carbonyl of the CBZ carboxamide is hydrogen bonded to two hydroxide groups of one 2,6-pyridinedicarboxylic acid moiety.

Infrared Spectroscopy: (Nicolet Avatar 320 FTIR). 3439 cm$^{-1}$, (N—H stretch, 1° amine, CBZ); 1734 cm$^{-1}$, (C=O); 1649 cm$^{-1}$, (C=C).

Melting Point: 214-216° C. (MEL-TEMP). (carbamazepine m.p.=191-192° C., 2,6-pyridinedicarboxylic acid m.p.=248-250° C.).

Thermogravimetric Analysis: (TA Instruments 2950 Hi-Resolution TGA). 69% weight loss starting at 215° C. and a 17% weight loss starting at 392° followed by complete decomposition.

EXAMPLE 11

Multi-Component Crystal of Carbamazepine: Carbamazepine/5-Nitroisophthalic Acid (1:1 Stoichiometry)

Figure 15A:
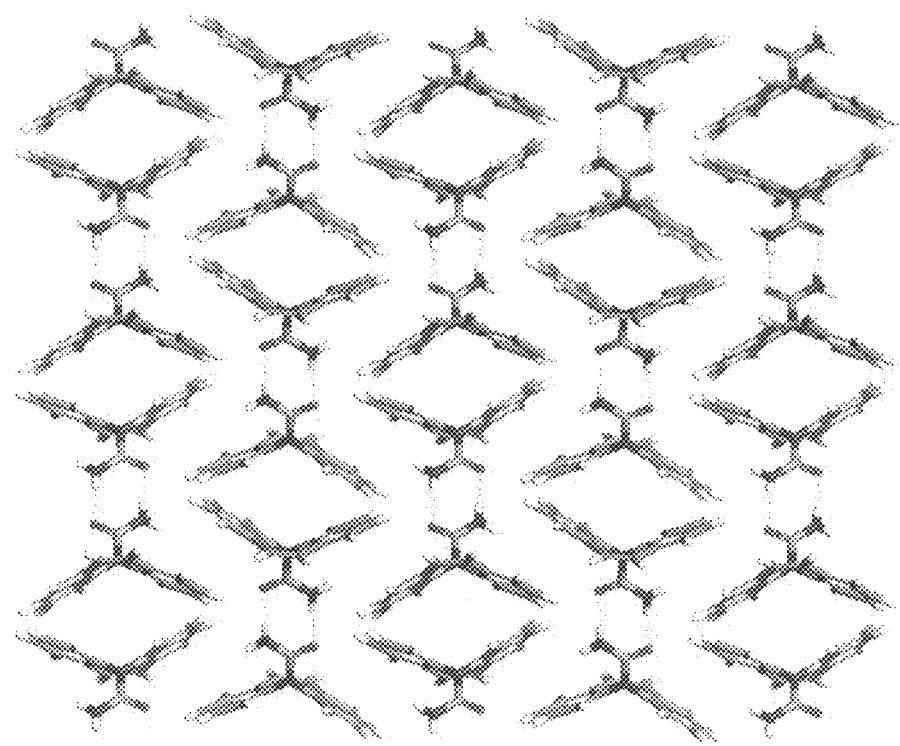
FIGS. 15A and 15B show the crystal structures of carbamazepine and carbamazepine/5-nitroisophthalic acid, respectively.
Figure 15B:
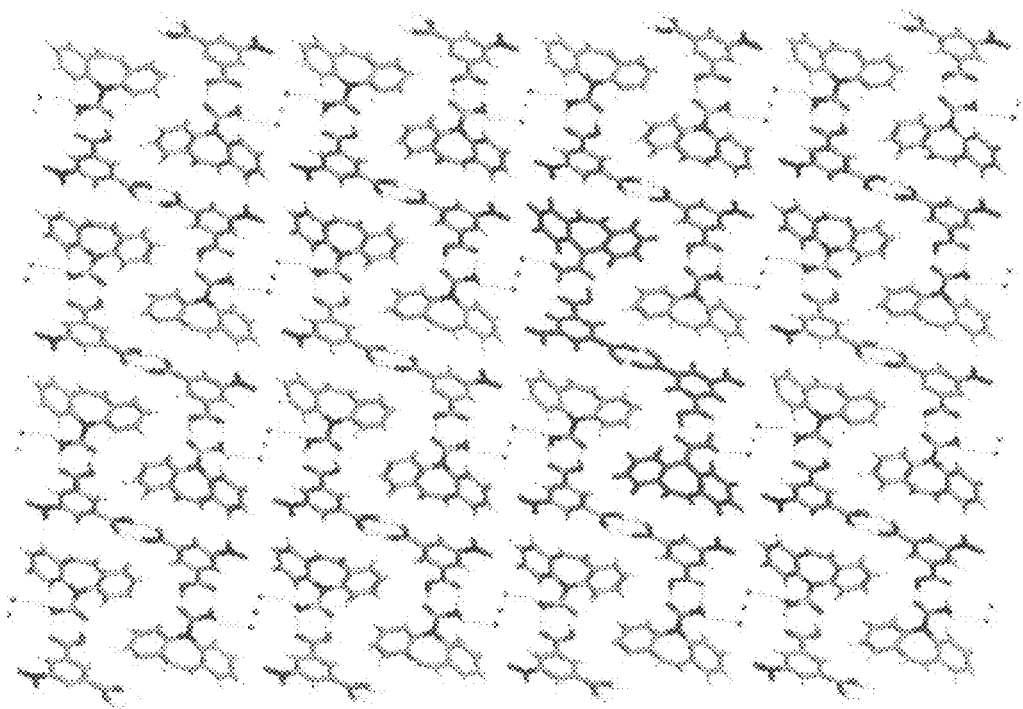

40 mg (0.1693 mmol) carbamazepine and 30 mg (0.1421 mmol) 5-nitroisophthalic acid were dissolved in approximately 3 mL methanol or ethanol. Slow evaporation of the solvent yielded yellow needles of a 1:1 carbamazepine/5-nitroisophthalic acid co-crystal, as shown in FIG. 15B.

Crystal data: (Bruker SMART-APEX CCD Diffractometer). $C_{47}H_{40}N_6O_{16}$, M=944.85, monoclinic C2/c; a=34.355(8), b=5.3795(13), c=23.654(6) Å, α=90°, β=93.952(6)°, γ=90°, V=4361.2(18)Å$^3$, T=200(2) K, Z=4, μ(MO-Kα)=0.110 mm$^{-1}$, $D_c$=1.439 Mg/m$^3$, λ=0.71073 Å$^3$, F(000)1968, $2θ_{max}$=26.43°. 11581 reflections measured, 4459 unique ($R_{int}$=0.0611). Final residuals for 311 parameters were $R_1$=0.0725, $wR_2$=0.1801 for I>2σ(I), and $R_1$=0.1441, $wR_2$=0.1204 for all 4459 data.

Crystal packing: The co-crystals are sustained by hydrogen bonded carboxylic acid homodimers between the two 5-nitroisophthalic acid moieties and hydrogen bonded carboxy-amide heterodimers between the carbamazepine and 5-nitroisophthalic acid moiety. There is solvent hydrogen bonded to an additional N—H donor from the carbamazepine moiety.

Infrared Spectroscopy: (Nicolet Avatar 320 FTIR). 3470 cm$^{-1}$, (N—H stretch, 1° amine, CBZ); 3178 cm$^{-1}$, (C—H stretch, alkene); 1688 cm$^{-1}$, (C═O); 1602 cm$^{-1}$, (C═C).

Differential Scanning calorimetry: (TA Instruments 2920 DSC). 190.51° C. (endotherm). m.p.=NA (decomposes at 197-200° C.) (MEL-TEMP). (carbamazepine m.p.=191-192° C., 5-nitroisophthalic acid m.p.=260-261° C.).

Thermogravimetric Analysis: (TA Instruments 2950 Hi-Resolution TGA). 32.02% weight loss starting at 202°, a 12.12% weight loss starting at 224° and a 17.94% weight loss starting at 285° followed by complete decomposition.

X-ray powder diffraction: (Rigaku Miniflex Diffractometer using CuKα (λ=1.540562), 30 kV, 15 mA). The powder data were collected over an angular range of 3 to 40 2 in continuous scan mode using a step size of 0.02 2 and a scan speed of 2.0/min. XRPD: Showed analogous peaks to the simulated XRPD derived from the single crystal data. XRPD analysis experimental (calculated): 10.138 (10.283), 15.291 (15.607), 17.438 (17.791), 21.166 (21.685), 31.407 (31.738), 32.650 (32.729).

EXAMPLE 12

Multi-Component Crystal of Carbamazepine: Carbamazepine/Acetic Acid (1:1 Stoichiometry)

Figure 16A:
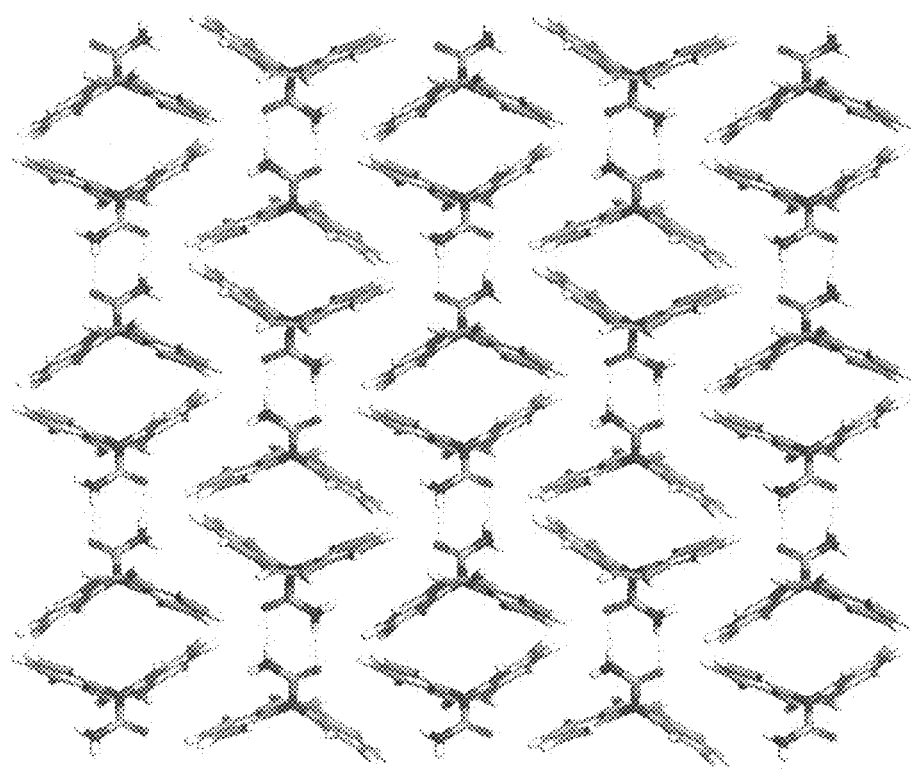
FIGS. 16A and 16B show the crystal structures of carbamazepine and carbamazepine/acetic acid.
Figure 16B:
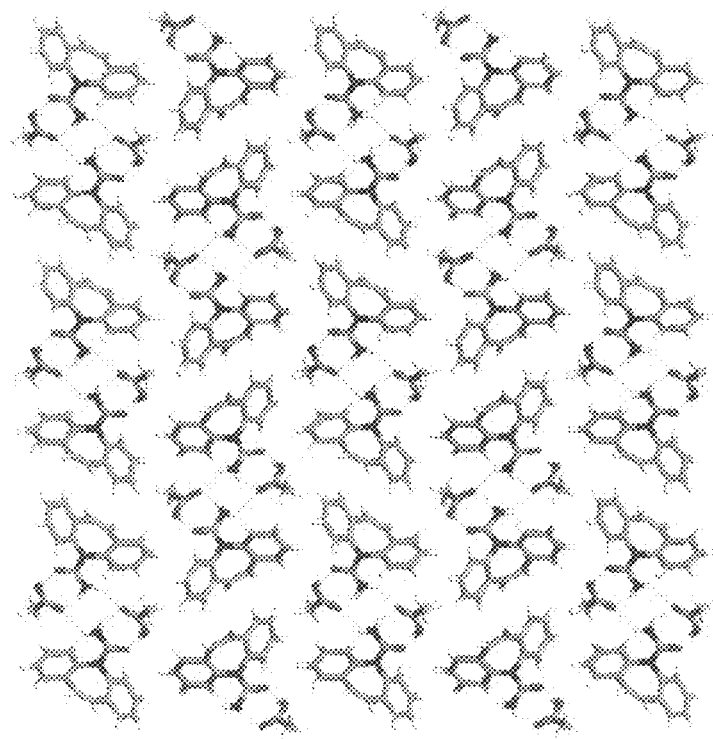

25 mg (0.1058 mmol) carbamazepine was dissolved in approximately 2 mL acetic acid. Slow evaporation of the solvent yielded yellow needles of a 1:1 carbamazepine/acetic acid co-crystal, as shown in FIG. 16B.

Crystal data: (Bruker SMART-APEX CCD Diffractometer). $C_{17}H_{16}N_2O_3$, M=296.32, monoclinic P2(1)/c; a=5.1206(4), b=15.7136(13), c=18.4986(15) Å, α=90°, β=96.5460(10)°, γ=90°, V=1478.8(2)Å$^3$, T=100(2) K, Z=4, μ(MO-Kα)=0.093 mm$^{-1}$, $D_c$=1.331 Mg/m$^3$, λ=0.71073 Å$^3$, F(000)624, $2θ_{max}$=28.4°. 12951 reflections measured, 3529 unique ($R_{int}$=0.076). Final residuals for 203 parameters were $R_1$=0.0492, $wR_2$=0.1335 for I>2σ(I).

Crystal packing: The co-crystal is sustained by hydrogen bonded carboxamide-carboxylic heterodimers. The second 1° amine hydrogen from each CBZ joins 2 heterodimers side by side forming a tetramer.

Infrared Spectroscopy: (Nicolet Avatar 320 FTIR). 3462 cm$^{-1}$, (N—H stretch, 1° amine, CBZ); 1699 cm$^{-1}$, (C═O); 1629 cm$^{-1}$, (C═C, CBZ); 1419 cm$^{-1}$, (COOH, acetic acid).

Melting Point: 187° C. (MEL-TEMP). (carbamazepine m.p.=191-192° C., acetic acid m.p.=16.6° C.).

Thermogravimetric Analysis: (TA Instruments 2950 Hi-Resolution TGA). 20.62% weight loss starting at 104° and a 77.05% weight loss starting at 200° followed by complete decomposition.

EXAMPLE 13

Multi-Component Crystal of Carbamazepine: Carbamazepine/1,3,5,7-Adamantanetetracarboxylic Acid (1:1 Stoichiometry)

Figure 17A:
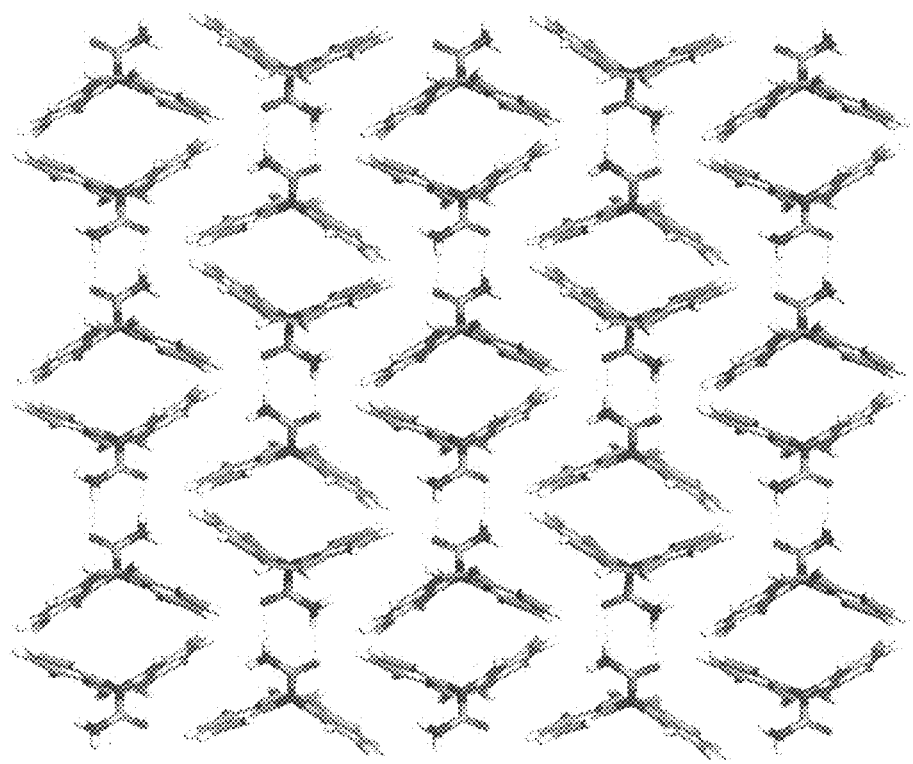
FIGS. 17A and 17B show the crystal structure of carbamazepine and carbamazepine/adamantanetetracarboxylic acid.
Figure 17B:
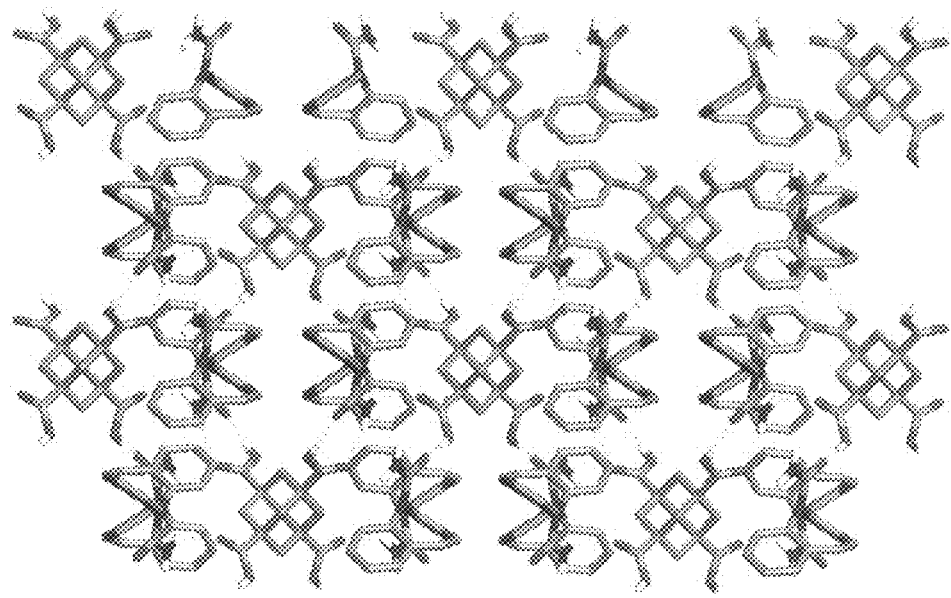

15 mg (0.1524 mmol) carbamazepine and 20 mg (0.1556 mmol) 1,3,5,7-adamantanetetracarboxylic acid were dissolved in approximately 1 mL methanol or 1 mL ethanol. Slow evaporation of the solvent yields clear plates of a 2:1 carbamazepine/1,3,5,7-adamantanetetracarboxylic acid co-crystal, as shown in FIG. 17B.

Crystal data: (Bruker SMART-APEX CCD Diffractometer). $C_{44}H_{40}N_2O_{10}$, M=784.80, monoclinic C2/c; a=18.388(4), b=12.682(3), c=16.429(3) Å, β=100.491(6)°, V=3767.1(14) Å$^3$, T=100(2) K, Z=4, μ(MO-Kα)=0.099 mm$^{-1}$, $D_c$=1.384 Mg/m$^3$, λ=0.71073Å$^3$, F(000)1648, $2θ_{max}$=28.20°. 16499 reflections measured, 4481 unique ($R_{int}$=0.052). Final residuals for 263 parameters were $R_1$=0.0433 and $wR_2$=0.0913 for I>2σ(I).

Crystal packing: The co-crystals form a single 3D network of four tetrahedron, linked by square planes similar to the PtS topology. The crystals are sustained by hydrogen bonding.

Infrared Spectroscopy: (Nicolet Avatar 320 FTIR). 3431 cm$^{-1}$, (N—H stretch, 1° amine, CBZ); 3123 cm$^{-1}$, (C—H stretch, alkene); 1723 cm$^{-1}$, (C═O); 1649 cm$^{-1}$, (C═C).

Melting Point: (MEL-TEMP). 258-260° C. (carbamazepine m.p.=191-192° C., adamantanetetracarboxylic acid m.p.=>390° C.).

Thermogravimetric Analysis: (TA Instruments 2950 Hi-Resolution TGA). 9% weight loss starting at 189° C., a 52% weight loss starting at 251° C. and a 31% weight loss starting at 374° C. followed by complete decomposition.

EXAMPLE 14

Multi-Component Crystal of Carbamazepine: Carbamazepine/Benzoquinone (1:1 Stoichiometry)

Figure 18A:
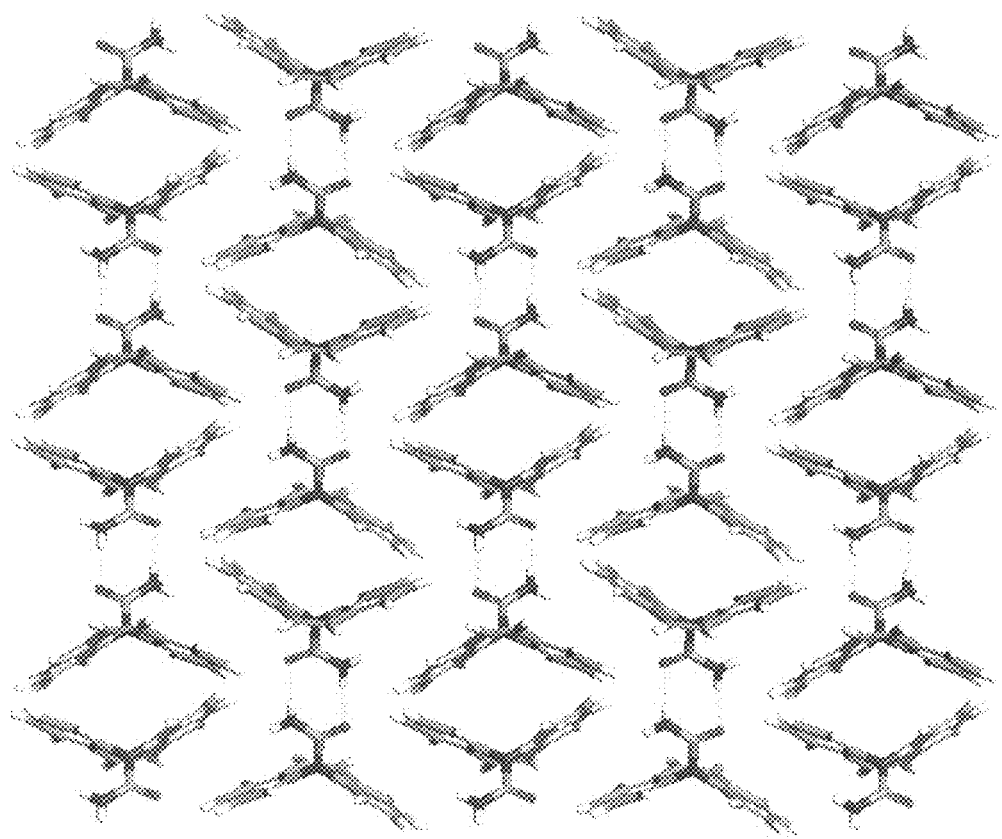
FIGS. 18A and 18B show the crystal structure of carbamazepine and carbamazepine/benzoquinone.
Figure 18B:
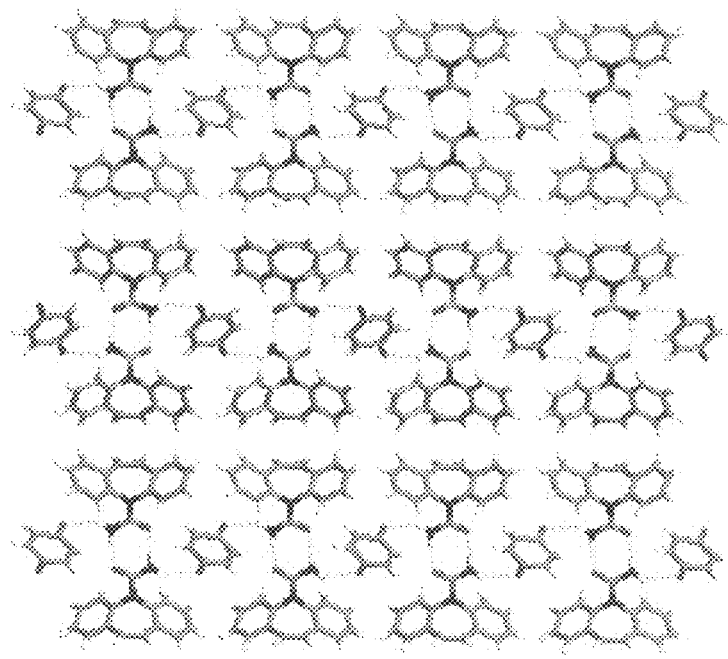

25 mg (0.1058 mmol) carbamazepine and 11 mg (0.1018 mmol) benzoquinone was dissolved in 2 mL methanol or THF. Slow evaporation of the solvent produced an average yield of yellow crystals of a 1:1 carbamazepine/benzoquinone co-crystal, as shown in FIG. 18B.

Crystal data: (Bruker SMART-APEX CCD Diffractometer). $C_{21}H_{16}N_2O_3$, M=344.36, monoclinic P2(1)/c; a=10.3335(18), b=27.611(5), c=4.9960(9) Å, β=102.275(3)°, V=1392.9(4) Å$^3$, T=100(2) K, Z=3, $D_c$=1.232 Mg/m$^3$, μ(MO-Kα)=0.084 mm$^{-1}$, λ=0.71073 Å$^3$, F(000)540, $2θ_{max}$=28.24°. 8392 reflections measured, 3223 unique ($R_{int}$=0.1136). Final residuals for 199 parameters were $R_1=0.0545$ and $wR_2=0.1358$ for $I>2\sigma(I)$, and $R_1=0.0659$ and $wR_2=0.1427$ for all 3223 data.

Crystal packing: The co-crystals contain hydrogen bonded carboxamide homodimers. Each 1° amine on the CBZ is bifurcated to a carbonyl group of a benzoquinone moiety. The dimers form infinite chains.

Infrared Spectroscopy: (Nicolet Avatar 320 FTIR). 3420 $cm^{-1}$, (N—H stretch, 1° amine, CBZ); 2750 $cm^{-1}$, (aldehyde stretch); 1672 $cm^{-1}$, (C=O); 1637 $cm^{-1}$, (C=C, CBZ).

Melting Point: 170° C. (MEL-TEMP). (carbamazepine m.p.=191-192° C., benzoquinone m.p.=115.7° C.).

Thermogravimetric Analysis: (TA Instruments 2950 Hi-Resolution TGA). 20.62% weight loss starting at 168° and a 78% weight loss starting at 223° followed by complete decomposition.

EXAMPLE 15

Multi-Component Crystal of Carbamazepine: Carbamazepine/Butyric Acid (1:1 Stoichiometry)

Figure 19A:
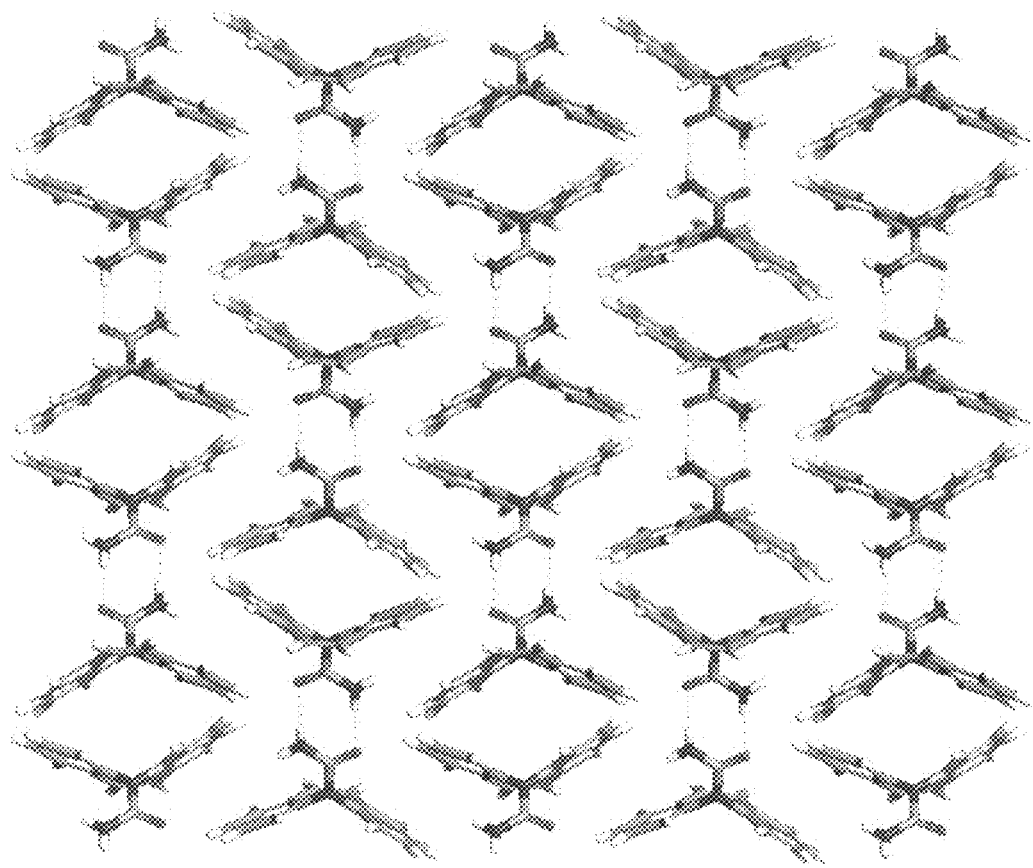
FIGS. 19A and 19B show the crystal structure of carbamazepine and carbamazepine/butyric acid.
Figure 19B:
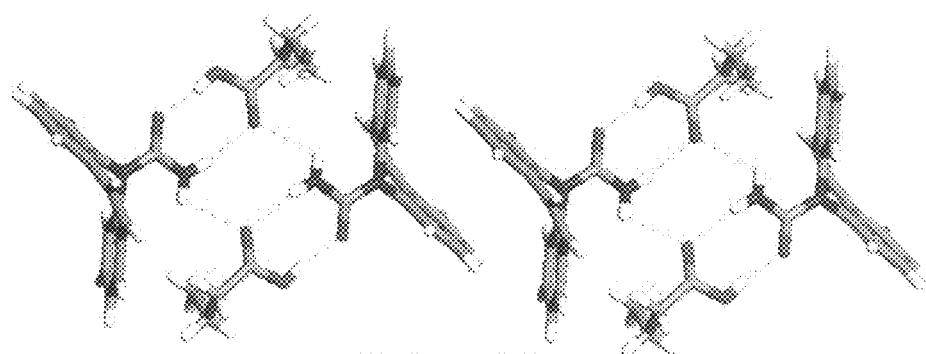

10 mg (0.0423 mmol) carbamazepine was dissolved in approximately 1 mL butyric acid. Slow evaporation of the solvent mixture produced an average yield of yellow/brown crystals of a 1:1 carbamazepine/butyric acid co-crystal, as shown in FIG. 19B.

Crystal data: (Bruker SMART-APEX CCD Diffractometer). $C_{19}H_{20}N_2O_3$, M=324.37, triclinic P-1; a=9.1567, b=10.1745, c=10.5116 Å, α=72.850°, β=70.288°, γ=67.269°, V=832.17 Å$^3$, T=100° K, Z=2, μ(MO-Kα)=0.088 $mm^{-1}$, $D_c$=1.290 Mg/m$^3$, λ=0.71073 Å$^3$, F(000)344, $2\theta_{max}$=28.28°. 5315 reflections measured, 3686 unique ($R_{int}$=0.0552). Final residuals for 217 parameters were $R_1$=0.0499, $wR_2$=0.1137 for $I>2\sigma(I)$, and $R_1$=0.0678, $wR_2$=0.1213 for all 3686 data.

Crystal packing: The co-crystals are sustained by hydrogen bonded carboxamide-carboxylic heterodimers between the carbamazepine moieties and the butyric acid moieties. The second 1° amine hydrogen from each CBZ joins 2 heterodimers side by side forming a tetramer.

Infrared Spectroscopy: (Nicolet Avatar 320 FTIR). 3486 $cm^{-1}$, (N—H stretch, 1° amine, CBZ); 3307 $cm^{-1}$, (C—H stretch, alkene); 1684 $cm^{-1}$, (C=O); 1540 $cm^{-1}$, (C=C).

Melting Point: 63-64° C. (MEL-TEMP). (carbamazepine m.p.=191-192° C., butyric acid m.p.=−94° C.).

Thermogravimetric Analysis: (TA Instruments 2950 Hi-Resolution TGA).16% weight loss starting at 54°, a 16% weight loss starting at 134° and a 49% weight loss starting at 174° followed by complete decomposition.

EXAMPLE 16

Multi-Component Crystal of Carbamazepine: Carbamazepine/DMSO (1:1 Stoichiometry)

Figure 20A:
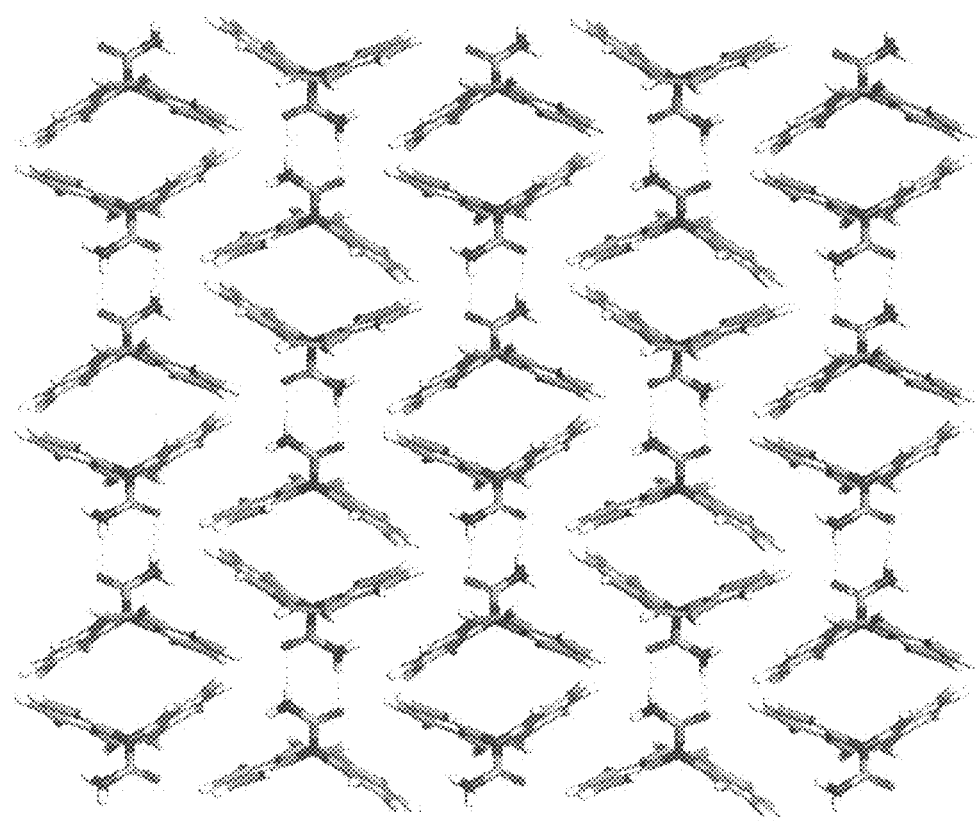
FIGS. 20A and 20B show the crystal structure of carbamazepine and carbamazepine/DMSO.
Figure 20B:
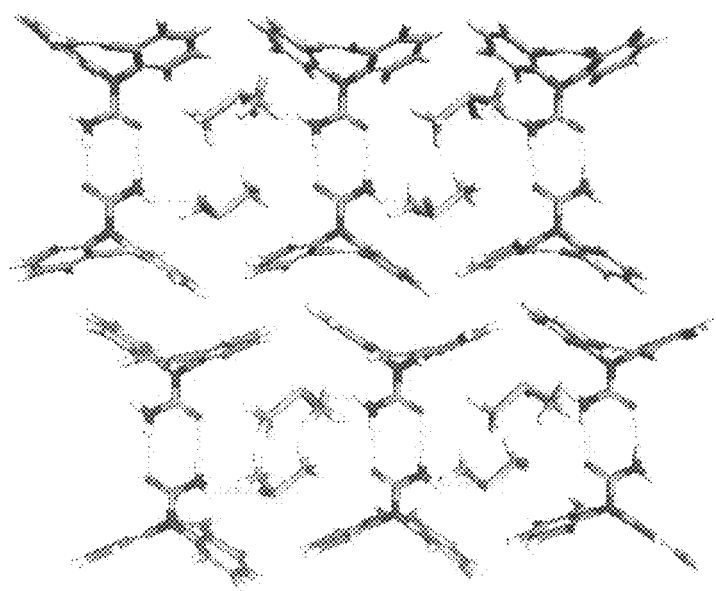

25 mg (0.1058 mmol) carbamazepine was dissolved in approximately 1.5 mL DMSO. Slow evaporation of the solvent yielded colorless plates of a 1:1 carbamazepine/DMSO co-crystal, as shown in FIG. 20B.

Crystal data: (Bruker SMART-APEX CCD Diffractometer). $C_{34}H_{36}N_4O_4S_2$, M=628.79, triclinic P-1; a=7.3254(19), b=8.889(2), c=12.208(3) Å, α=94.840(5)°, β=94.926(5)°, γ=100.048(5)°, V=775.8(3)Å$^3$, T=200(2) K, Z=2, μ(MO-Kα)=0.216 $mm^{-1}$, $D_c$=1.320 Mg/m$^3$, λ=0.71073 Å$^3$, F(000) 320, $2\theta_{max}$=28.3°. 4648 reflections measured, 3390 unique ($R_{int}$=0.0459). Final residuals for 209 parameters were $R_1$=0.0929, $wR_2$=0.3043 for $I>2\sigma(I)$.

Crystal packing: The co-crystals are sustained by the hydrogen bonded carboxamide homosynthon. The 1° amines are hydrogen bonded to the sulfoxide of the DMSO on each side of the homosynthon. The crystal is stabilized by π-π interactions from the tricyclic azepine ring system groups of the CBZ.

Infrared Spectroscopy: (Nicolet Avatar 320 FTIR). 3369 $cm^{-1}$ (N—H stretch, 1° amine, CBZ); 1665 $cm^{-1}$ (C=O stretching); 1481 $cm^{-1}$ (C=C).

Differential Scanning calorimetry: (TA Instruments 2920 DSC). 100° C., 193° C. (endotherms). m.p.=189° C. (MEL-TEMP). (carbamazepine m.p.=191-192° C., DMSO m.p.=18.45° C.)

Thermogravimetric Analysis: (TA Instruments 2950 Hi-Resolution TGA). 26% weight loss starting at 102°, a 64% weight loss starting at 212° followed by complete decomposition.

EXAMPLE 17

Multi-Component Crystal of Carbamazepine: Carbamazepine/Formamide (1:1 Stoichiometry)

Figure 21A:
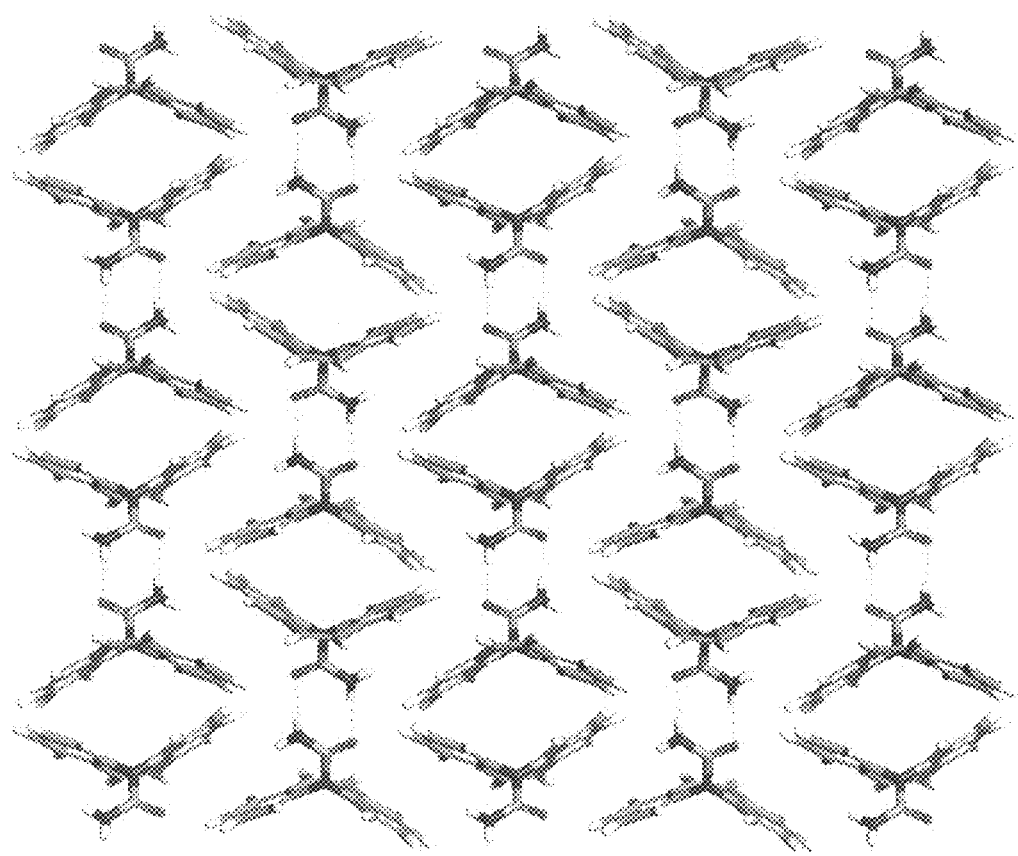
FIGS. 21A and 21B show the crystal structure of carbamazepine and carbamazepine/formamide.
Figure 21B:
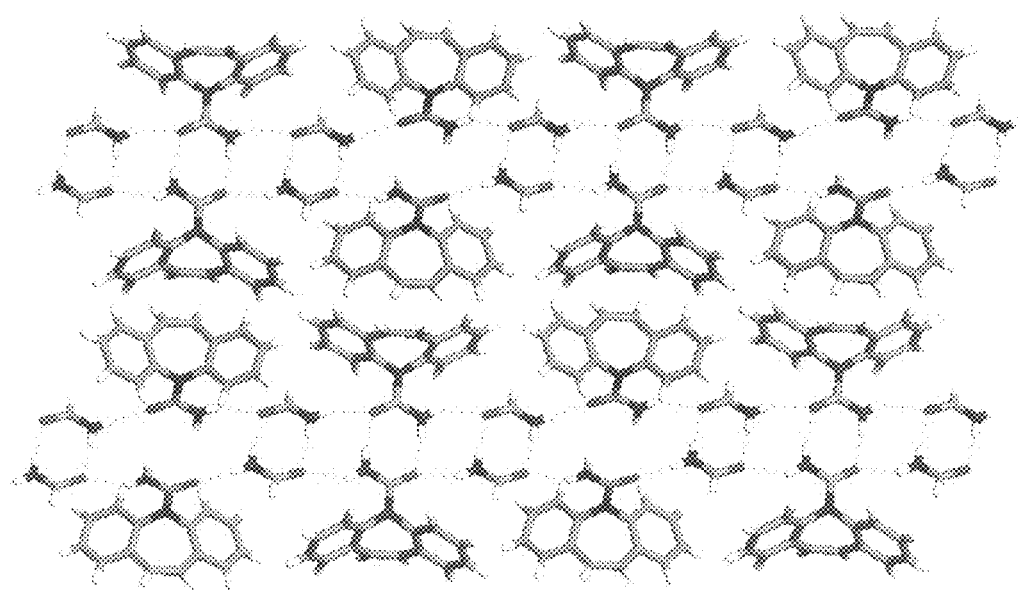

10 mg (0.0423 mmol) carbamazepine was dissolved in a mixture of approximately 1 mL formamide/1 mL THF or 1 mL formamide/1 mL methanol. Slow evaporation of the solvent mixture produced an average yield of clear needles of a 1:1 carbamazepine/formamide co-crystal, as shown in FIG. 21B.

Crystal data: (Bruker SMART-APEX CCD Diffractometer). $C_{16}H_{15}N_3O_2$, M=281.31, triclinic P-1; a=5.1077(11), b=16.057(3), c=17.752(4) Å, α=73.711(3)°, β=89.350(3)°, γ=88.636(3)°, V=1397.1(5) Å$^3$, T=100° K, Z=4, μ(MO-Kα)=0.091 $mm^{-1}$, $D_c$=1.337 Mg/m$^3$, λ=0.71073 Å$^3$, F(000)592, $2\theta_{max}$=28.33°. 11132 reflections measured, 6272 unique ($R_{int}$=0.1916). Final residuals for 379 parameters were $R_1$=0.0766 and $wR_2$=0.1633 for $I>2\sigma(I)$.

Crystal packing: The co-crystals are sustained by hydrogen bonded carboxamide homodimers between two carbamazepine moieties and carboxylic acid homodimers between two formamide moieties. Infinite chains are formed by the homodimers linked side by side, with every other set of CBZ molecules attached on the sides of the chain but not bonded to form a dimer.

Infrared Spectroscopy: (Nicolet Avatar 320 FTIR). 3392 $cm^{-1}$, (N—H stretch, 1° amine, CBZ); 2875 $cm^{-1}$, (C—H stretch, alkene); 1653 $cm^{-1}$, (C=O); 1590 $cm^{-1}$, (C=C).

Melting Point: 142-144° C. (MEL-TEMP). (carbamazepine m.p.=191-192° C., formamide m.p.=−94° C.).

Thermogravimetric Analysis: (TA Instruments 2950 Hi-Resolution TGA). 27% weight loss starting at 138°, a 67% weight loss starting at 195° followed by complete decomposition.

EXAMPLE 18

Multi-Component Crystal of Carbamazepine: Carbamazepine/Formic Acid (1:1 Stoichiometry)

Figure 22A:
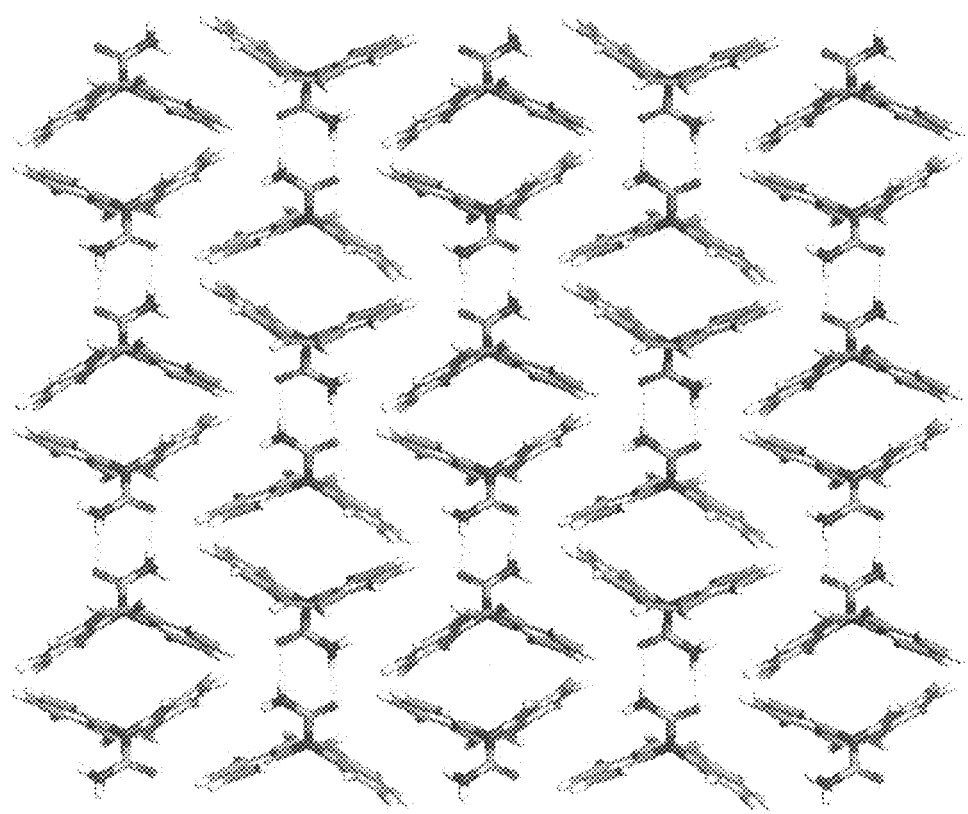
FIGS. 22A and 22B show the crystal structure of carbamazepine and carbamazepine/formic acid.
Figure 22B:
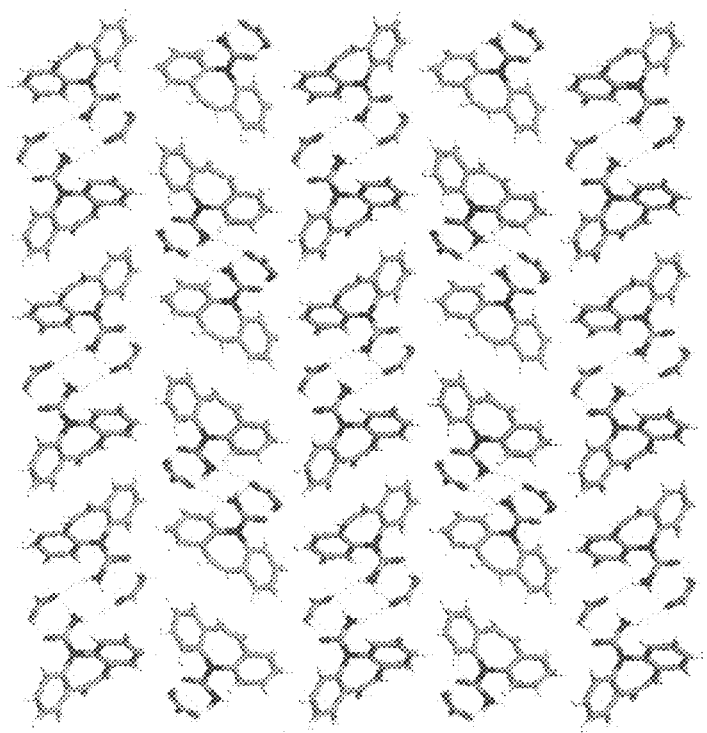

40 mg (0.1693 mmol) carbamazepine was dissolved in approximately 2 mL formic acid. Slow evaporation of the solvent yielded off-white starbursts of a 1:1 carbamazepine/formic acid co-crystal, as shown in FIG. 22B.

Crystal data: (Bruker SMART-APEX CCD Diffractometer). $C_{16}H_{14}N_2O_3$, M=282.29, monoclinic P21/c; a=5.2031 (9), b=14.741(2), c=17.882(3) Å, α=90°, 13=98.132(3)°, γ90°, V=1357.7(4)Å$^3$, T=100 K, Z=4, μ(MO-Kα)=0.097 mm$^{-1}$, D$_c$=1.381 Mg/m$^3$, λ=0.71073 Å$^3$, F(000)592, 2θ$_{max}$=28.3. 9402 reflections measured, 3191 unique (R$_{int}$=0.111). Final residuals for 190 parameters were R$_1$=0.0533 and wR$_2$=0.1268 for I>2σ(I).

Crystal packing: The co-crystals are sustained by hydrogen bonded carboxylic acid-amine heterodimers arranged in centrosymmetric tetramers.

Infrared Spectroscopy: (Nicolet Avatar 320 FTIR). 3439 cm$^{-1}$, (1° amine stretch, CBZ); 3026 cm$^{-1}$ (C—H stretch, CBZ); 1692 cm$^{-1}$, (1° amide, C=O stretch).

Melting Point: 187° C. (MEL-TEMP). (carbamazepine m.p.=191-192° C., formic acid m.p.=8.4° C.).

Thermogravimetric Analysis: (TA Instruments 2950 Hi-Resolution TGA). 14.60% weight loss starting at 123° and a 68.91% weight loss starting at 196° followed by complete decomposition.

EXAMPLE 19

Multi-Component Crystal of Carbamazepine: Carbamazepine/Trimesic Acid (1:1 Stoichiometry)

Figure 23A:
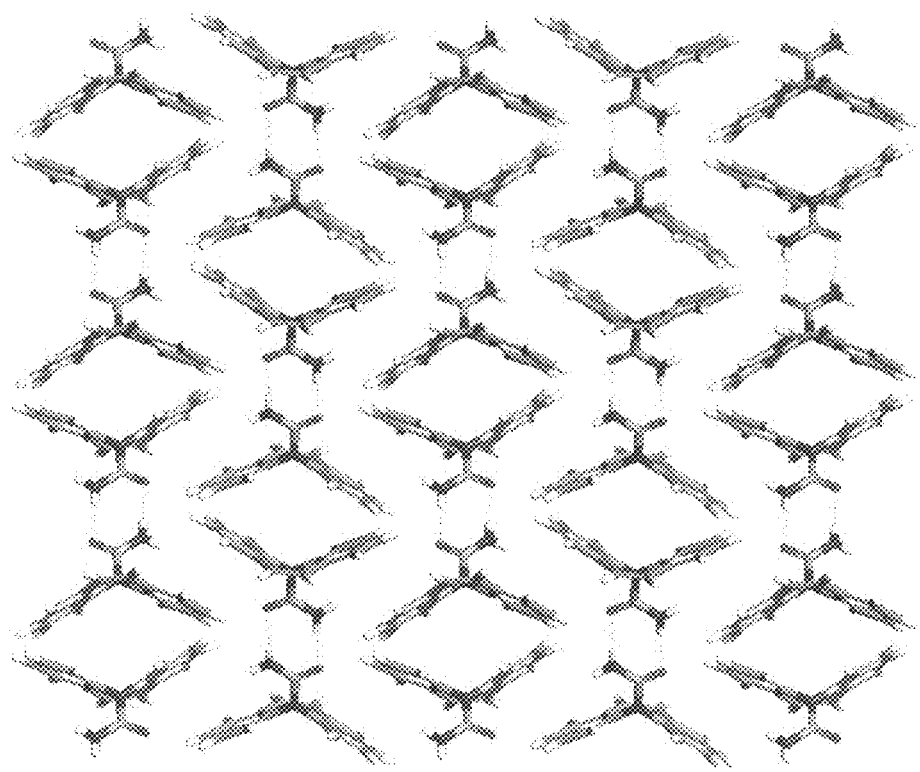
FIGS. 23A and 23B show the crystal structure of carbamazepine and carbamazepine/trimesic acid.
Figure 23B:
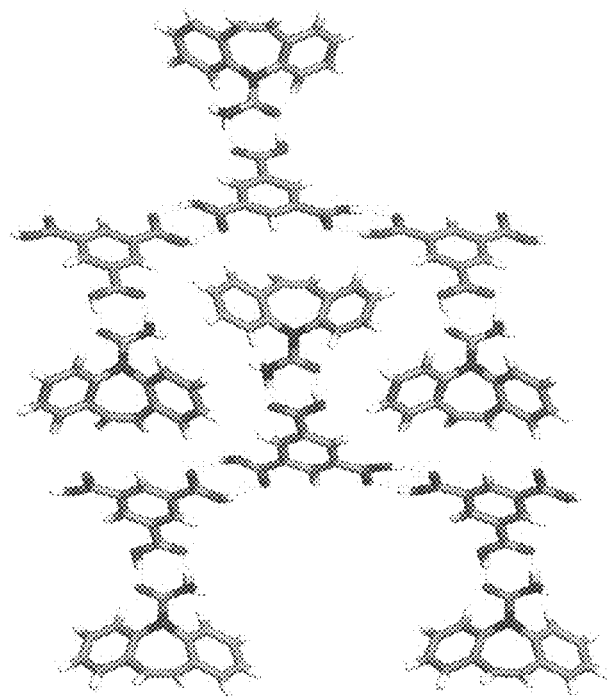
Figure 24:
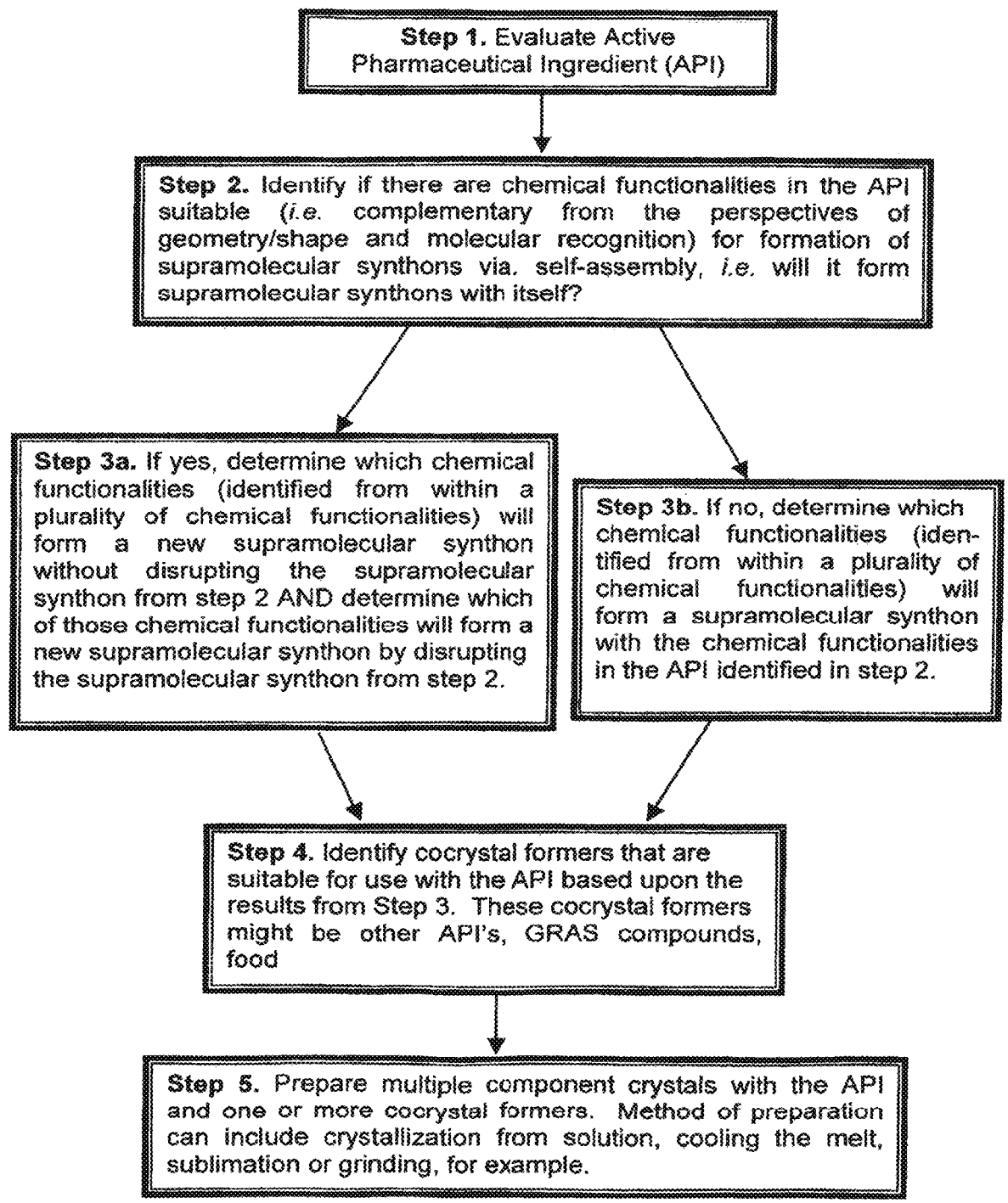
FIG. 24 shows an exemplified scheme for preparing multiple-component phase compositions of the subject invention.

36 mg (0.1524 mmol) carbamazepine and 31 mg (0.1475 mmol) trimesic acid were dissolved in a solvent mixture of approximately 2 mL methanol and 2 mL dichloromethane. Slow evaporation of the solvent mixture yielded white starbursts of a 1:1 carbamazepine/trimesic acid co-crystal, as shown in FIG. 23B.

Crystal data: (Bruker SMART-APEX CCD Diffractometer). C$_{24}$H$_{18}$N$_2$O$_7$, M=446.26, monoclinic C2/c; a=32.5312 (50), b=5.2697(8), c=24.1594(37) Å, α=90°, β=98.191(3)°, 7=90°, V=4099.39(37) Å$^3$, T=−173 K, Z=8, μ(MO-Kα)=0.110 mm$^{-1}$, D$_c$=1.439 Mg/m$^3$, λ=0.71073 Å$^3$, F(000)1968, 2θ$_{max}$=26.43°. 11581 reflections measured, 4459 unique (R$_{int}$=0.0611). Final residuals for 2777 parameters were R$_1$=0.1563, wR$_2$=0.1887 for I>>2σ(I), and R$_1$=0.1441, wR$_2$=0.1204 for all 3601 data.

Crystal packing: The co-crystals are sustained by hydrogen bonded carboxylic acid homodimers between carbamazepine and trimesic acid moieties and hydrogen bonded carboxylic acid-amine heterodimers between two trimesic acid moieties arranged in a stacked ladder formation.

Infrared Spectroscopy: (Nicolet Avatar 320 FTIR). 3486 cm$^{-1}$(N—H stretch, 1° amine, CBZ); 1688 cm$^{-1}$ (C=0, 1° amide stretch, CBZ); 1602 cm$^{-1}$ (C=C, CBZ).

Differential Scanning calorimetry: (TA Instruments 2920 DSC). 273° C. (endotherm). m.p.=NA, decomposes at 278° C. (MEL-TEMP). (carbamazepine m.p.=191-192° C., trimesic acid m.p.=380° C.)

Thermogravimetric Analysis: (TA Instruments 2950 Hi-Resolution TGA). 62.83% weight loss starting at 253° and a 30.20% weight loss starting at 278° followed by complete decomposition.

X-ray powder diffraction: (Rigaku Miniflex Diffractometer using CuKα (λ=1.540562), 30 kV, 15 mA). The powder data were collected over an angular range of 3 to 40 2 in continuous scan mode using a step size of 0.02 2 and a scan speed of 2.0/min. XRPD analysis experimental: 10.736, 12.087, 16.857, 24.857, 27.857.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A pharmaceutical composition comprising a pharmaceutically acceptable carrier and a therapeutically effective amount of a co-crystal comprising supramolecular synthons, each supramolecular synthon formed from stoichiometric amounts of at least one active pharmaceutical ingredient (API) and at least one co-former and each supramolecular synthon comprising an API homosynthon formed via non-covalent hydrogen bonding,
   wherein the API has a first chemical functionality that permits formation of API homosynthons through non-covalent hydrogen bonding when the API is in its pure form,
   wherein the co-former has a second chemical functionality complimentary to the first chemical functionality via non-covalent hydrogen bonding,
   wherein said co-former is a solid at room temperature and atmospheric pressure when the co-former is in its pure form, and
   wherein supramolecular synthons are formed via non-covalent hydrogen bonding between the first chemical functionality of the API and the second chemical functionality of the co-former.

2. The pharmaceutical composition of claim 1, wherein the at least one API participating in each supramolecular synthon is two APIs of the at least one API that are bonded to one another through hydrogen bonding to form at least one homosynthon dimer.

3. The pharmaceutical composition of claim 2, wherein the at least one co-former is two of the co-former and the at least one API is two of the API, wherein the at least one homosynthon dimer is one homosynthon dimer, and wherein the supramolecular synthon forms a tetramer, the tetramer being comprised of the two co-formers and two APIs, and each co-former being attached to the homodimer by hydrogen bonds.

4. The pharmaceutical composition of claim 2, wherein the at least one co-former is two co-formers, wherein the at least one homosynthon dimer is two homosynthon dimers, and wherein the supramolecular synthon results in a hexamer.

5. The pharmaceutical composition of claim 1, wherein the supramolecular synthon comprises a plurality of the API and a plurality of the co-former, wherein the supramolecular synthon comprises a chain of homosynthon dimers, each homosynthon dimer formed by hydrogen bonding of one of the plurality of the API to another of the plurality of the API, and wherein the homosynthon dimers are bonded to the co-former by hydrogen bonding.

6. The pharmaceutical composition of claim 2, wherein the at least one co-former participating in each supramolecular synthon is two co-formers forming a homosynthon.

7. The pharmaceutical composition of claim 1, wherein the non-covalent bonding of said API homosynthons is carboxylic acid:carboxylic acid hydrogen bonding.

8. The pharmaceutical composition of claim 1, wherein the non-covalent bonding of said API homosynthons is carboxamide:carboxamide hydrogen bonding.

9. A pharmaceutical composition comprising a pharmaceutically acceptable carrier and a therapeutically effective amount of a co-crystal comprising supramolecular synthons, each supramolecular synthon formed from stoichiometric amounts of at least one active pharmaceutical ingredient (API) and at least one co-former, wherein the API has a first chemical functionality that permits formation of API homosynthons through non-covalent hydrogen bonding when the API is in its pure form, wherein the co-former has a second chemical functionality complimentary to the first chemical functionality via non-covalent hydrogen bonding, wherein said co-former is a solid at room temperature and atmospheric pressure when the co-former is in its pure form, wherein supramolecular synthons are formed via non-covalent hydrogen bonding between the first chemical functionality of the API and the second chemical functionality of the co-former, and wherein the at least one API participating in each supramolecular synthon is two APIs and the at least one co-former is one co-former, and wherein each of the two APIs is bonded by non-covalent bonding to the one co-former.

10. A pharmaceutical composition comprising a pharmaceutically acceptable carrier and a therapeutically effective amount of a co-crystal comprising supramolecular synthons, each supramolecular synthon formed from stoichiometric amounts of at least one active pharmaceutical ingredient (API) and at least one co-former, wherein the API has a first chemical functionality that permits formation of API homosynthons through non-covalent hydrogen bonding when the API is in its pure form, wherein the co-former has a second chemical functionality complimentary to the first chemical functionality via non-covalent hydrogen bonding, wherein said co-former is a solid at room temperature and atmospheric pressure when the co-former is in its pure form, wherein supramolecular synthons are formed via non-covalent hydrogen bonding between the first chemical functionality of the API and the second chemical functionality of the co-former, and wherein the first chemical functionality is (i) a carboxamide, (ii) a carbonyl, or (iii) an amine.

11. The pharmaceutical composition of claim 10, wherein the supramolecular synthon comprises a heterosynthon dimer formed by non-covalent hydrogen bonding of the API to the co-former.

12. The pharmaceutical composition of claim 10, wherein the supramolecular synthon comprises a plurality of the API and a plurality of the co-former, wherein the supramolecular synthon is a chain of supramolecular heterosynthons, each supramolecular heterosynthon formed by non-covalent hydrogen bonding of one API to one co-former, and wherein the supramolecular heterosynthons are bonded to one another by non-covalent hydrogen bonding.

13. The pharmaceutical composition of claim 10, wherein the co-crystal is a hydrated co-crystal, wherein the supramolecular synthon comprises a plurality of the API and a plurality of the co-former, wherein the supramolecular synthon affords a sheet of the API, each of the APIs in the sheet bonded to one another and to a co-former by non-covalent hydrogen bonding to a water molecule.

14. The pharmaceutical composition of claim 10, wherein the at least one co-former participating in each supramolecular synthon is two co-formers forming a homosynthon, the at least one API in each supramolecular synthon is two APIs, and wherein each of the two APIs is bonded by non-covalent bonding to one of the two co-formers.

15. The pharmaceutical composition of claim 10, wherein the at least one API participating in each supramolecular synthon is two APIs and the at least one co-former participating in each supramolecular synthon is two co-formers forming a homosynthon, and wherein one of the two APIs is non-covalently bonded to one of the co-formers and the other of the two APIs is non-covalently bonded to the other of the two co-formers.

16. The pharmaceutical composition of claim 10, wherein the supramolecular synthons are non-covalently bonded to one another by non-covalent bonding to a solvent molecule.

17. The pharmaceutical composition of claim 10, wherein the second chemical functionality complimentary to the first chemical functionality is (i) two identical second chemical functionalities on the co-former, (ii) three identical second chemical functionalities on the co-former, or (iii) four identical second chemical functionalities on the co-former.

18. The pharmaceutical composition of claim 10, wherein the first chemical functionality is a carboxamide.

19. The pharmaceutical composition of claim 10, wherein the first chemical functionality is a carbonyl.

20. The pharmaceutical composition of claim 10, wherein the first chemical functionality is an amine.

21. A pharmaceutical composition comprising a pharmaceutically acceptable carrier and a therapeutically effective amount of a co-crystal comprising supramolecular synthons, each supramolecular synthon formed from stoichiometric amounts of at least one active pharmaceutical ingredient (API) and at least one co-former, wherein the API has a first chemical functionality that permits formation of API homosynthons through non-covalent hydrogen bonding when the API is in its pure form, wherein the co-former has a second chemical functionality complimentary to the first chemical functionality via non-covalent hydrogen bonding, wherein said co-former is a solid at room temperature and atmospheric pressure when the co-former is in its pure form, wherein supramolecular synthons are formed via non-covalent hydrogen bonding between the first chemical functionality of the API and the second chemical functionality of the co-former, and wherein the first chemical functionality and the second chemical functionality form (i) a carbonyl:amide hydrogen bond, (ii) a carbonyl:amine hydrogen bond, (iii) a carboxylic acid:pyridine hydrogen bond, (iv) a carboxylic acid:aromatic amine hydrogen bond, (v) a carboxylic acid:carboxylic acid hydrogen bond, (vi) a carboxylic acid:carboxamide hydrogen bond, (vii) a carboxylic acid:amine hydrogen bond, (viii) a carboxylic acid:carbonyl hydrogen bond, (ix) an amine:sulfonamide hydrogen bond, or (x) a carbonyl:sulfonamide hydrogen bond.

* * * * *

Disclaimer

10,633,344 B2 - Michael J. Zaworotko, Tampa, FL (US); Nair Rodriguez-Hornedo, Ann Arbor, MI (US); Brian Moulton, Temple Terrance, FL (US). MULTIPLE-COMPONENT SOLDI PHASES CONTAINING AT LEAST ONE ACTIVE PHARMACEUTICAL INGREDIENT. Patent dated April 28, 2020. Disclaimer filed June 6, 2024, by the assignee, The Regents of the University of Michigan, University of South Florida.

I hereby disclaim the following complete Claim 16 of said patent.

*(Official Gazette, September 17, 2024)*